(12) United States Patent
Vojdani

(10) Patent No.: US 7,252,957 B2
(45) Date of Patent: Aug. 7, 2007

(54) IDENTIFICATION OF ETIOLOGY OF AUTISM

(75) Inventor: Aristo Vojdani, Los Angeles, CA (US)

(73) Assignee: Immunosciences Lab., Inc., Beverly Hills, CA (US)

( * ) Notice: Subject to any disclaimer, the term of this patent is extended or adjusted under 35 U.S.C. 154(b) by 347 days.

(21) Appl. No.: 10/770,712

(22) Filed: Feb. 3, 2004

(65) Prior Publication Data

US 2005/0170333 A1 Aug. 4, 2005

(51) Int. Cl.
*G01N 33/53* (2006.01)
(52) U.S. Cl. .................. 435/7.1; 435/7.8; 435/7.92; 435/235.1; 436/86
(58) Field of Classification Search .............. 435/7.1, 435/7.8, 7.92, 235.1; 436/86
See application file for complete search history.

(56) References Cited

OTHER PUBLICATIONS

New Riverside University Dictionary 1994, p. 445.*
A.M. Comi, et al., "Familial Clustering of Autoimmune Disorders and Evaluation of Medical Risk Factors in Autism," *Journal of Child Neurology*, vol. 14, #6, Jun. 1999; pp. 388-394.
Stella Chess, et al., "Behavioral Consequences of Congenital Rubella" *The Journal of Pediatrics*, 1978 vol. 93, #4, pp. 699-703.
M. M. Desmond, et al., "Congenital Rubella Encephalitis," *The Journal of Pediatrics*, vol. 71, #3, Sep. 1967, pp. 311-331.
K. Ahlfors, et al., "Congenital Cytomegalovirus Infection and Disease in Sweden and the Relative Importance of Primary and Secondary Maternal Infections," *Scand J. Infect Dis.* 16: 129-137, 1984.
L. R. Goldman, et al., "Chemicals in the Environment and Developmental Toxicity to Children: A Public Health and Policy Perspective," *Environmental Health Perspectives Supplements*, vol. 108, #S3, Jun. 2000, pp. 1-12.
G. J. Myers, et al., "Prenatal Methylmercury Exposure and Children: Neurologic, Developmental, and Behavioral Research," *Environmental Health Perspectives Supplements*, vol. 106, #S3, Jun. 1998, pp. 1-13.

P.M. Rodier, et al., "Linking Etiologies in Humans and Animal Models: Studies of Autism," *Reproductive Toxicology.*, vol. 11, Nos. 2/3, 1997, pp. 417-422.
S.B. Edelson, et al., "Autism: Xenobiotic Influences," *Toxicology and Industrial Health*, vol. 14, #6, 1998, pp. 799-811.
Michael B. First, M.D., Editor, "Section 299.00 Autistic Disorder," *Diagnostic and Statistical Manual—Text Revision*, American Psychiatric Association, DSM IV-TR™, 2000.
V. K. Singh, et al., "Circulating Autoantibodies to Neuronal and Glial Filament Proteins in Autism," *Pediatric Neurology*, vol. 17, No. 1, 1997, pp. 88-90.
V. K. Singh, et al., "Antibodies to Myelin Basic Protein in Children with Autistic Behavior," *Brain, Behavior, and Immunity* 7, 97-103 (1993).
A. Vojdani, et al., "Antibodies to Neuron-Specific Antigens in Children with Autism: Possible Cross-Reaction with Encephalitogenic Proteins from Milk, Chlamydia pneumoniae and Streptococcus Group A," *Journal of Neuroimmunology*, 129 (2002) 168-177.
A. Vojdani, et al., "Infections, Toxic Chemicals and Dietary Peptides Binding to Lymphocyte Receptors and Tissue Enzymes Are Major Instigators of Autoimmunity in Autism," *International Journal of Immunopathology and Pharmacology*, vol. 16, No. 3, 189-199 (2003).
E.L. Cooper, "Neuroimmunology of Autism: A Multifaceted Hypothesis," *International Journal of Immunopathology and Pharmacology*, vol. 16, No. 3, 289-292 (2003).

\* cited by examiner

*Primary Examiner*—Long V. Le
*Assistant Examiner*—Jacob Cheu
(74) *Attorney, Agent, or Firm*—Knobbe, Martens, Olson and Bear, LLP

(57) ABSTRACT

Disclosed herein is a method for following up a prognosis of children with autism before and after treatment with different modalities administered by their clinicians, confirming the involvement of infectious agents, dietary proteins, and toxic chemicals in development of autism. The method utilizes detection of increased amounts of antibodies against an antigen based on infectious agent, toxic chemicals, or dietary proteins. Another method utilizes detection of antibodies to a self-tissue or peptide.

7 Claims, 22 Drawing Sheets

FIGURE 5

```
                         SEQUENCE LISTING

<160> NUMBER OF SEQ ID NOS: 133

<210> SEQ ID NO 1
<211> LENGTH: 766
<212> TYPE: PRT
<213> ORGANISM: Homo sapiens

<400> SEQUENCE: 1

Met Lys Thr Pro Trp Arg Val Leu Leu Gly Leu Leu Gly Ala Ala Ala
 1               5                  10                  15

Leu Val Thr Ile Ile Thr Val Pro Val Val Leu Asn Lys Gly Thr
             20                  25                  30

Asp Asp Ala Thr Ala Asp Ser Arg Lys Thr Tyr Thr Leu Thr Asp Tyr
         35                  40                  45

Leu Lys Asn Thr Tyr Arg Leu Lys Leu Tyr Ser Leu Arg Trp Ile Ser
     50                  55                  60

Asp His Glu Tyr Leu Tyr Lys Gln Glu Asn Asn Ile Leu Val Phe Asn
 65                  70                  75                  80

Ala Glu Tyr Gly Asn Ser Ser Val Phe Leu Glu Asn Ser Thr Phe Asp
                 85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

Glu Pro Asn Leu Pro Ser Tyr Arg Ile Thr Trp Thr Gly Lys Glu Asp
            180                 185                 190

Ile Ile Tyr Asn Gly Ile Thr Asp Trp Val Tyr Glu Glu Glu Val Phe
        195                 200                 205

Ser Ala Tyr Ser Ala Leu Trp Trp Ser Pro Asn Gly Thr Phe Leu Ala
    210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
            260                 265                 270

Thr Asp Ser Leu Ser Ser Val Thr Asn Ala Thr Ser Ile Gln Ile Thr
        275                 280                 285

Ala Pro Ala Ser Met Leu Ile Gly Asp His Tyr Leu Cys Asp Val Thr
    290                 295                 300
```

-continued

```
Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
            325                 330                 335

Trp Asn Cys Leu Val Ala Arg Gln His Ile Glu Met Ser Thr Thr Gly
        340                 345                 350

Trp Val Gly Arg Phe Arg Pro Ser Glu Pro His Phe Thr Leu Asp Gly
    355                 360                 365

Asn Ser Phe Tyr Lys Ile Ile Ser Asn Glu Glu Gly Tyr Arg His Ile
370                 375                 380

Cys Tyr Phe Gln Ile Asp Lys Lys Asp Cys Thr Phe Ile Thr Lys Gly
385                 390                 395                 400

Thr Trp Glu Val Ile Gly Ile Glu Ala Leu Thr Ser Asp Tyr Leu Tyr
                405                 410                 415

Tyr Ile Ser Asn Glu Tyr Lys Gly Met Pro Gly Gly Arg Asn Leu Tyr
            420                 425                 430

Lys Ile Gln Leu Ser Asp Tyr Thr Lys Val Thr Cys Leu Ser Cys Glu
        435                 440                 445

Leu Asn Pro Glu Arg Cys Gln Tyr Tyr Ser Val Ser Phe Ser Lys Glu
    450                 455                 460

Ala Lys Tyr Tyr Gln Leu Arg Cys Ser Gly Pro Gly Leu Pro Leu Tyr
465                 470                 475                 480

Thr Leu His Ser Ser Val Asn Asp Lys Gly Leu Arg Val Leu Glu Asp
                485                 490                 495

Asn Ser Ala Leu Asp Lys Met Leu Gln Asn Val Gln Met Pro Ser Lys
            500                 505                 510

Lys Leu Asp Phe Ile Ile Leu Asn Glu Thr Lys Phe Trp Tyr Gln Met
        515                 520                 525

Ile Leu Pro Pro His Phe Asp Lys Ser Lys Lys Tyr Pro Leu Leu Leu
    530                 535                 540

Asp Val Tyr Ala Gly Pro Cys Ser Gln Lys Ala Asp Ile Val Phe Arg
545                 550                 555                 560

Leu Asn Trp Ala Thr Tyr Leu Ala Ser Thr Glu Asn Ile Ile Val Ala
                565                 570                 575

Ser Phe Asp Gly Arg Gly Ser Gly Tyr Gln Gly Asp Lys Ile Met His
            580                 585                 590

Ala Ile Asn Arg Arg Leu Gly Thr Phe Glu Val Glu Asp Gln Ile Glu
        595                 600                 605

Ala Ala Arg Gln Phe Ser Lys Met Gly Phe Val Asp Asn Lys Arg Ile
    610                 615                 620

Ala Ile Trp Gly Trp Ser Tyr Gly Gly Tyr Val Thr Ser Met Val Leu
625                 630                 635                 640

Gly Ser Gly Ser Gly Val Phe Lys Cys Gly Ile Ala Val Ala Pro Val
                645                 650                 655

Ser Arg Trp Glu Tyr Tyr Glu Ser Val Tyr Thr Glu Arg Tyr Met Gly
            660                 665                 670

Leu Pro Thr Pro Glu Asp Asn Leu Asp His Tyr Arg Asn Ser Thr Val
        675                 680                 685

Met Ser Arg Ala Glu Asn Phe Lys Gln Val Glu Tyr Leu Leu Ile His
    690                 695                 700

Gly Thr Ala Asp Asp Asn Val His Phe Gln Gln Ser Ala Gln Ile Ser
705                 710                 715                 720

Lys Ala Leu Val Asp Val Gly Val Asp Phe Gln Ala Met Trp Tyr Thr
```

```
                    725                 730                 735
Asp Glu Asp His Gly Ile Ala Ser Ser Thr Ala His Gln His Ile Tyr
            740                 745                 750
Thr His Met Ser His Phe Ile Lys Gln Cys Phe Ser Leu Pro
            755                 760                 765

<210> SEQ ID NO 2
<211> LENGTH: 767
<212> TYPE: PRT
<213> ORGANISM: Rattus norvegicus

<400> SEQUENCE: 2

Met Lys Thr Pro Trp Lys Val Leu Leu Gly Leu Leu Val Ala Ala
  1               5                  10                  15
Leu Val Thr Ile Ile Thr Val Pro Val Leu Leu Asn Lys Asp Glu
                 20                  25                  30
Ala Ala Ala Asp Ser Ala Arg Thr Tyr Thr Leu Ala Asp Tyr Leu Lys
             35                  40                  45
Asn Thr Phe Arg Val Lys Ser Tyr Ser Leu Arg Trp Val Ser Asp Ser
 50                  55                  60
Glu Tyr Leu Tyr Lys Gln Glu Asn Asn Ile Leu Leu Phe Asn Ala Glu
 65                  70                  75                  80
His Gly Asn Ser Ser Ile Phe Leu Glu Asn Ser Thr Phe Glu Ile Phe
                 85                  90                  95
Gly Asp Ser Ile Ser Asp Tyr Ser Val Ser Pro Asp Arg Leu Phe Val
                100                 105                 110
Leu Leu Glu Tyr Asn Tyr Val Lys Gln Trp Arg His Ser Tyr Thr Ala
                115                 120                 125
Ser Tyr Ser Ile Tyr Asp Leu Asn Lys Arg Gln Leu Ile Thr Glu Glu
            130                 135                 140
Lys Ile Pro Asn Asn Thr Gln Trp Ile Thr Trp Ser Gln Glu Gly His
145                 150                 155                 160
Lys Leu Ala Tyr Val Trp Lys Asn Asp Ile Tyr Val Lys Ile Glu Pro
                165                 170                 175
His Leu Pro Ser His Arg Ile Thr Ser Thr Gly Lys Glu Asn Val Ile
                180                 185                 190
Phe Asn Gly Ile Asn Asp Trp Val Tyr Glu Glu Glu Ile Phe Gly Ala
                195                 200                 205
Tyr Ser Ala Leu Trp Trp Ser Pro Asn Gly Thr Phe Leu Ala Tyr Ala
            210                 215                 220
Gln Phe Asn Asp Thr Gly Val Pro Leu Ile Glu Tyr Ser Phe Tyr Ser
225                 230                 235                 240
Asp Glu Ser Leu Gln Tyr Pro Lys Thr Val Trp Ile Pro Tyr Pro Lys
                245                 250                 255
Ala Gly Ala Val Asn Pro Thr Val Lys Phe Phe Ile Val Asn Thr Asp
                260                 265                 270
Ser Leu Ser Ser Thr Thr Thr Ile Pro Met Gln Ile Thr Ala Pro
            275                 280                 285
Ala Ser Val Thr Thr Gly Asp His Tyr Leu Cys Asp Val Ala Trp Val
            290                 295                 300
Ser Glu Asp Arg Ile Ser Leu Gln Trp Leu Arg Arg Ile Gln Asn Tyr
305                 310                 315                 320
Ser Val Met Ala Ile Cys Asp Tyr Asp Lys Thr Thr Leu Val Trp Asn
                325                 330                 335
```

```
Cys Pro Thr Thr Arg Glu His Ile Glu Thr Ser Ala Thr Gly Trp Cys
            340                 345                 350

Gly Arg Phe Arg Pro Ala Glu Pro His Phe Thr Ser Asp Gly Ser Ser
        355                 360                 365

Phe Tyr Lys Ile Val Ser Asp Lys Asp Gly Tyr Lys His Ile Cys Gln
    370                 375                 380

Phe Gln Lys Asp Arg Lys Pro Glu Gln Val Cys Thr Phe Ile Thr Lys
385                 390                 395                 400

Gly Ala Trp Glu Val Ile Ser Ile Glu Ala Leu Thr Ser Asp Tyr Leu
                405                 410                 415

Tyr Tyr Ile Ser Asn Glu Tyr Lys Glu Met Pro Gly Arg Asn Leu
            420                 425                 430

Tyr Lys Ile Gln Leu Thr Asp His Thr Asn Lys Lys Cys Leu Ser Cys
            435                 440                 445

Asp Leu Asn Pro Glu Arg Cys Gln Tyr Tyr Ser Val Ser Leu Ser Lys
        450                 455                 460

Glu Ala Lys Tyr Tyr Gln Leu Gly Cys Arg Gly Pro Gly Leu Pro Leu
465                 470                 475                 480

Tyr Thr Leu His Arg Ser Thr Asp Gln Lys Glu Leu Arg Val Leu Glu
                485                 490                 495

Asp Asn Ser Ala Leu Asp Lys Met Leu Gln Asp Val Gln Met Pro Ser
            500                 505                 510

Lys Lys Leu Asp Phe Ile Val Leu Asn Glu Thr Arg Phe Trp Tyr Gln
        515                 520                 525

Met Ile Leu Pro Pro His Phe Asp Lys Ser Lys Tyr Pro Leu Leu
        530                 535                 540

Ile Asp Val Tyr Ala Gly Pro Cys Ser Gln Lys Ala Asp Ala Ala Phe
545                 550                 555                 560

Arg Leu Asn Trp Ala Thr Tyr Leu Ala Ser Thr Glu Asn Ile Ile Val
                565                 570                 575

Ala Ser Phe Asp Gly Arg Gly Ser Gly Tyr Gln Gly Asp Lys Ile Met
            580                 585                 590

His Ala Ile Asn Lys Arg Leu Gly Thr Leu Glu Val Glu Asp Gln Ile
            595                 600                 605

Glu Ala Ala Arg Gln Phe Leu Lys Met Gly Phe Val Asp Ser Lys Arg
        610                 615                 620

Val Ala Ile Trp Gly Trp Ser Tyr Gly Gly Tyr Val Thr Ser Met Val
625                 630                 635                 640

Leu Gly Ser Gly Ser Gly Val Phe Lys Cys Gly Ile Ala Val Ala Pro
                645                 650                 655

Val Ser Arg Trp Glu Tyr Tyr Asp Ser Val Tyr Thr Glu Arg Tyr Met
            660                 665                 670

Gly Leu Pro Thr Pro Glu Asp Asn Leu Asp His Tyr Arg Asn Ser Thr
        675                 680                 685

Val Met Ser Arg Ala Glu Asn Phe Lys Gln Val Glu Tyr Leu Leu Ile
        690                 695                 700

His Gly Thr Ala Asp Asp Asn Val His Phe Gln Ser Ala Gln Ile
705                 710                 715                 720

Ser Lys Ala Leu Val Asp Ala Gly Val Asp Phe Gln Ala Met Trp Tyr
                725                 730                 735

Thr Asp Glu Asp His Gly Ile Ala Ser Ser Thr Ala His Gln His Ile
            740                 745                 750

Tyr Ser His Met Ser His Phe Leu Gln Gln Cys Phe Ser Leu Arg
```

```
              755                 760                 765

<210> SEQ ID NO 3
<211> LENGTH: 760
<212> TYPE: PRT
<213> ORGANISM: Mus musculus

<400> SEQUENCE: 3

Met Lys Thr Pro Trp Lys Val Leu Leu Gly Leu Leu Gly Val Ala Ala
 1               5                  10                  15

Leu Val Thr Ile Ile Thr Val Pro Ile Val Leu Leu Ser Lys Asp Glu
            20                  25                  30

Ala Ala Ala Asp Ser Arg Arg Thr Tyr Ser Leu Ala Asp Tyr Leu Lys
        35                  40                  45

Ser Thr Phe Arg Val Lys Ser Tyr Ser Leu Trp Trp Val Ser Asp Phe
    50                  55                  60

Glu Tyr Leu Tyr Lys Gln Glu Asn Asn Ile Leu Leu Leu Asn Ala Glu
65                  70                  75                  80

His Gly Asn Ser Ser Ile Phe Leu Glu Asn Ser Thr Phe Glu Ser Phe
                85                  90                  95

Gly Tyr His Ser Val Ser Pro Asp Arg Leu Phe Val Leu Leu Glu Tyr
           100                 105                 110

Asn Tyr Val Lys Gln Trp Arg His Ser Tyr Thr Ala Ser Tyr Asn Ile
       115                 120                 125

Tyr Asp Val Asn Lys Arg Gln Leu Ile Thr Glu Glu Lys Ile Pro Asn
130                 135                 140

Asn Thr Gln Trp Ile Thr Trp Ser Pro Glu Gly His Lys Leu Ala Tyr
145                 150                 155                 160

Val Trp Lys Asn Asp Ile Tyr Val Lys Val Glu Pro His Leu Pro Ser
                165                 170                 175

His Arg Ile Thr Ser Thr Gly Glu Glu Asn Val Ile Tyr Asn Gly Ile
           180                 185                 190

Thr Asp Trp Val Tyr Glu Glu Glu Val Phe Gly Ala Tyr Ser Ala Leu
       195                 200                 205

Trp Trp Ser Pro Asn Asn Thr Phe Leu Ala Tyr Ala Gln Phe Asn Asp
210                 215                 220

Thr Gly Val Pro Leu Ile Glu Tyr Ser Phe Tyr Ser Asp Glu Ser Leu
225                 230                 235                 240

Gln Tyr Pro Lys Thr Val Trp Ile Pro Tyr Pro Lys Ala Gly Ala Val
                245                 250                 255

Asn Pro Thr Val Lys Phe Phe Ile Val Asn Ile Asp Ser Leu Ser Ser
           260                 265                 270

Ser Ser Ser Ala Ala Pro Ile Gln Ile Pro Ala Pro Ala Ser Val Ala
       275                 280                 285

Arg Gly Asp His Tyr Leu Cys Asp Val Val Trp Ala Thr Glu Glu Arg
290                 295                 300

Ile Ser Leu Gln Trp Leu Arg Arg Ile Gln Asn Tyr Ser Val Met Ala
305                 310                 315                 320

Ile Cys Asp Tyr Asp Lys Ile Asn Leu Thr Trp Asn Cys Pro Ser Glu
                325                 330                 335

Gln Gln His Val Glu Met Ser Thr Thr Gly Trp Val Gly Arg Phe Arg
           340                 345                 350

Pro Ala Glu Pro Tyr Leu Thr Ser Asp Gly Ser Ser Phe Tyr Lys Ile
       355                 360                 365
```

-continued

```
Ile Ser Asp Lys Asp Gly Tyr Lys His Ile Cys His Phe Pro Lys Asp
370                 375                 380

Lys Lys Asp Cys Thr Phe Ile Thr Lys Gly Ala Trp Glu Val Ile Ser
385                 390                 395                 400

Ile Glu Ala Leu Thr Ser Asp Tyr Leu Tyr Tyr Ile Ser Asn Gln Tyr
                405                 410                 415

Lys Glu Met Pro Gly Gly Arg Asn Leu Tyr Lys Ile Gln Leu Thr Asp
            420                 425                 430

His Thr Asn Val Lys Cys Leu Ser Cys Asp Leu Asn Pro Glu Arg Cys
        435                 440                 445

Gln Tyr Tyr Ala Val Ser Phe Ser Lys Glu Ala Lys Tyr Tyr Gln Leu
    450                 455                 460

Gly Cys Trp Gly Pro Gly Leu Pro Leu Tyr Thr Leu His Arg Ser Thr
465                 470                 475                 480

Asp His Lys Glu Leu Arg Val Leu Glu Asp Asn Ser Ala Leu Asp Arg
                485                 490                 495

Met Leu Gln Asp Val Gln Met Pro Ser Lys Lys Leu Asp Phe Ile Val
            500                 505                 510

Leu Asn Glu Thr Arg Phe Trp Tyr Gln Met Ile Leu Pro Pro His Phe
        515                 520                 525

Asp Lys Ser Lys Lys Tyr Pro Leu Leu Leu Asp Val Tyr Ala Gly Pro
    530                 535                 540

Cys Ser Gln Lys Ala Asp Ala Ser Phe Arg Leu Asn Trp Ala Thr Tyr
545                 550                 555                 560

Leu Ala Ser Thr Glu Asn Ile Ile Val Ala Ser Phe Asp Gly Arg Gly
                565                 570                 575

Ser Gly Tyr Gln Gly Asp Lys Ile Met His Ala Ile Asn Arg Arg Leu
            580                 585                 590

Gly Thr Leu Glu Val Glu Asp Gln Ile Glu Ala Ala Arg Gln Phe Val
        595                 600                 605

Lys Met Gly Phe Val Asp Ser Lys Arg Val Ala Ile Trp Gly Trp Ser
    610                 615                 620

Tyr Gly Gly Tyr Val Thr Ser Met Val Leu Gly Ser Gly Ser Gly Val
625                 630                 635                 640

Phe Lys Cys Gly Ile Ala Val Ala Pro Val Ser Arg Trp Glu Tyr Tyr
                645                 650                 655

Asp Ser Val Tyr Thr Glu Arg Tyr Met Gly Leu Pro Ile Pro Glu Asp
            660                 665                 670

Asn Leu Asp His Tyr Arg Asn Ser Thr Val Met Ser Arg Ala Glu His
        675                 680                 685

Phe Lys Gln Val Glu Tyr Leu Leu Ile His Gly Thr Ala Asp Asp Asn
    690                 695                 700

Val His Phe Gln Gln Ser Ala Gln Ile Ser Lys Val Leu Val Asp Ala
705                 710                 715                 720

Gly Val Asp Phe Gln Ala Met Trp Tyr Thr Asp Glu Asp His Gly Ile
                725                 730                 735

Ala Ser Ser Thr Ala His Gln His Ile Tyr Ser His Met Ser His Phe
            740                 745                 750

Leu Gln Gln Cys Phe Ser Leu His
        755                 760

<210> SEQ ID NO 4
<211> LENGTH: 6
<212> TYPE: PRT
```

-continued

<213> ORGANISM: Homo sapiens

<400> SEQUENCE: 4

Val Pro Leu Leu Glu Asp
1               5

<210> SEQ ID NO 5
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 5

Val Val His Phe Phe Lys Asn Ile Val Thr Pro Arg Thr Pro Pro
1               5                   10                  15

Ser Gln Gly Lys
            20

<210> SEQ ID NO 6
<211> LENGTH: 17
<212> TYPE: PRT
<213> ORGANISM: Artificial Sequence
<220> FEATURE:
<223> OTHER INFORMATION: synthetically prepared peptide sequence

<400> SEQUENCE: 6

Glu Asn Pro Val Val His Phe Phe Lys Asn Ile Val Thr Pro Arg Thr
1               5                   10                  15

Pro

<210> SEQ ID NO 7
<211> LENGTH: 11
<212> TYPE: PRT
<213> ORGANISM: Artificial Sequence
<220> FEATURE:
<223> OTHER INFORMATION: synthetically prepared peptide sequence

<400> SEQUENCE: 7

Ala Ser Gln Lys Arg Pro Ser Gln Arg Ser Lys
1               5                   10

<210> SEQ ID NO 8
<211> LENGTH: 11
<212> TYPE: PRT
<213> ORGANISM: Artificial Sequence
<220> FEATURE:
<223> OTHER INFORMATION: synthetically prepared peptide sequence

<400> SEQUENCE: 8

Ala Asn Met Gln Arg Gln Ala Val Pro Thr Leu
1               5                   10

<210> SEQ ID NO 9
<211> LENGTH: 21
<212> TYPE: PRT
<213> ORGANISM: Artificial Sequence
<220> FEATURE:
<223> OTHER INFORMATION: synthetically prepared peptide sequence

<400> SEQUENCE: 9

Thr Gly Thr Glu Lys Leu Ile Glu Thr Tyr Phe Ser Lys Asn Tyr Gln
1               5                   10                  15

Asp Tyr Glu Tyr Leu
            20

<210> SEQ ID NO 10
<211> LENGTH: 18
<212> TYPE: PRT
<213> ORGANISM: Artificial Sequence
<220> FEATURE:
<223> OTHER INFORMATION: synthetically prepared peptide sequence

<400> SEQUENCE: 10

Gly Phe Tyr Thr Thr Gly Ala Val Arg Gln Ile Phe Gly Asp Tyr Lys
 1               5                   10                  15
Thr Thr

<210> SEQ ID NO 11
<211> LENGTH: 18
<212> TYPE: PRT
<213> ORGANISM: Artificial Sequence
<220> FEATURE:
<223> OTHER INFORMATION: synthetically prepared peptide sequence

<400> SEQUENCE: 11

Tyr Lys Thr Thr Ile Cys Gly Lys Gly Leu Ser Ala Thr Val Thr Gly
 1               5                   10                  15
Gly Gln

<210> SEQ ID NO 12
<211> LENGTH: 19
<212> TYPE: PRT
<213> ORGANISM: Artificial Sequence
<220> FEATURE:
<223> OTHER INFORMATION: synthetically prepared peptide sequence

<400> SEQUENCE: 12

Ser Arg Gly Gln His Gln Ala His Ser Leu Glu Arg Val Cys His Cys
 1               5                   10                  15
Leu Gly Lys

<210> SEQ ID NO 13
<211> LENGTH: 16
<212> TYPE: PRT
<213> ORGANISM: Artificial Sequence
<220> FEATURE:
<223> OTHER INFORMATION: synthetically prepared peptide sequence

<400> SEQUENCE: 13

His Cys Leu Gly Lys Trp Leu Gly His Pro Asp Lys Phe Val Gly Ile
 1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: synthetically prepared peptide sequence

<400> SEQUENCE: 14

Met Glu Ser Ala Leu Asp Gln Leu Lys Gln Phe Thr Thr Val Val
 1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: synthetically prepared peptide sequence -continued

<400> SEQUENCE: 15

Glu Thr Thr Val Val Ala Asp Thr Gly Asp Phe His Ala Ile Asp
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: synthetically prepared peptide sequence

<400> SEQUENCE: 16

Phe His Ala Ile Asp Glu Tyr Lys Pro Gln Asp Ala Thr Thr Asn
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: synthetically prepared peptide sequence

<400> SEQUENCE: 17

Lys Leu Gly Gly Ser Gln Glu Asp Gln Ile Lys Asn Ala Ile Asp
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: synthetically prepared peptide sequence

<400> SEQUENCE: 18

Lys Asn Ala Ile Asp Lys Leu Phe Val Leu Phe Gly Ala Glu Ile
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: synthetically prepared peptide sequence

<400> SEQUENCE: 19

Gly Glu Leu Leu Gln Asp Asn Ala Lys Leu Val Pro Val Leu Ser
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: synthetically prepared peptide sequence

<400> SEQUENCE: 20

Val Pro Val Leu Ser Ala Lys Ala Ala Gln Ala Ser Asp Leu Glu
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: synthetically prepared peptide sequence

```
<400> SEQUENCE: 21

Gly Ile Arg Lys Phe Ala Ala Asp Ala Val Lys Leu Glu Arg Met
1               5                   10                  15

<210> SEQ ID NO 22
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 22

Gly Gln Phe Arg Val Ile Gly Pro Arg His Pro Ile Arg Ala Leu Val
1               5                   10                  15

Gly Asp Glu Val
            20

<210> SEQ ID NO 23
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 23

Gln Ala Pro Glu Tyr Arg Gly Arg Thr Glu Leu Leu Lys Asp Ala Ile
1               5                   10                  15

Gly Glu Gly Lys
            20

<210> SEQ ID NO 24
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 24

Arg Asp His Ser Tyr Gln Glu Glu Ala Ala Met Glu Leu Lys Val Glu
1               5                   10                  15

Asp Pro Phe Tyr
            20

<210> SEQ ID NO 25
<211> LENGTH: 16
<212> TYPE: PRT
<213> ORGANISM: Artificial Sequence
<220> FEATURE:
<223> OTHER INFORMATION: synthetically prepared peptide sequence

<400> SEQUENCE: 25

Val Phe Leu Cys Leu Gln Tyr Arg Leu Arg Gly Lys Leu Arg Ala Glu
1               5                   10                  15

<210> SEQ ID NO 26
<211> LENGTH: 24
<212> TYPE: PRT
<213> ORGANISM: Artificial Sequence
<220> FEATURE:
<223> OTHER INFORMATION: synthetically prepared peptide sequence

<400> SEQUENCE: 26

Arg Glu Ile Val Asp Arg Lys Tyr Ser Ile Cys Lys Ser Gly Cys Phe
1               5                   10                  15
```

Tyr Gln Lys Lys Glu Glu Asp Trp
            20

<210> SEQ ID NO 27
<211> LENGTH: 27
<212> TYPE: PRT
<213> ORGANISM: Artificial Sequence
<220> FEATURE:
<223> OTHER INFORMATION: synthetically prepared peptide sequence

<400> SEQUENCE: 27

Thr Val Thr Val Pro Ile Ala Leu Gly Glu Ser Asp Phe Glu Asn Leu
1               5                   10                  15

Asn Thr Glu Glu Phe Ser Ser Glu Ser Asp Met
            20                  25

<210> SEQ ID NO 28
<211> LENGTH: 27
<212> TYPE: PRT
<213> ORGANISM: Artificial Sequence
<220> FEATURE:
<223> OTHER INFORMATION: synthetically prepared peptide sequence

<400> SEQUENCE: 28

Thr Val Thr Val Pro Ile Ala Val Gly Glu Ser Asp Phe Glu Asn Leu
1               5                   10                  15

Asn Thr Glu Glu Phe Ser Ser Glu Ser Glu Leu
            20                  25

<210> SEQ ID NO 29
<211> LENGTH: 27
<212> TYPE: PRT
<213> ORGANISM: Artificial Sequence
<220> FEATURE:
<223> OTHER INFORMATION: synthetically prepared peptide sequence

<400> SEQUENCE: 29

Thr Val Thr Val Pro Ile Ala Val Gly Glu Ser Asp Phe Glu Asn Leu
1               5                   10                  15

Asn Thr Glu Asp Phe Ser Ser Glu Ser Asp Leu
            20                  25

<210> SEQ ID NO 30
<211> LENGTH: 27
<212> TYPE: PRT
<213> ORGANISM: Artificial Sequence
<220> FEATURE:
<223> OTHER INFORMATION: synthetically prepared peptide sequence

<400> SEQUENCE: 30

Thr Val Arg Val Pro Ile Ala Val Gly Glu Ser Asp Phe Glu Asn Leu
1               5                   10                  15

Asn Thr Glu Asp Val Ser Ser Glu Ser Asp Pro
            20                  25

<210> SEQ ID NO 31
<211> LENGTH: 21
<212> TYPE: PRT
<213> ORGANISM: Artificial Sequence
<220> FEATURE:
<223> OTHER INFORMATION: synthetically prepared peptide sequence

<400> SEQUENCE: 31

Ala Asn Glu Tyr Glu Arg Phe Val Pro Phe Ser Asp Gln Gln Ile Ser
1               5                   10                  15

Asn Asp Ala Ala Cys
            20

<210> SEQ ID NO 32
<211> LENGTH: 22
<212> TYPE: PRT
<213> ORGANISM: Artificial Sequence
<220> FEATURE:
<223> OTHER INFORMATION: synthetically prepared peptide sequence

<400> SEQUENCE: 32

Phe Leu Glu Asp Val Pro Leu Leu Glu Asp Ile Pro Leu Leu Glu Asp
1               5                  10                  15

Val Pro Leu Leu Glu Asp
            20

<210> SEQ ID NO 33
<211> LENGTH: 18
<212> TYPE: PRT
<213> ORGANISM: Artificial Sequence
<220> FEATURE:
<223> OTHER INFORMATION: synthetically prepared peptide sequence

<400> SEQUENCE: 33

Phe Leu Glu Asp Val Pro Leu Leu Glu Asp Ile Pro Leu Leu Glu Asp
1               5                  10                  15

Val Pro

<210> SEQ ID NO 34
<211> LENGTH: 18
<212> TYPE: PRT
<213> ORGANISM: Artificial Sequence
<220> FEATURE:
<223> OTHER INFORMATION: synthetically prepared peptide sequence

<400> SEQUENCE: 34

Leu Leu Glu Asp Thr Asp Phe Leu Glu Asp Pro Asp Phe Leu Glu Ala
1               5                  10                  15

Ile Asp

<210> SEQ ID NO 35
<211> LENGTH: 42
<212> TYPE: PRT
<213> ORGANISM: Artificial Sequence
<220> FEATURE:
<223> OTHER INFORMATION: synthetically prepared peptide sequence

<400> SEQUENCE: 35

Asp Ala Glu Phe Arg His Asp Ser Gly Tyr Glu Val His His Gln Lys
1               5                  10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 36
<211> LENGTH: 16
<212> TYPE: PRT
<213> ORGANISM: Artificial Sequence
<220> FEATURE:
<223> OTHER INFORMATION: synthetically prepared peptide sequence

<400> SEQUENCE: 36

```
Met Glu Cys Glu Lys Asn Leu Tyr Trp Ile Cys Asn Lys Pro Tyr Lys
1               5                   10                  15
```

<210> SEQ ID NO 37
<211> LENGTH: 26
<212> TYPE: PRT
<213> ORGANISM: Artificial Sequence
<220> FEATURE:
<223> OTHER INFORMATION: synthetically prepared peptide sequence

<400> SEQUENCE: 37

```
Pro Tyr Lys Cys Pro Glu Cys Gly Lys Ser Phe Ser Gln Lys Ser Asp
1               5                   10                  15

Leu Val Lys His Gln Arg Thr His Thr Gly
            20                  25
```

<210> SEQ ID NO 38
<211> LENGTH: 15
<212> TYPE: PRT
<213> ORGANISM: Artificial Sequence
<220> FEATURE:
<223> OTHER INFORMATION: synthetically prepared peptide sequence

<400> SEQUENCE: 38

```
Glu Glu Glu Asp Lys Lys Glu Asp Val Gly Thr Val Val Gly Ile
1               5                   10                  15
```

<210> SEQ ID NO 39
<211> LENGTH: 15
<212> TYPE: PRT
<213> ORGANISM: Artificial Sequence
<220> FEATURE:
<223> OTHER INFORMATION: synthetically prepared peptide sequence

<400> SEQUENCE: 39

```
Asn Tyr Thr Arg Leu Arg Lys Gln Met Ala Val Lys Lys Tyr Leu
1               5                   10                  15
```

<210> SEQ ID NO 40
<211> LENGTH: 21
<212> TYPE: PRT
<213> ORGANISM: Artificial Sequence
<220> FEATURE:
<223> OTHER INFORMATION: synthetically prepared peptide sequence

<400> SEQUENCE: 40

```
Gln Pro Phe Arg Pro Gln Gln Pro Tyr Pro Gln Pro Gln Pro Gln Tyr
1               5                   10                  15

Ser Gln Pro Gln Gln
            20
```

<210> SEQ ID NO 41
<211> LENGTH: 21
<212> TYPE: PRT
<213> ORGANISM: Artificial Sequence
<220> FEATURE:
<223> OTHER INFORMATION: synthetically prepared peptide sequence

<400> SEQUENCE: 41

```
Gln Pro Tyr Pro Gln Pro Gln Pro Gln Tyr Ser Gln Pro Gln Gln Pro
1               5                   10                  15

Ile Ser Gln Gln Gln
            20
```

<210> SEQ ID NO 42

-continued

```
<211> LENGTH: 21
<212> TYPE: PRT
<213> ORGANISM: Artificial Sequence
<220> FEATURE:
<223> OTHER INFORMATION: synthetically prepared peptide sequence

<400> SEQUENCE: 42

Gln Phe Leu Gly Gln Gln Gln Pro Phe Pro Pro Gln Gln Pro Tyr Pro
 1               5                  10                  15

Gln Pro Gln Pro Phe
            20

<210> SEQ ID NO 43
<211> LENGTH: 21
<212> TYPE: PRT
<213> ORGANISM: Artificial Sequence
<220> FEATURE:
<223> OTHER INFORMATION: synthetically prepared peptide sequence

<400> SEQUENCE: 43

Pro Leu Val Gln Gln Gln Gln Phe Leu Gly Gln Gln Pro Phe Pro
 1               5                  10                  15

Pro Gln Gln Pro Tyr
            20

<210> SEQ ID NO 44
<211> LENGTH: 21
<212> TYPE: PRT
<213> ORGANISM: Artificial Sequence
<220> FEATURE:
<223> OTHER INFORMATION: synthetically prepared peptide sequence

<400> SEQUENCE: 44

His Asn Val Val His Ala Ile Ile Leu His Gln Gln Gln Gln Gln
 1               5                  10                  15

Gln Glu Gln Lys Gln
            20

<210> SEQ ID NO 45
<211> LENGTH: 17
<212> TYPE: PRT
<213> ORGANISM: Artificial Sequence
<220> FEATURE:
<223> OTHER INFORMATION: synthetically prepared peptide sequence

<400> SEQUENCE: 45

Asn Pro Ser Gln Gln Gln Pro Gln Glu Gln Val Pro Leu Val Gln Gln
 1               5                  10                  15

Gln

<210> SEQ ID NO 46
<211> LENGTH: 19
<212> TYPE: PRT
<213> ORGANISM: Artificial Sequence
<220> FEATURE:
<223> OTHER INFORMATION: synthetically prepared peptide sequence

<400> SEQUENCE: 46

Gln Gln Leu Pro Gln Pro Gln Gln Pro Gln Gln Ser Phe Pro Gln Gln
 1               5                  10                  15

Gln Pro Phe

<210> SEQ ID NO 47
<211> LENGTH: 8
```

```
<212> TYPE: PRT
<213> ORGANISM: Artificial Sequence
<220> FEATURE:
<223> OTHER INFORMATION: synthetically prepared peptide sequence

<400> SEQUENCE: 47

Tyr Pro Phe Pro Gly Pro Ile Pro
 1               5

<210> SEQ ID NO 48
<211> LENGTH: 10
<212> TYPE: PRT
<213> ORGANISM: Artificial Sequence
<220> FEATURE:
<223> OTHER INFORMATION: synthetically prepared peptide sequence

<400> SEQUENCE: 48

Gly Tyr Tyr Pro Thr Tyr Gly Gly Trp Leu
 1               5                  10

<210> SEQ ID NO 49
<211> LENGTH: 27
<212> TYPE: PRT
<213> ORGANISM: Artificial Sequence
<220> FEATURE:
<223> OTHER INFORMATION: synthetically prepared peptide sequence

<400> SEQUENCE: 49

His Ser Asp Gly Thr Phe Thr Ser Glu Leu Ser Arg Leu Arg Glu Gly
 1               5                  10                  15

Ala Arg Leu Gln Arg Leu Leu Gln Gly Leu Val
            20                  25

<210> SEQ ID NO 50
<211> LENGTH: 30
<212> TYPE: PRT
<213> ORGANISM: Artificial Sequence
<220> FEATURE:
<223> OTHER INFORMATION: synthetically prepared peptide sequence

<400> SEQUENCE: 50

Thr Pro Pro Leu Leu Ala Ala Ile Leu Met Leu Ala Ser Leu Arg Ser
 1               5                  10                  15

His Ile Val Ser Asp His Phe Pro Val Asn Phe Arg Lys Phe
            20                  25                  30

<210> SEQ ID NO 51
<211> LENGTH: 199
<212> TYPE: PRT
<213> ORGANISM: Artificial Sequence
<220> FEATURE:
<223> OTHER INFORMATION: synthetically prepared peptide sequence

<400> SEQUENCE: 51

Arg Pro Lys His Pro Ile Lys His Gln Gly Leu Pro Gln Glu Val Leu
 1               5                  10                  15

Asn Glu Asn Leu Leu Arg Phe Phe Val Ala Pro Phe Pro Glu Val Phe
            20                  25                  30

Gly Lys Glu Lys Val Asn Glu Leu Ser Lys Asp Ile Gly Ser Glu Ser
        35                  40                  45

Thr Asp Glu Gln Ala Met Glu Asp Ile Lys Gln Met Glu Ala Glu Ser
    50                  55                  60

Ile Ser Ser Ser Glu Glu Ile Val Pro Asn Ser Val Glu Gln Lys His
65                  70                  75                  80
```

```
Ile Gln Lys Glu Asp Val Pro Ser Glu Arg Tyr Leu Gly Tyr Leu Glu
                 85                  90                  95

Gln Leu Leu Arg Leu Lys Lys Tyr Lys Val Pro Gln Leu Glu Ile Val
            100                 105                 110

Pro Asn Ser Ala Glu Glu Arg Leu His Ser Met Lys Glu Gly Ile His
            115                 120                 125

Ala Gln Gln Lys Glu Pro Met Ile Gly Val Asn Gln Glu Leu Ala Tyr
        130                 135                 140

Phe Tyr Pro Glu Leu Phe Arg Gln Phe Tyr Gln Leu Asp Ala Tyr Pro
145                 150                 155                 160

Ser Gly Ala Trp Tyr Tyr Val Pro Leu Gly Thr Gln Tyr Thr Asp Ala
                165                 170                 175

Pro Ser Phe Ser Asp Ile Pro Asn Pro Ile Gly Ser Glu Asn Ser Glu
            180                 185                 190

Lys Thr Thr Met Pro Leu Trp
        195
```

<210> SEQ ID NO 52
<211> LENGTH: 10
<212> TYPE: PRT
<213> ORGANISM: Artificial Sequence
<220> FEATURE:
<223> OTHER INFORMATION: synthetically prepared peptide sequence

<400> SEQUENCE: 52

```
Met Lys Glu Gly Ile His Ala Gln Gln Lys
1               5                   10
```

<210> SEQ ID NO 53
<211> LENGTH: 10
<212> TYPE: PRT
<213> ORGANISM: Artificial Sequence
<220> FEATURE:
<223> OTHER INFORMATION: synthetically prepared peptide sequence

<400> SEQUENCE: 53

```
Tyr Gln Lys Phe Ala Leu Pro Gln Tyr Leu
1               5                   10
```

<210> SEQ ID NO 54
<211> LENGTH: 10
<212> TYPE: PRT
<213> ORGANISM: Artificial Sequence
<220> FEATURE:
<223> OTHER INFORMATION: synthetically prepared peptide sequence

<400> SEQUENCE: 54

```
Lys Asp Glu Arg Phe Phe Ser Asp Lys Ile
1               5                   10
```

<210> SEQ ID NO 55
<211> LENGTH: 10
<212> TYPE: PRT
<213> ORGANISM: Artificial Sequence
<220> FEATURE:
<223> OTHER INFORMATION: synthetically prepared peptide sequence

<400> SEQUENCE: 55

```
Ser Pro Pro Glu Ile Asn Thr Val Gln Val
1               5                   10
```

<210> SEQ ID NO 56

-continued

<211> LENGTH: 28
<212> TYPE: PRT
<213> ORGANISM: Artificial Sequence
<220> FEATURE:
<223> OTHER INFORMATION: synthetically prepared peptide sequence

<400> SEQUENCE: 56

His Ser Asp Ala Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 57
<211> LENGTH: 29
<212> TYPE: PRT
<213> ORGANISM: Artificial Sequence
<220> FEATURE:
<223> OTHER INFORMATION: synthetically prepared peptide sequence

<400> SEQUENCE: 57

Tyr Ser Ala Asn Ser Asn Pro Ala Met Ala Pro Arg Glu Arg Lys Ala
 1               5                  10                  15

Gly Cys Lys Asn Phe Phe Trp Lys Thr Phe Thr Ser Cys
            20                  25

<210> SEQ ID NO 58
<211> LENGTH: 11
<212> TYPE: PRT
<213> ORGANISM: Artificial Sequence
<220> FEATURE:
<223> OTHER INFORMATION: synthetically prepared peptide sequence

<400> SEQUENCE: 58

Arg Gln Lys Pro Gln Gln Phe Phe Gly Leu Met
 1               5                  10

<210> SEQ ID NO 59
<211> LENGTH: 9
<212> TYPE: PRT
<213> ORGANISM: Artificial Sequence
<220> FEATURE:
<223> OTHER INFORMATION: synthetically prepared peptide sequence

<400> SEQUENCE: 59

Cys Tyr Lys Gln Asn Cys Pro Leu Gly
 1               5

<210> SEQ ID NO 60
<211> LENGTH: 36
<212> TYPE: PRT
<213> ORGANISM: Artificial Sequence
<220> FEATURE:
<223> OTHER INFORMATION: synthetically prepared peptide sequence

<400> SEQUENCE: 60

Ala Pro Leu Glu Pro Val Tyr Pro Gly Asp Asn Ala Thr Pro Glu Gln
 1               5                  10                  15

Met Ala Gln Tyr Ala Ala Asp Leu Arg Arg Tyr Ile Asn Met Leu Thr
            20                  25                  30

Arg Pro Arg Tyr
        35

<210> SEQ ID NO 61
<211> LENGTH: 17
<212> TYPE: PRT

<213> ORGANISM: Artificial Sequence
<220> FEATURE:
<223> OTHER INFORMATION: synthetically prepared peptide sequence

<400> SEQUENCE: 61

Glu Gly Pro Trp Leu Glu Glu Glu Glu Ala Tyr Gly Trp Met Asp
1               5                   10                  15

Phe

<210> SEQ ID NO 62
<211> LENGTH: 34
<212> TYPE: PRT
<213> ORGANISM: Artificial Sequence
<220> FEATURE:
<223> OTHER INFORMATION: synthetically prepared peptide sequence

<400> SEQUENCE: 62

Glu Leu Gly Pro Gln Gly Pro Pro His Leu Val Ala Asp Pro Ser Lys
1               5                   10                  15

Lys Gln Gly Pro Trp Leu Glu Glu Glu Glu Ala Tyr Gly Trp Met
            20                  25                  30

Asp Phe

<210> SEQ ID NO 63
<211> LENGTH: 27
<212> TYPE: PRT
<213> ORGANISM: Artificial Sequence
<220> FEATURE:
<223> OTHER INFORMATION: synthetically prepared peptide sequence

<400> SEQUENCE: 63

Val Pro Leu Pro Ala Gly Gly Gly Thr Val Leu Thr Lys Met Tyr Pro
1               5                   10                  15

Arg Gly Asn His Trp Ala Val Gly His Leu Met
            20                  25

<210> SEQ ID NO 64
<211> LENGTH: 6
<212> TYPE: PRT
<213> ORGANISM: Artificial Sequence
<220> FEATURE:
<223> OTHER INFORMATION: synthetically prepared peptide sequence

<400> SEQUENCE: 64

Tyr Gly Gly Phe Leu Met
1               5

<210> SEQ ID NO 65
<211> LENGTH: 31
<212> TYPE: PRT
<213> ORGANISM: Artificial Sequence
<220> FEATURE:
<223> OTHER INFORMATION: synthetically prepared peptide sequence

<400> SEQUENCE: 65

Tyr Gly Gly Phe Met Thr Ser Glu Lys Ser Gln Thr Pro Leu Val Thr
1               5                   10                  15

Leu Phe Lys Asn Ala Ile Ile Lys Asn Ala Tyr Lys Lys Gly Glu
            20                  25                  30

<210> SEQ ID NO 66
<211> LENGTH: 38
<212> TYPE: PRT
<213> ORGANISM: Artificial Sequence -continued

```
<220> FEATURE:
<223> OTHER INFORMATION: synthetically prepared peptide sequence

<400> SEQUENCE: 66

Cys Ser Cys Ser Ser Leu Met Asp Lys Glu Cys Val Tyr Phe Cys His
 1               5                  10                  15

Leu Asp Ile Ile Trp Val Asn Thr Pro Glu His Val Val Pro Tyr Gly
             20                  25                  30

Leu Gly Ser Pro Arg Ser
            35

<210> SEQ ID NO 67
<211> LENGTH: 17
<212> TYPE: PRT
<213> ORGANISM: Artificial Sequence
<220> FEATURE:
<223> OTHER INFORMATION: synthetically prepared peptide sequence

<400> SEQUENCE: 67

Tyr Gly Gly Phe Leu Arg Arg Ile Arg Pro Lys Leu Lys Trp Asp Asn
 1               5                  10                  15

Gln

<210> SEQ ID NO 68
<211> LENGTH: 13
<212> TYPE: PRT
<213> ORGANISM: Artificial Sequence
<220> FEATURE:
<223> OTHER INFORMATION: synthetically prepared peptide sequence

<400> SEQUENCE: 68

Tyr Gly Gly Phe Leu Arg Arg Gln Phe Lys Val Val Thr
 1               5                  10

<210> SEQ ID NO 69
<211> LENGTH: 22
<212> TYPE: PRT
<213> ORGANISM: Artificial Sequence
<220> FEATURE:
<223> OTHER INFORMATION: synthetically prepared peptide sequence

<400> SEQUENCE: 69

Met Pro His Leu Leu Ser Gly Phe Leu Glu Val Thr Ala Ser Pro Ala
 1               5                  10                  15

Pro Thr Trp Asp Ala Pro
            20

<210> SEQ ID NO 70
<211> LENGTH: 22
<212> TYPE: PRT
<213> ORGANISM: Artificial Sequence
<220> FEATURE:
<223> OTHER INFORMATION: synthetically prepared peptide sequence

<400> SEQUENCE: 70

Ile Phe Gly His Phe Phe Cys Asn Val Phe Ile Ala Met Asp Val Met
 1               5                  10                  15

Cys Cys Thr Ala Ser Ile
            20

<210> SEQ ID NO 71
<211> LENGTH: 22
<212> TYPE: PRT
<213> ORGANISM: Artificial Sequence
```

-continued

```
<220> FEATURE:
<223> OTHER INFORMATION: synthetically prepared peptide sequence

<400> SEQUENCE: 71

Leu Lys Leu Ala Glu Arg Pro Glu Arg Ser Glu Phe Val Leu Gln Asn
1               5                   10                  15

Ser Asp His Cys Gly Lys
            20

<210> SEQ ID NO 72
<211> LENGTH: 12
<212> TYPE: PRT
<213> ORGANISM: Artificial Sequence
<220> FEATURE:
<223> OTHER INFORMATION: synthetically prepared peptide sequence

<400> SEQUENCE: 72

Ser Phe Arg Pro Gly Ser Arg Gly Gly Ser Arg Gly
1               5                   10

<210> SEQ ID NO 73
<211> LENGTH: 22
<212> TYPE: PRT
<213> ORGANISM: Artificial Sequence
<220> FEATURE:
<223> OTHER INFORMATION: synthetically prepared peptide sequence

<400> SEQUENCE: 73

Glu Gln Phe Leu Asp Gly Asp Gly Trp Thr Ser Arg Trp Ile Glu Ser
1               5                   10                  15

Gly Leu Gln Thr Ser Gln
            20

<210> SEQ ID NO 74
<211> LENGTH: 22
<212> TYPE: PRT
<213> ORGANISM: Artificial Sequence
<220> FEATURE:
<223> OTHER INFORMATION: synthetically prepared peptide sequence

<400> SEQUENCE: 74

Phe Val Pro Ile Phe Thr Tyr Gly Glu Leu Gln Arg Met Gln Glu Lys
1               5                   10                  15

Glu Arg Asn Lys Gly Gln
            20

<210> SEQ ID NO 75
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 75

Leu Lys Gln Ile Ala Ala His Ala Gly Lys Glu Gly Ala Ile Ile Phe
1               5                   10                  15

Gln Gln Val Met
            20

<210> SEQ ID NO 76
<211> LENGTH: 20
<212> TYPE: PRT
<213> ORGANISM: Artificial Sequence
<220> FEATURE:
<223> OTHER INFORMATION: synthetically prepared peptide sequence
```

```
<400> SEQUENCE: 76

Met Leu Arg Leu Pro Thr Val Phe Arg Gln Met Arg Pro Val Ser Arg
 1               5                  10                  15

Val Leu Ala Pro
         20

<210> SEQ ID NO 77
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 77

Arg Val Leu Ala Pro His Leu Thr Arg Ala Tyr Ala Lys Asp Val Lys
 1               5                  10                  15

Phe Gly Ala Asp
         20

<210> SEQ ID NO 78
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 78

Lys Phe Gly Ala Asp Ala Arg Ala Leu Met Leu Gln Gly Val Asp Leu
 1               5                  10                  15

Leu Ala Asp Ala
         20

<210> SEQ ID NO 79
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 79

Leu Leu Ala Asp Ala Val Ala Val Thr Met Gly Pro Lys Gly Arg Thr
 1               5                  10                  15

Val Ile Ile Glu
         20

<210> SEQ ID NO 80
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 80

Thr Val Ile Ile Glu Gln Ser Trp Gly Ser Pro Lys Val Thr Lys Asp
 1               5                  10                  15

Gly Val Thr Val
         20

<210> SEQ ID NO 81
<211> LENGTH: 20
<212> TYPE: PRT
<213> ORGANISM: Artificial Sequence
<220> FEATURE:
```

<223> OTHER INFORMATION: synthetically prepared peptide sequence

<400> SEQUENCE: 81

Asp Gly Val Thr Val Ala Lys Ser Ile Asp Leu Lys Asp Lys Tyr Lys
1               5                   10                  15

Asn Ile Gly Ala
            20

<210> SEQ ID NO 82
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 82

Lys Asn Ile Gly Ala Lys Leu Val Gln Asp Val Ala Asn Asn Thr Asn
1               5                   10                  15

Glu Glu Ala Gly
            20

<210> SEQ ID NO 83
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 83

Asn Glu Glu Ala Gly Asp Gly Thr Thr Thr Ala Thr Val Leu Ala Arg
1               5                   10                  15

Ser Ile Ala Lys
            20

<210> SEQ ID NO 84
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 84

Arg Ser Ile Ala Lys Glu Gly Phe Glu Lys Ile Ser Lys Gly Ala Asn
1               5                   10                  15

Pro Val Glu Ile
            20

<210> SEQ ID NO 85
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 85

Asn Pro Val Glu Ile Arg Arg Gly Val Met Leu Ala Val Asp Ala Val
1               5                   10                  15

Ile Ala Glu Leu
            20

<210> SEQ ID NO 86
<211> LENGTH: 20
<212> TYPE: PRT
<213> ORGANISM: Artificial Sequence -continued

```
<220> FEATURE:
<223> OTHER INFORMATION: synthetically prepared peptide sequence

<400> SEQUENCE: 86

Val Ile Ala Glu Leu Lys Lys Gln Ser Lys Pro Val Thr Thr Pro Glu
1               5                   10                  15

Glu Ile Ala Gln
            20

<210> SEQ ID NO 87
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 87

Glu Glu Ile Ala Gln Val Ala Thr Ile Ser Ala Asn Gly Asp Lys Glu
1               5                   10                  15

Ile Gly Asn Ile
            20

<210> SEQ ID NO 88
<211> LENGTH: 19
<212> TYPE: PRT
<213> ORGANISM: Artificial Sequence
<220> FEATURE:
<223> OTHER INFORMATION: synthetically prepared peptide sequence

<400> SEQUENCE: 88

Glu Ile Gly Asn Ile Ile Ser Asp Ala Met Lys Lys Val Gly Arg Lys
1               5                   10                  15

Gly Val Ile

<210> SEQ ID NO 89
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 89

Arg Lys Gly Val Ile Thr Val Lys Asp Gly Lys Thr Leu Asn Asp Glu
1               5                   10                  15

Leu Glu Ile Ile
            20

<210> SEQ ID NO 90
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 90

Glu Leu Glu Ile Ile Glu Gly Met Lys Phe Asp Arg Gly Tyr Ile Ser
1               5                   10                  15

Pro Tyr Phe Ile
            20

<210> SEQ ID NO 91
<211> LENGTH: 20
<212> TYPE: PRT
<213> ORGANISM: Artificial Sequence
```

```
<220> FEATURE:
<223> OTHER INFORMATION: synthetically prepared peptide sequence

<400> SEQUENCE: 91

Ser Pro Tyr Phe Ile Asn Thr Ser Lys Gly Gln Lys Cys Glu Phe Gln
1               5                   10                  15

Asp Ala Tyr Val
            20

<210> SEQ ID NO 92
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 92

Gln Asp Ala Tyr Val Leu Leu Ser Glu Lys Lys Ile Ser Ser Ile Gln
1               5                   10                  15

Ser Ile Val Pro
            20

<210> SEQ ID NO 93
<211> LENGTH: 21
<212> TYPE: PRT
<213> ORGANISM: Artificial Sequence
<220> FEATURE:
<223> OTHER INFORMATION: synthetically prepared peptide sequence

<400> SEQUENCE: 93

Gln Ser Ile Val Pro Ala Leu Glu Ile Ala Asn Ala His Arg Lys Pro
1               5                   10                  15

Leu Val Ile Ile Ala
            20

<210> SEQ ID NO 94
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 94

Leu Val Ile Ile Ala Glu Asp Val Asp Gly Glu Ala Leu Ser Thr Leu
1               5                   10                  15

Val Leu Asn Arg
            20

<210> SEQ ID NO 95
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 95

Leu Val Leu Asn Arg Leu Lys Val Gly Leu Gln Val Val Ala Val Lys
1               5                   10                  15

Ala Pro Gly Phe
            20

<210> SEQ ID NO 96
<211> LENGTH: 20
<212> TYPE: PRT
```

```
<213> ORGANISM: Artificial Sequence
<220> FEATURE:
<223> OTHER INFORMATION: synthetically prepared peptide sequence

<400> SEQUENCE: 96

Lys Ala Pro Gly Phe Gly Asp Asn Arg Lys Asn Gln Leu Lys Asp Met
 1               5                  10                  15

Ala Ile Ala Thr
            20

<210> SEQ ID NO 97
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 97

Met Ala Ile Ala Thr Gly Gly Ala Val Phe Gly Glu Glu Gly Leu Thr
 1               5                  10                  15

Leu Asn Leu Glu
            20

<210> SEQ ID NO 98
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 98

Thr Leu Asn Leu Glu Asp Val Gln Pro His Asp Leu Gly Lys Val Gly
 1               5                  10                  15

Glu Val Ile Val
            20

<210> SEQ ID NO 99
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 99

Gly Glu Val Ile Val Thr Lys Asp Asp Ala Met Leu Leu Lys Gly Lys
 1               5                  10                  15

Gly Asp Lys Ala
            20

<210> SEQ ID NO 100
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 100

Lys Gly Asp Lys Ala Gln Ile Glu Lys Arg Ile Gln Glu Ile Ile Glu
 1               5                  10                  15

Gln Leu Asp Val
            20

<210> SEQ ID NO 101
<211> LENGTH: 20
```

```
<212> TYPE: PRT
<213> ORGANISM: Artificial Sequence
<220> FEATURE:
<223> OTHER INFORMATION: synthetically prepared peptide sequence

<400> SEQUENCE: 101

Glu Gln Leu Asp Val Thr Thr Ser Glu Tyr Glu Lys Glu Lys Leu Asn
1               5                   10                  15

Glu Arg Leu Ala
            20

<210> SEQ ID NO 102
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 102

Asn Glu Arg Leu Ala Lys Leu Ser Asp Gly Val Ala Val Leu Lys Val
1               5                   10                  15

Gly Gly Thr Ser
            20

<210> SEQ ID NO 103
<211> LENGTH: 19
<212> TYPE: PRT
<213> ORGANISM: Artificial Sequence
<220> FEATURE:
<223> OTHER INFORMATION: synthetically prepared peptide sequence

<400> SEQUENCE: 103

Val Gly Gly Thr Asp Val Glu Val Asn Glu Lys Lys Asp Arg Val Thr
1               5                   10                  15

Asp Ala Leu

<210> SEQ ID NO 104
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 104

Val Thr Asp Ala Leu Asn Ala Thr Arg Ala Ala Val Glu Glu Gly Ile
1               5                   10                  15

Val Leu Gly Gly
            20

<210> SEQ ID NO 105
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 105

Ile Val Leu Gly Gly Gly Cys Ala Leu Leu Arg Cys Ile Pro Ala Leu
1               5                   10                  15

Asp Ser Leu Thr
            20

<210> SEQ ID NO 106
<211> LENGTH: 20
```

-continued

```
<212> TYPE: PRT
<213> ORGANISM: Artificial Sequence
<220> FEATURE:
<223> OTHER INFORMATION: synthetically prepared peptide sequence

<400> SEQUENCE: 106

Leu Asp Ser Leu Thr Pro Ala Asn Glu Asp Gln Lys Ile Gly Ile Glu
1               5                   10                  15

Ile Ile Lys Arg
            20

<210> SEQ ID NO 107
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 107

Glu Ile Ile Lys Arg Thr Leu Lys Ile Pro Ala Met Thr Ile Ala Lys
1               5                   10                  15

Asn Ala Gly Val
            20

<210> SEQ ID NO 108
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 108

Lys Asn Ala Gly Val Glu Gly Ser Leu Ile Val Glu Lys Ile Met Gln
1               5                   10                  15

Ser Ser Ser Glu
            20

<210> SEQ ID NO 109
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 109

Gln Ser Ser Ser Glu Val Gly Tyr Asp Ala Met Ala Gly Asp Phe Val
1               5                   10                  15

Asn Met Val Glu
            20

<210> SEQ ID NO 110
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 110

Val Asn Met Val Glu Lys Gly Ile Ile Asp Pro Thr Lys Val Val Arg
1               5                   10                  15

Thr Ala Leu Leu
            20

<210> SEQ ID NO 111
```

-continued

```
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 111

Arg Thr Ala Leu Leu Asp Ala Ala Gly Val Ala Ser Leu Leu Thr Thr
 1               5                  10                  15

Ala Glu Val Val
         20

<210> SEQ ID NO 112
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 112

Thr Ala Glu Val Val Val Thr Glu Ile Pro Lys Glu Lys Asp Pro
 1               5                  10                  15

Gly Met Gly Ala
         20

<210> SEQ ID NO 113
<211> LENGTH: 18
<212> TYPE: PRT
<213> ORGANISM: Artificial Sequence
<220> FEATURE:
<223> OTHER INFORMATION: synthetically prepared peptide sequence

<400> SEQUENCE: 113

Pro Gly Met Gly Ala Met Gly Gly Met Gly Gly Met Gly Gly
 1               5                  10                  15

Met Phe

<210> SEQ ID NO 114
<211> LENGTH: 24
<212> TYPE: PRT
<213> ORGANISM: Artificial Sequence
<220> FEATURE:
<223> OTHER INFORMATION: synthetically prepared peptide sequence

<400> SEQUENCE: 114

Val Leu Gly Gly Gly Val Leu Leu Arg Val Ile Pro Ala Leu Asp
 1               5                  10                  15

Ser Leu Thr Pro Ala Asn Glu Asp
         20

<210> SEQ ID NO 115
<211> LENGTH: 30
<212> TYPE: PRT
<213> ORGANISM: Artificial Sequence
<220> FEATURE:
<223> OTHER INFORMATION: synthetically prepared peptide sequence

<400> SEQUENCE: 115

Met Lys Thr Pro Trp Arg Val Leu Leu Gly Leu Leu Gly Ala Ala Ala
 1               5                  10                  15

Leu Val Thr Ile Ile Thr Val Pro Val Val Leu Leu Asn Lys
         20                  25                  30

<210> SEQ ID NO 116
```

```
<211> LENGTH: 21
<212> TYPE: PRT
<213> ORGANISM: Artificial Sequence
<220> FEATURE:
<223> OTHER INFORMATION: synthetically prepared peptide sequence

<400> SEQUENCE: 116

Met Ala Glu Tyr Gly Asn Ser Ser Val Phe Leu Glu Asn Ser Thr Phe
1               5                   10                  15

Asp Glu Phe Gly His
            20

<210> SEQ ID NO 117
<211> LENGTH: 21
<212> TYPE: PRT
<213> ORGANISM: Artificial Sequence
<220> FEATURE:
<223> OTHER INFORMATION: synthetically prepared peptide sequence

<400> SEQUENCE: 117

Lys Arg Gln Leu Ile Thr Glu Glu Arg Ile Pro Asn Asn Thr Gln Trp
1               5                   10                  15

Val Thr Trp Ser Pro
            20

<210> SEQ ID NO 118
<211> LENGTH: 21
<212> TYPE: PRT
<213> ORGANISM: Artificial Sequence
<220> FEATURE:
<223> OTHER INFORMATION: synthetically prepared peptide sequence

<400> SEQUENCE: 118

Asn Gly Thr Phe Leu Ala Tyr Ala Gln Phe Asn Asp Thr Glu Val Pro
1               5                   10                  15

Leu Ile Glu Tyr Ser
            20

<210> SEQ ID NO 119
<211> LENGTH: 21
<212> TYPE: PRT
<213> ORGANISM: Artificial Sequence
<220> FEATURE:
<223> OTHER INFORMATION: synthetically prepared peptide sequence

<400> SEQUENCE: 119

Val Thr Asn Ala Thr Ser Ile Gln Ile Thr Ala Pro Ala Ser Met Leu
1               5                   10                  15

Ile Gly Asp His Tyr
            20

<210> SEQ ID NO 120
<211> LENGTH: 21
<212> TYPE: PRT
<213> ORGANISM: Artificial Sequence
<220> FEATURE:
<223> OTHER INFORMATION: synthetically prepared peptide sequence

<400> SEQUENCE: 120

Ile Gln Asn Tyr Ser Val Met Asp Ile Cys Asp Tyr Asp Glu Ser Ser
1               5                   10                  15

Gly Arg Trp Asn Cys
            20
```

```
<210> SEQ ID NO 121
<211> LENGTH: 21
<212> TYPE: PRT
<213> ORGANISM: Artificial Sequence
<220> FEATURE:
<223> OTHER INFORMATION: synthetically prepared peptide sequence

<400> SEQUENCE: 121

Asn Ser Phe Tyr Lys Ile Ile Ser Asn Glu Glu Gly Tyr Arg His Ile
 1               5                  10                  15

Cys Tyr Phe Gln Ile
            20

<210> SEQ ID NO 122
<211> LENGTH: 21
<212> TYPE: PRT
<213> ORGANISM: Artificial Sequence
<220> FEATURE:
<223> OTHER INFORMATION: synthetically prepared peptide sequence

<400> SEQUENCE: 122

Asn Val Gln Met Pro Ser Lys Lys Leu Asp Phe Ile Ile Leu Asn Glu
 1               5                  10                  15

Thr Lys Phe Trp Tyr
            20

<210> SEQ ID NO 123
<211> LENGTH: 21
<212> TYPE: PRT
<213> ORGANISM: Artificial Sequence
<220> FEATURE:
<223> OTHER INFORMATION: synthetically prepared peptide sequence

<400> SEQUENCE: 123

Pro Glu Asp Asn Leu Asp His Tyr Arg Asn Ser Thr Val Met Ser Arg
 1               5                  10                  15

Ala Glu Asn Phe Lys
            20

<210> SEQ ID NO 124
<211> LENGTH: 21
<212> TYPE: PRT
<213> ORGANISM: Artificial Sequence
<220> FEATURE:
<223> OTHER INFORMATION: synthetically prepared peptide sequence

<400> SEQUENCE: 124

Thr Ala His Gln His Ile Tyr Thr His Met Ser His Phe Ile Lys Gln
 1               5                  10                  15

Cys Phe Ser Leu Pro
            20

<210> SEQ ID NO 125
<211> LENGTH: 19
<212> TYPE: PRT
<213> ORGANISM: Artificial Sequence
<220> FEATURE:
<223> OTHER INFORMATION: synthetically prepared peptide sequence

<400> SEQUENCE: 125

Gln Gln Leu Pro Gln Pro Gln Gln Pro Gln Ser Phe Pro Gln Gln
 1               5                  10                  15

Gln Pro Phe
```

```
<210> SEQ ID NO 126
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 126

Leu Gln Leu Gln Pro Phe Pro Gln Pro Gln Leu Pro Tyr Pro Gln Pro
 1               5                  10                  15

Gln Leu Pro Tyr
            20

<210> SEQ ID NO 127
<211> LENGTH: 12
<212> TYPE: PRT
<213> ORGANISM: Artificial Sequence
<220> FEATURE:
<223> OTHER INFORMATION: synthetically prepared peptide sequence

<400> SEQUENCE: 127

Pro Gln Pro Leu Pro Tyr Pro Gln Pro Gln Pro Phe
 1               5                  10

<210> SEQ ID NO 128
<211> LENGTH: 28
<212> TYPE: PRT
<213> ORGANISM: Artificial Sequence
<220> FEATURE:
<221> NAME/KEY: VARIANT
<222> LOCATION: 15
<223> OTHER INFORMATION: Xaa- Any Amino Acid
<220> FEATURE:
<223> OTHER INFORMATION: Synthetically prepared peptide sequence

<400> SEQUENCE: 128

Gln Gln Pro Gln Gln Phe Glx Pro Gln Gln Pro Tyr Pro Glx Xaa Glx
 1               5                  10                  15

Pro Glx Leu Gly Glx Glx Glx Pro Phe Pro Pro Glx
            20                  25

<210> SEQ ID NO 129
<211> LENGTH: 18
<212> TYPE: PRT
<213> ORGANISM: Artificial Sequence
<220> FEATURE:
<223> OTHER INFORMATION: synthetically prepared peptide sequence

<400> SEQUENCE: 129

Glx Gly Glx Pro Gly Tyr Tyr Pro Thr Ser Pro Glx Glx Pro Gly Gln
 1               5                  10                  15

Glu Gln

<210> SEQ ID NO 130
<211> LENGTH: 18
<212> TYPE: PRT
<213> ORGANISM: Artificial Sequence
<220> FEATURE:
<223> OTHER INFORMATION: synthetically prepared peptide sequence

<400> SEQUENCE: 130

Glx Thr Glx Ser Leu Val Tyr Pro Phe Pro Gly Pro Ile Pro Asn Ser
 1               5                  10                  15

Leu Pro
```

```
<210> SEQ ID NO 131
<211> LENGTH: 19
<212> TYPE: PRT
<213> ORGANISM: Artificial Sequence
<220> FEATURE:
<223> OTHER INFORMATION: synthetically prepared peptide sequence

<400> SEQUENCE: 131

Leu His Leu Pro Leu Pro Leu Leu Glx Ser Trp Met His Glx Pro His
 1               5                  10                  15

Glx Pro Leu

<210> SEQ ID NO 132
<211> LENGTH: 16
<212> TYPE: PRT
<213> ORGANISM: Artificial Sequence
<220> FEATURE:
<223> OTHER INFORMATION: synthetically prepared peptide sequence

<400> SEQUENCE: 132

Met Glu Cys Glu Lys Asn Leu Tyr Trp Ile Cys Asn Lys Pro Tyr Lys
 1               5                  10                  15

<210> SEQ ID NO 133
<211> LENGTH: 20
<212> TYPE: PRT
<213> ORGANISM: Artificial Sequence
<220> FEATURE:
<223> OTHER INFORMATION: synthetically prepared peptide sequence

<400> SEQUENCE: 133

Leu Lys Gln Ile Ala Ala His Ala Gly Lys Glu Gly Ala Ile Ile Phe
 1               5                  10                  15

Gln Gln Val Met
            20
```

IDENTIFICATION OF ETIOLOGY OF AUTISM

BACKGROUND OF THE INVENTION

1. Field of the Invention

The invention relates to identification of etiology of autism.

2. Description of the Related Art

Autism is a developmental disorder, which manifests itself during early childhood. In the autistic child, communications and social interactions, are severely impaired. Unable to learn from the natural environment as most children do, the child with autism generally shows little interest in the world or people around him. Although some children with autism develop normally and even acquire advanced skills, most exhibit a wide range of behavioral problems. In reality, autism affects the way a person comprehends, communicates and relates to others. Autism was originally thought to be primarily a psychiatric condition. However, further investigation showed that genetic and environmental factors are implicated in the pathogenesis of autism (1-8). The effects of environmental factors such as infections and toxic chemicals on gene expression result in biochemical, immunological and neurological disorders found in children with autism.

Diagnosis of Autism

Because we have no definitive diagnostic tests for the biological manifestations of autism, it remains one of the only neurological disorders that must be diagnosed almost entirely through behavioral symptoms. We know that autism interferes with the normal development of the brain in the areas of reasoning, social interaction, communication skills and emotions such as love and empathy. Children and adults with autism typically have deficiencies in verbal and non-verbal communication, social interactions, and leisure or play activities. Autistic people may exhibit repeated body movements such as hand flapping, rocking, or spinning; they may have unusual responses to people or attachments to objects; and they may resist changes in routines. In some cases they may exhibit aggressive or self-injurious behavior.

According to the DSM-IV or *Diagnosis and Statistical Manual for Mental Disorders*, 4t' edition, published by the American Psychiatric Association (9), autism is classified as a Pervasive Developmental Disorder (PDD) characterized by twelve diagnostic criteria. These criteria fall into three categories—impairments in social interaction, impairments in communication, and a restricted repertoire of activities and interests. A diagnosis of autism requires that a child display at least six of these twelve symptoms, with a minimum number in each category.

DSM IV Diagnostic Criteria for Autism

Diagnosis Criteria for 299.00 Autistic Disorder

A. A total of six (or more) items from (1), (2), and (3), with at least two from (1), and one each from (2) and (3):

1. qualitative impairment in social interaction, as manifested by at least two of the following:
   a. marked impairment in the use of multiple nonverbal behaviors such as eye-to-eye gaze, facial expression, body postures, and gestures to regulate social interaction
   b. failure to develop peer relationships appropriate to developmental level
   c. lack of spontaneous seeking to share enjoyment, interests, or achievements with other people (e.g., by a lack of showing, bringing, or pointing out objects of interest)
   d. lack of social or emotional reciprocity
2. qualitative impairments in communication as manifested by at least one of the following:
   a. delay in, or total lack of, the development of spoken language (not accompanied by an attempt to compensate through alternative modes of communication such as gesture or mime)
   b. in individuals with adequate speech, marked impairment in the ability to initiate or sustain a conversation with others
   c. stereotyped and repetitive use of language or idiosyncratic language
   d. lack of varied, spontaneous make-believe play or social imitative play appropriate to developmental level
3. restricted repetitive and stereotyped patterns of behavior, interests and activities, as manifested by at least one of the following:
   a. encompassing preoccupation with one or more stereotyped and restricted patterns of interest that is abnormal either in intensity or focus
   b. apparently inflexible adherence to specific, nonfunctional routines or rituals
   c. stereotyped and repetitive motor mannerisms (e.g., hand or finger flapping or twisting, or complex whole-body movements)
   d. persistent preoccupation with parts of objects B. Delays or abnormal functioning in at least one of the following areas, with onset prior to age 3 years: (1) social interaction, (2) language as used in social communication, or (3) symbolic or imaginative play.

C. The disturbance is not better accounted for by Rett's Disorder or Childhood Disintegrative Disorder.

If a child does not fit the definition of autism given above, he or she may be diagnosed with a condition called Pervasive Developmental Disorder Not Otherwise Specified (PDD-NOS). Such a diagnosis of non-specific forms of Pervasive Developmental Disorder (PDD) may include atypical types of autism that do not fall into the above categories because of late age of onset, for example, or subthreshold or atypical symptoms. According to the DSM-IV, this diagnosis is to be used when autistic-like behaviors are present—in particular, when there is severe impairment in the development of social and verbal communication skills—but the child does not meet the criteria for classic autism or any other specific Pervasive Developmental Disorder, Schizophrenia, Schizotypal Personality Disorder or Avoidant Personality Disorder (9).

SUMMARY OF THE INVENTION

An embodiment provides for a method for determining etiology of an autistic spectrum disorder in a patient, comprising the steps of:

a) determining a level of at least one infectious agent derived antigen or antibody against an infectious agent derived antigen, at least one toxic chemical derived antigen or an antibody against a toxic chemical, and at least one dietary protein derived antigen or antibody against a dietary protein, in one or more samples from the patient;

b) comparing the level of antigens and/or antibodies determined in step a) with a normal level of the antigens and/or antibodies from control subjects, wherein
  (i) normal level or lower than normal level of antigens and/or antibodies for the each of said antigens indicate absence of an etiology of autistic spectrum disorder from presence of said antigens; and
  (ii) higher than normal level of antigens and/or antibodies for one or more of said antigens and/or antibodies indicates a likelihood of the autistic spectrum disorder being based on the presence of said antigens.

Another embodiment provides for a method for determining etiology of an autistic spectrum disorder in a patient, comprising the steps of:
a) determining a level of antibodies to a self-tissue or peptide in one or more samples from the patient; and
b) comparing the level of antibodies determined in step a) with a normal level of the antibodies from control subjects, wherein
  (i) normal level or lower than normal levels of antibodies indicate absence of etiology of autistic spectrum disorder from presence of said antibodies; and
  (ii) higher than normal level of the antibodies indicates a likelihood of the autistic spectrum disorder being based on the presence of said antibodies.

BRIEF DESCRIPTION OF THE DRAWINGS

FIG. 5 shows human (SEQ ID NO:1), rat (SEQ ID NO:2), and mouse (SEQ ID NO:3) sequences for Dipeptidyl Peptidase IV during intestinal differentiation which is also useful in assays of preferred embodiments.

DETAILED DESCRIPTION OF THE PREFERRED EMBODIMENT

Figure 1:
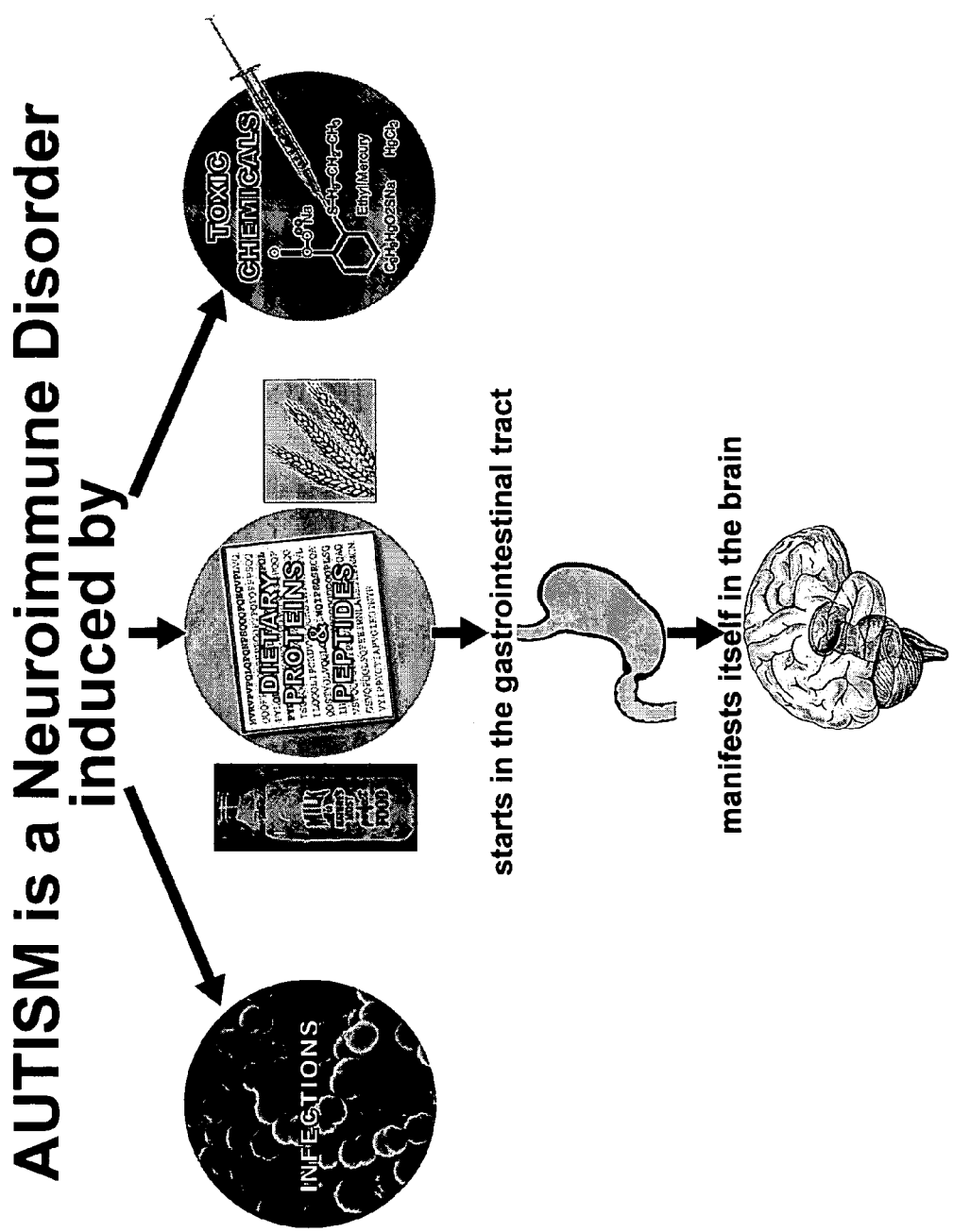
FIG. 1 illustrates induction of neuroimmune disorders by infections, toxic chemicals, and dietary proteins or peptides in autism.

Similar to many complex diseases (10), genetic and environmental factors including infections, xenobiotics, dietary proteins and peptides, play a role in the development of autism. The effects of environmental factors on genetic makeup can result in immune, gastrointestinal, neurological, biochemical and neuroimmunological abnormalities. Based on extensive research (11-15), we postulated that autism is induced by infectious agent antigens, toxic chemicals or dietary proteins. This process begins in the gastrointestinal tract but manifests itself in the brain (FIG. 1). These factors will be explained in detail in the following sections.

An embodiment provides for a method for determining etiology of an autistic spectrum disorder in a patient, comprising the steps of:
  a) determining a level of at least one infectious agent derived antigen or antibody against an infectious agent derived antigen, at least one toxic chemical derived antigen or an antibody against a toxic chemical, and at least one dietary protein derived antigen or antibody against a dietary protein, in one or more samples from the patient;
  b) comparing the level of antigens and/or antibodies determined in step a) with a normal level of the antigens and/or antibodies from control subjects, wherein
    (i) normal level or lower than normal level of antigens and/or antibodies for the each of said antigens indicate absence of an etiology of autistic spectrum disorder from presence of said antigens; and
    (iii) higher than normal level of antigens and/or antibodies for one or more of said antigens and/or antibodies indicates a likelihood of the autistic spectrum disorder being based on the presence of said antigens.

Another embodiment provides for a method for determining etiology of an autistic spectrum disorder in a patient, comprising the steps of:
  a) determining a level of antibodies to a self-tissue or peptide in one or more samples from the patient; and
  b) comparing the level of antibodies determined in step a) with a normal level of the antibodies from control subjects, wherein
    (i) normal level or lower than normal levels of antibodies indicate absence of etiology of autistic spectrum disorder from presence of said antibodies; and
    (ii) higher than normal level of the antibodies indicates a likelihood of the autistic spectrum disorder being based on the presence of said antibodies. Preferably, the higher than normal level of antibodies is calculated by taking a mean of levels of antibodies in individuals without symptoms relating to autistic spectrum disorder. Preferably, the higher than normal levels of antibodies is higher than about two standard deviations of normal level of antibodies of a control group.

Preferably, the determining the level of antibodies is accomplished using an immunoassay, such as ELISA, RAST, dot blot, Western blot, and ELISPOT. Preferably, the antibodies used in the immunoassay is selected from IgG, IgA, or IgM.

As used herein, "autistic spectrum disorder" refers to a developmental disorder that affects many aspects of a child's functioning. Autistic spectrum disorder can include, but is not limited to, autism, pervasive developmental disorder, and Asperger's Syndrome. Autistic spectrum disorder can occur in combination with other disorders, such as Attention Deficit Hyperactivity Disorder (ADHD) (which is part of the pervasive developmental disorder), learning disabilities (LD), anxiety disorders, obsessive-compulsive disorders (OCD), epilepsy, or mental retardation.

As used herein, "derived" or "derivative" refers to anything obtained or deduced from another.

The Role of Infectious Agents in Autism

Many infectious agents, including *Streptococcus*, measles, Rubella, Cytomegalovirus, Varicella zoster, Herpes type-6 and others have long been suspected as etiologic factors in autism (2-4, 16-18). Maternal or post-maternal exposure to these infectious agents may result in neurological disorders including autism. Using the observation that maternal infection increases the risk of schizophrenia anal autism in offspring, recently it has been shown that respiratory infection of pregnant mice (both BALB/c and C57BL/6 strains) with the human influenza virus resulted in offspring that displayed highly abnormal behavioral responses as adults. As in schizophrenia and autism, the offspring displayed deficits in prepulse inhibition (PPI) in the acoustic startle response. Compared with control mice, the infected mice also showed striking responses to the acute administration of antipsychotic and psychomimetic drugs. Moreover, these mice were deficient in exploratory behavior in both open-field and novel-object tests, and they were deficient in social interaction. At least some of these behavioral changes were likely attributable to the maternal immune response itself. They concluded that abnormal levels of cytokine production, which interfere with neuroimmuno-communications, are responsible for abnormal development of the brain (19-20).

Another explanation for disease development postulates that specific antigenic epitopes from an unspecified infectious agent or agents induce(s) a host immune response in which cross-reactivity with myelin triggers disease, a concept referred to as molecular mimicry. In this scenario, certain T-cells and/or antibodies elicited in response to antigens of the infectious agent also recognize relevant self-antigens in the CNS, thereby initiating the destructive autoimmune process (11-15, 21-27).

Infectious Agents and Response to Vaccinations

Many infectious agents, including measles, rubella virus and Cytomegalovirus, Herpes Type-6 and anaerobe bacteria such as *Clostridum difficile* have been implicated in autism. Therefore, the detection of nucleic acids and antibodies in blood may indicate ongoing infection and justify treatment with anti-bacterial or anti-viral agents (77-80). Moreover, measurements of antibodies against measles, mumps, rubella (MMR), diphtheria, pertusis, tetanus (DPT) and Hepatitis B will assess immune response to immunization and production of protective antibodies. Moderate elevation in IgG antibody against the components of MMR, DPT and Hepatitis B vaccines indicate optimal immune response and good immunological memory to these bacterial and viral antigens. High or very high levels of IgG antibodies against antigenic components of the vaccines indicate overactive immune response against them. Low levels or absence of IgG antibodies against components of vaccines may indicate lack of immunological memory and possibly immune deficiency in the immunized individual.

Examples of antibodies associated with infectious agents and response to vaccinations to be tested include, but are not limited to, measles, mumps, rubella, diphtheria toxoid, pertussis, tetanus toxoid, hepatitis B, herpes type 6, and clostridium neurotoxin.

The Role of Heavy Metals and Other Toxic Chemicals in Autism

Xenobiotics or toxic chemicals have been suspected to contribute to the induction of autoimmunity (30-34). Many environmental chemicals or drugs are toxic to hosts, and their detoxification is achieved primarily in the liver. During their metabolism, they may form reactive metabolites, which can then modify cellular proteins to form neoantigens. The precise mechanisms that lead to modification of self-proteins and the molecular requirements for this modified self to induce tolerance breakdown remain to be established. However, it is important to note that the direct toxic effect of xenobiotics is usually dose dependent and may be evident in the majority of individuals shortly after drug intake; hence, they are relatively easy to identify. In contrast, the immune-mediated effects that follow the intake of drugs or xenobiotics may take a prolonged period of time to be clinically manifest, making the identification of the causative agents a formidable task (35).

Edelson and Cantor (5, 36) demonstrated that neurotoxicants play a possible role in more than 90% of autistic children. These authors presented evidence for genetic and environmental aspects of a proposed process involving immune system injury and autoimmune responses secondary to exposure to immunotoxins. They believe that activation of the immune system is caused by toxicants leading to the production of autoantibodies against haptens, i.e., the toxic chemicals attached to brain proteins. The subsequent damage may be considered a component in the etiologic process of neurotoxicity in the autistic spectrum.

For a chemical compound to lead to an autoimmune response, it is generally thought that the compound must first become covalently bound to a carrier protein (37, 39). Immune reactions to drugs or their metabolites can develop when a hapten carrier complex interacts with gut-associated lymphoid tissues (GALT) that constitute the largest lymphoid organ (38). If covalent adducts of drugs or other chemical compounds are formed in GALT, it seems reasonable that they may lead to immune responses and chemically-induced Type I- Type IV allergic reactions (37). In fact, the non-steroidal anti-inflammatory Dicoflenac has been shown to cause a variety of idiosyncratic adverse reactions such as hemolytic anemia, hepatotoxicity, agranulocytosis, and anaphylaxis, all of which are components of immune reactions to protein adducts of Diclofenac (37-39). These protein adducts can be formed by direct reaction with tissue antigens or cytochrome P450 dependent and UDP-glucuronosyltransferase dependent pathways of metabolism. For example, immunoblot analysis of small intestine homogenates and isolated enterocytes with drug-specific antiserum revealed protein adducts of diclofenac. Two of these adducts of Diclofenac were identified as aminopeptidase N (CD 13) and sucrase-isomaltase (38). Intestinal protein adducts of chemicals can, therefore, be formed in GALT where they may lead to allergic reactions, inflammation and autoimmunity.

Among many toxicants, such as thimerosal, merthiolate, ethyl mercury, or other mercury-based compounds, in vaccines has been associated with immune injuries described in children with autism (41-44). Contrary to many haptens that bind covalently to a single amino acid, such as lysine, metal complexes consist of a central metal ion composed of four different amino acids, and hence they possess increased complex stability (37). To demonstrate possible binding of ethyl mercury to DPP IV and CD69, we postulated that in addition to infectious agent antigens such as Streptokinase, ethyl mercury (xenobiotic) binds to different lymphocyte receptors and tissue antigens. We assessed this hypothesis first by measuring IgG, IgM and IgA antibodies against CD26, CD69 and SK against ethyl mercury bound to human serum albumin in patients with autism. A significant percentage of children with autism developed anti-SK, and anti-ethyl mercury antibodies, concomitant with the appearance of anti-CD26 and anti-CD69 autoantibodies. These antibodies are synthesized as a result of SK and ethyl mercury binding to CD26 and CD69, indicating that they are specific. Immune absorption demonstrated that only specific antigens, like CD26, were capable of significantly reducing serum anti-CD26 levels. However, for direct demonstration of SK and ethyl mercury binding to CD26 or CD69, microtiter wells were coated with CD26 or CD69 alone or in combination with SK or ethyl mercury and then reacted with enzyme labeled rabbit anti-CD26 or anti-CD69. Adding these molecules to cD26 or CD69 resulted in 28-86% inhibition of CD26 or CD69 binding to anti-CD26 or anti-CD69 antibodies. We, therefore, propose that bacterial antigens and thimerosal (ethyl mercury) in individuals with pre-disposing HLA molecules, bind to CD26 or CD69 and induce antibodies against these molecules as well as to lymphocyte receptors and tissue antigens, resulting in autoimmune reaction in children with autism.

Neuroimmune Abnormalities Induced by Xenobiotics and Metals

It is of considerable interest that antibodies to neuron-specific antigens are prevalent in populations exposed to environmental and occupational chemicals and in patients with neurodegenerative diseases in which viruses or other infectious agents are the suspected etiological agents. For example, IgG antibodies to MBP, neuronal cytoskeletal proteins and neurofilaments are detected in workers exposed to lead or mercury (45). The titer of these antibodies is significantly correlated with blood lead or urinary mercury, which are the typical indices of exposure. Moreover, the level of these antibodies is correlated with the degree of sensorimotor deficits, because these antibodies interfere with neuromuscular function (46).

Taking into consideration the regulatory interactions between the nervous system and the immune system, as well as the detection of MBP and NAFP autoantibodies, it is therefore quite plausible to propose that drugs and environmental toxins might have detrimental effects on neuroendocrine-immune circuits, thereby resulting in autism. Toxic chemical exposure to substances, such as polychlorinated biphenyl, mercury, lead and other similar potentially harmful agents may induce alteration or over-expression of the genes involved in regional brain glial fibrillary acidic protein (GFAP) and astroglial glucose regulated protein (GRP). The astroglial cytoskeletal element GFAP, neurotypic and gliotypic proteins or neurofilament triplet are generally accepted as sensitive indicators of neurotoxic effects in mature brains (47, 48).

Over-expression of the gene results in altering the structural differentiation of astrocytes and the subsequent autoimmune response to neurofilaments and astroglial glucose regulated proteins. Autoantibodies against neurological antigens in autism have been studied in our laboratory extensively and found to be elevated in children with autism (11-15). The high prevalence of these autoantibodies in neurodegenerative and neuropsychiatric disorders has led many investigators to believe that these antibodies reflect an alteration of the blood-brain barrier, which promotes the access of immunocompetent cells to the central nervous system (49-52).

In these studies, we were able to present viable evidence in support of the genetic and environmental aspects of a hypothetical process believed to cause immune system injury secondary to immunotoxins exposure. Activation of the immune system is caused by toxicants, leading to the production of autoantibodies against haptens—the toxic chemicals attached to brain proteins. The resulting damage may be considered a component in the etiologic process of neurotoxicity in the autistic spectrum.

Autoimmune Reaction Induced by Heavy Metals

Mercury is a widely distributed environmental and industrial pollutant. This is why methyl mercury is often detected in many fish. In fact, ethyl-mercury or thimerosal has been used in increasing amounts as preservatives in many vaccines since the 1950's. Therefore, during the first year of life when the immune system is in the process of maturation, children become exposed to up to 100 micrograms of mercury, which greatly exceeds the CDC threshold. Exposure to large doses of mercury results in acute renal tubular lesions and immunosuppression, whereas chronic administration of smaller doses can lead to development of systemic autoimmunity (31-34). The characteristic features of mercury-induced autoimmunity are very similar to manifestations of SLE. This includes:

increased levels of Class II MHC
antinuclear antibody production
hypergammaglobulinemia
polyclonal antibody to self-antigens
formation of immune complexes
lymphocyte proliferation
necrotizing vasculitis Mercury-induced autoimmunity is also similar to lupus in that the disease process requires CD4+T-cells, T- and B-cell stimulatory molecules and interferon-γ, which strongly suggests identical pathogenic mechanisms. Given the complexity of metal, interaction with cellular and subcellular components of the immune system and the large number of molecules that may be affected, genetic studies were initiated to define the genes responsible for sensitivity of resistance to mercury-induced autoimmunity. A single major quantitative trait locus on chromosome 1, designated as Hmγ1 was linked to glomerular immune complex deposits (81). Mercury is only one of a number of immunostimulatory heavy metal xenobiotics that can induce adverse immunotoxicity. Several of these such as silver or gold also promote the production of anti-fibrillarin autoantibodies only in mercury-sensitive mouse stains (82).

Indeed after injection of methyl-mercury, a number of murine strains develop an antibody response against U3 small nucleolar ribonucleo-proteins called fibrillarin and chromatin. These antibodies have also been detected in humans with scleroderma. Therefore, detection of antinuclear antibody along with metals, fibrillarin and chromatin antibodies and elevation in immune complexes indicate involvement of metals in induction of inflammation and autoimmunity in autism (82). Further, production of these antibodies may indicate a lack of functional metallothionein at cellular level.

Examples of antibodies associated with autoimmune reaction and involvement of metals to be tested include, but are not limited to, anti-nuclear protein, mercury, fibrillarin, chromatin, immune complexes, and metallothionein.

Neuroimmune Antibodies Induced by Dietary Proteins and Infectious Agents

As mentioned above, many infectious agents have long been suspected of being etiologic factors in autism. Whether or not these viruses actually induce brain autoantibodies has not yet been explored. For this reason, we decided to review the available scientific literature and found that over sixty different microbial peptides have been reported to cross-react with human brain tissue and MBP. Furthermore, these peptides not only have the capacity to cross-react with MBP and induce T-cell response, but also are also able to induce experimental autoimmune encephalomyelitis (11, 26-30).

Among families with autistic children, it is well known that the elimination of milk from the child's diet significantly improves the patient's condition. Investigators found that an encephalitogenic T-cell response to MOG can either be induced or alternatively suppressed as a consequence of immunological cross-reactivity or molecular mimicry with the extracellular IV-like domain of milk protein butyrophilin. All of these clinical laboratory findings shed light on our detection of higher levels of antibodies against milk antigens in autistic sera. Based on earlier publications, we chose *Streptococcus* synthetic peptide containing the conserved M protein or brain crossreactive epitope, a *Chlamydia pneumoniae*-specific peptide and the butyrophilin milk peptide, which modulates the encephalitogenic T-cell response to MOG in experimental autoimmune encephalomyelitis for our cross-reactivity study (11, 65).

Detection of IgG, IgM and IgA antibodies against myelin basic protein, neurofilaments and their cross-reactive epitopes in milk, *Streptococcus* and *Chlamydia* may justify treatment with antibiotic and/or elimination diet.

Examples of neuro-autoimmune antibodies induced by dietary proteins and infectious agents and antibodies associated with the neuro-autoimmune antibodies to be tested include, but are not limited to, myelin basic protein, neurofilament, milk butyrophilin, *streptococcus* M protein, and *chlamydia pneumoniae*.

Binding of Dietary Peptides to Different Tissue Enzymes May Promote Development of Peptidase Antibodies in Children with Autism Opioid peptides are available from a variety of food sources. These dietary proteins and peptides, including casein, casomorphins, gluten (GLU) and gluteomorphins, can stimulate T-cells, induce peptide-specific T-cell responses, and abnormal levels of cytokine production, which may result in inflammation, autoimmune reactions and disruption of neuroimmune communications (54-57). In celiac disease (CD), a majority of patients who express HLD-DQ2 and/or DQ8 react to a 33-mer peptide and 15 other T-cell stimulatory peptides (58, 59). This peptide binding to HLA-DQ2 and HLA-DQ8 molecules is most efficient when negatively charged amino acids are present at anchor positions in the peptide. Yet GLU contains very few negatively charged amino acids, which makes GLU-derived peptides low affinity ligands for HLA-DQ2 and -DQ8. This paradox has been solved by finding that enzyme tissue transglutaminase, target of endomysium-specific antibodies in CD patients, can modify GLU peptides by conversion of glutamine residues into glutamic acid, which introduces negative charges favored for binding (58-60).

A majority of children with autism cannot tolerate wheat and milk proteins or peptides and hence elimination of these peptides from the diets significantly improves their conditions. This clinical finding correlates with laboratory results reported earlier by our group in children with autism (11-15) and by different investigators in MS-like syndromes (61-64). They found that an encephalitogenic T-cell response to myelin oligodendrocyte glycoprotein (MOG) could be either induced or alternatively suppressed as a consequence of immunological cross-reactivity or "molecular mimicry" with the extra-cellular IV-like domain of milk protein called butyrophilin (BTN) (65). We detected IgG, IgM and IgA antibodies against nine specific neuron-specific antigens in the sera of children with autism. These antibodies were found to bind with different encephalitogenic molecules that have sequence homologies to a milk protein (11).

Indeed, when we tested IgG, IgM and IgA antibodies against milk peptides, we found that every single serum with ELISA values higher than 0.3 O.D. against neurological antigens also exhibited high levels of antibodies against neurological antigens and antibodies against milk peptides in a higher percentage of experimental sera. Similar to milk peptides, antibodies against different gliadin peptides have also been described in celiac disease and gluten ataxia (66-67).

Food Allergies and Intolerance

Food allergies may be said to be contributory to the behavioral disorders of individuals inflicted in autism. Sensitivity to gluten and milk are thought to be the major food allergens in these patients. In one study, nineteen children with autistic syndromes were treated with either gluten-free milk and milk-reduced diets, or milk-free and gluten-reduced diets. Before treatment, five of the fifteen fully studied patients had increased levels of IgA antibodies to casein or gluten. After following the diet for a year, improvement was noted in terms of increased social contact, decreased stereotypy, an end to self-mutilation (like head banging), and a decrease in "dreamy state" periods. These improvements were accompanied by a significant decrease in urinary peptide excretion. The possible mechanism is that children with autism suffer from one or more peptidase defects that fail to break down "exomorphins" (exogenous opioids) found in milk and wheat. These exorphin peptides then gain entry into the brain where they significantly disrupt brain chemistry (see FIGS. 2, 3).

The presence of other food allergies should also be determined, as food allergies are likely the factor responsible for the increased intestinal permeability noted in these patients. In fact, increased gut permeability has been suggested as a possible causative factor for autism (73, 77).

Examples of antibodies associated with food allergy and intolerance to be tested include, but are not limited to, milk, casomorphin, wheat gluten/gliadin, gluteomorphin, corn, soy, and tissue enzyme, such as transglutaminase which may modify resultant dietary peptides.

Cross-Reaction Between Gliadin and Cerebellar Purkinje Cells as a Possible Mechanism for Neuroimmune Abnormalities in Autism One of the most frequent presentations of gluten sensitivity is the neurologic dysfunction called gluten ataxia. Up to 33% of patients presenting with neurologic dysfunction and 90% of patients presenting with pruritic vesicular rash of dermatitis herpetiformis associated with gluten sensitivity also have celiac disease (66). While the remaining patients have serologic markers or anti-gliadin antibodies and genetic susceptibility (HLADQ2), they do not have histologic evidence of small bowel involvement. Based on a major epidemiologic study involving more than 200 patients, gluten ataxia was found to account for 40% of cases with idiopathic sporadic cerebellar degeneration. When patients with gluten ataxia were autopsied, perivascular cuffing with inflammatory cells, predominantly affecting the cerebellum, and loss of Purkinje cells were detected. These inflammatory reactions resulting in Purkinje cell loss imply that the neurologic insult may be immune-mediated (67, 69, 70). It is not clear whether such immune-mediated damage is primarily cellular or antibody-driven. In a recent study, investigators assessed the reactivity of sera from patients with gluten ataxia, patients newly diagnosed with celiac disease without neurologic dysfunction and healthy control subjects (67).

Using indirect immunocytochemisty on human cerebellar and rat CNS tissue, cross-reactivity of a commercial IgA antigliadin antibody with cerebellar tissue was analyzed. Sera from 12 of 13 patients with gluten ataxia strongly presented stained Purkinje cells. Less intense staining was observed in some but not all sera from patients with newly diagnosed celiac disease without neurologic dysfunction. At high dilutions (1:800) staining was observed only using sera from patients with gluten, ataxia but not from control subjects. Sera from patients with gluten ataxia also stained some brainstem and cortical neurons in rat CNS tissue. Commercial anti-gliadin antibody stained human Purkinje cells' in a similar manner. Absorption of the antigliadin antibodies using crude gliadin abolished the staining in patients with celiac disease without neurologic dysfunction, but not in those with gluten ataxia. The conclusion suggested that patients with gluten ataxia have antibodies against Purkinje cells that cross-react with epitopes on Purkinje cells, and humoral immune responses are involved in the pathogenesis of gluten ataxia (67).

Direct Evidence for Structural Similarity Between Gliadin Peptides and Cerebellar Antigens Several distinctive neurologic disorders occur in patients with paraneoplastic cerebellar degeneration (PCD). The syndrome of PCD is among the most common of these disorders and generally occurs in patients with neoplasms of the lung, breast, ovary, or with Hodgkin's disease. Neuropathologic features of PCD include extensive loss of Purkinje cells, degenerative changes in the remaining Purkinje cells, as well as variable losses of granule and basket neurons.

The presence of anti-Purkinje cell antibodies in some PCD patients suggests an autoimmune etiology. To identify the molecular targets for these autoantibodies, an Agt11 cDNA expression library from human cerebellum was constructed and screened with IgG from a patient with paraneoplastic cerebellar degeneration. A single clone, pCDR2, produced a fusion protein that reacted strongly with the patient's IgG. Sequencing the pCDR clones revealed 6 amino acids repeated in tandem along the entire cDNA sequence (VAL, PRO, LEU, LEU, GLU, ASP). (SEQ ID NO: 4). This gene was expressed predominantly in neuroectodermal tissues (68).

Neurotransmitters and Neuroimmune Miscommunication

Autism was originally thought to be primarily a psychiatric condition. However, recent biochemical genetic studies have lead to the hypothesis that the disorder is due to an organic defect in brain development. Specifically, autism is thought to be a result of abnormal serotonin metabolism in the brain. The abnormalities that have been documented include:

abnormal release and uptake of serotonin by platelets
abnormal kynurenine metabolism
increased serum serotonin and free tryptophan levels
abnormal urinary 5-hydroxyindolacetic acid (5-HIAA) levels
abnormal urinary Serotonin metabolites The basic defect appears to be a decrease in CNS Serotonin activity despite elevated free tryptophan levels in the serum. Abnormal serotonin metabolites seen in autistic children may significantly contribute to their mental dysfunction (83-85). Drugs such as LSD, psilocybin, ergot, and other hallucinogens are serotonin analogs, and a number of serotonin metabolites are known to be hallucinogens. It is also interesting to note that serotonin and its metabolites are produced in, and absorbed from, the intestines.

This abnormal level of serotonin along with reaction of bacterial toxins, xenobiotics and dietary peptides with different aminopeptidases and gut-neuroimmune communications results in autoantibody production against these important tissue enzymes such as somatostatin, vasoactive intestinal peptides. Formation of antibodies against peptidases results in dysfunctional enzymes and accumulation of peptides in the GI tract and in circulation. These dietary peptides in the blood may bind to G protein receptors, cause immune dysfunction and transmigrate across blood, the blood-brain barrier, and activate the local antigen-presenting cells, such as microglia and astrocytes. By reacting to μ, γ, κ opioid receptors on both lymphocytes and nerve cells, dietary peptides such as pro-dynorphins, dynorphins, casomorphins and gluteomorphins may change the level of cytokine and interfere with neuroimmune communication. Therefore, detection of high or low levels of serotonin along with antibodies to serotonin, somatostatin, vasoactive intestinal peptides, DPP IV, pro-dynorphin and dynorphin may indicate disturbance in gut-neuroimmune communication.

Examples of antibodies associated with neurotransmitters and neuroimmune miscommunication to be tested include, but are not limited to, serotonin receptor antibodies, serotonin antibodies, somatostatin antibodies, vasoactive intestinal peptide, prodynorphin, dynorphin, and dipeptidylpeptidase IV.

Pathogenesis and Mechanism of Autoimmunity and Autism

Figure 2:
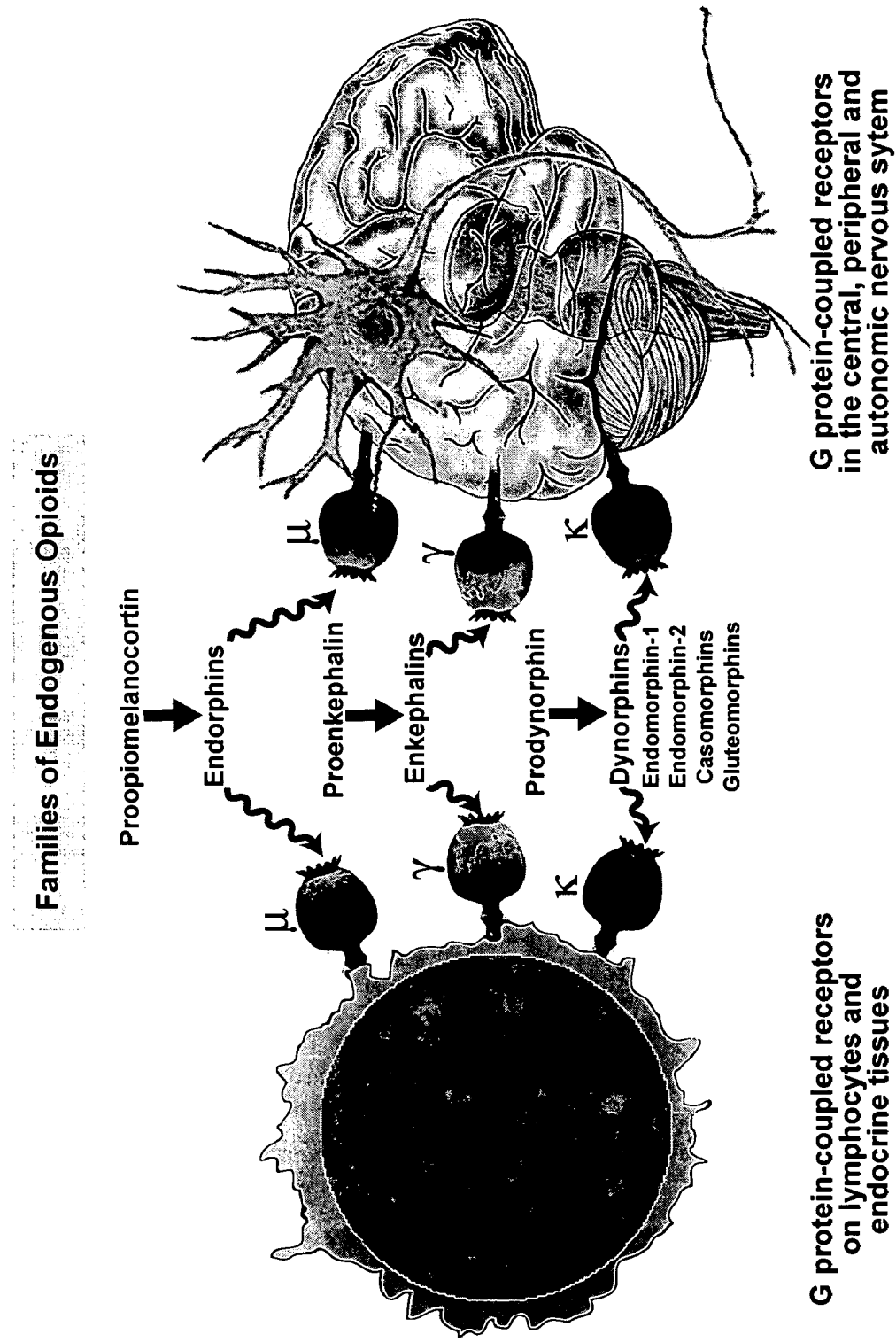
FIG. 2 illustrates the role of endogenous opioids and their receptors on immune and brain functions.
Figure 3:
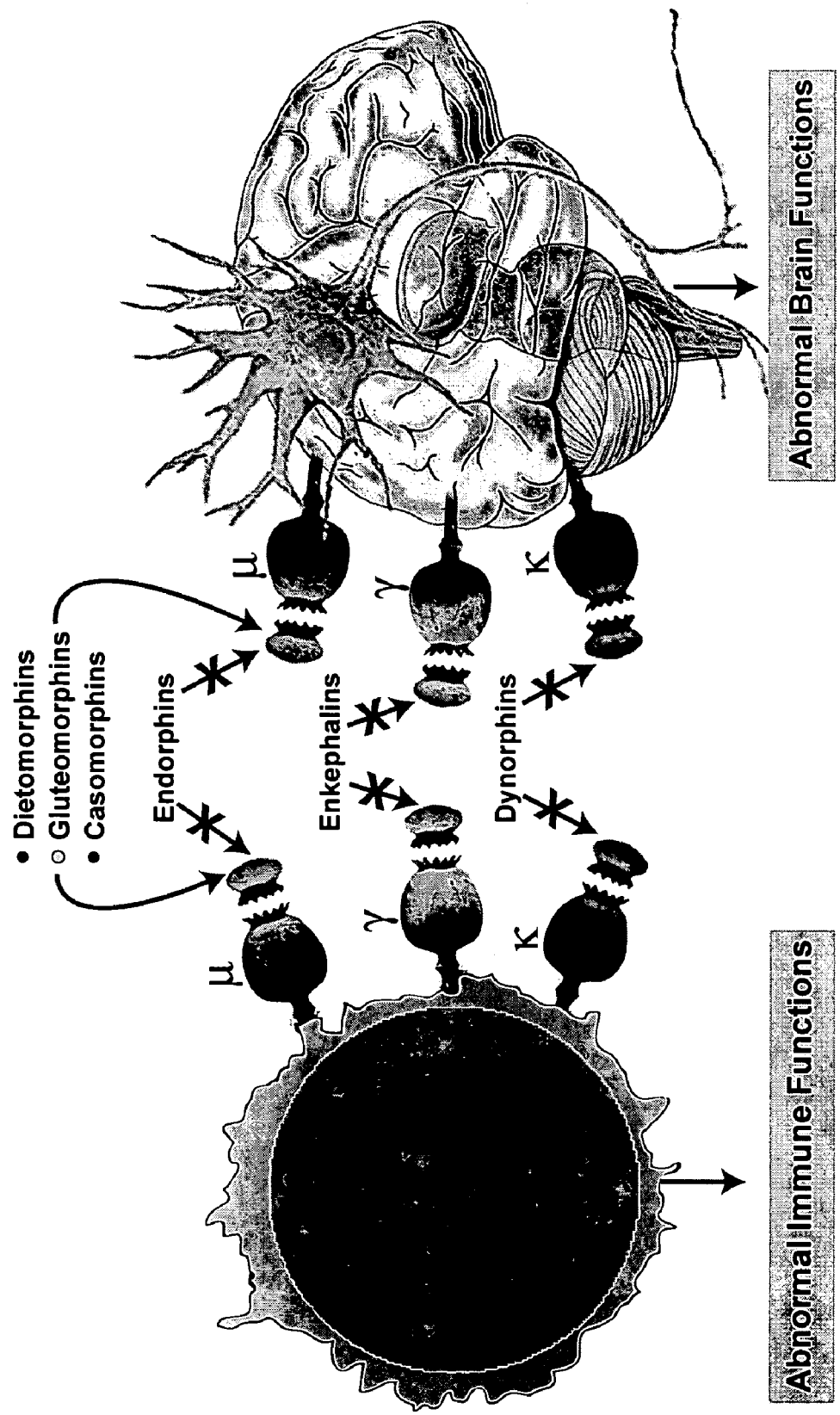
FIG. 3 illustrates dietary peptides binding to μ, γ, and κ opioid receptors on lymphocytes and on the cells of the central, peripheral and autonomic nervous system resulting in abnormal neuroimmune communications, brain and immune functions.
Figure 4:
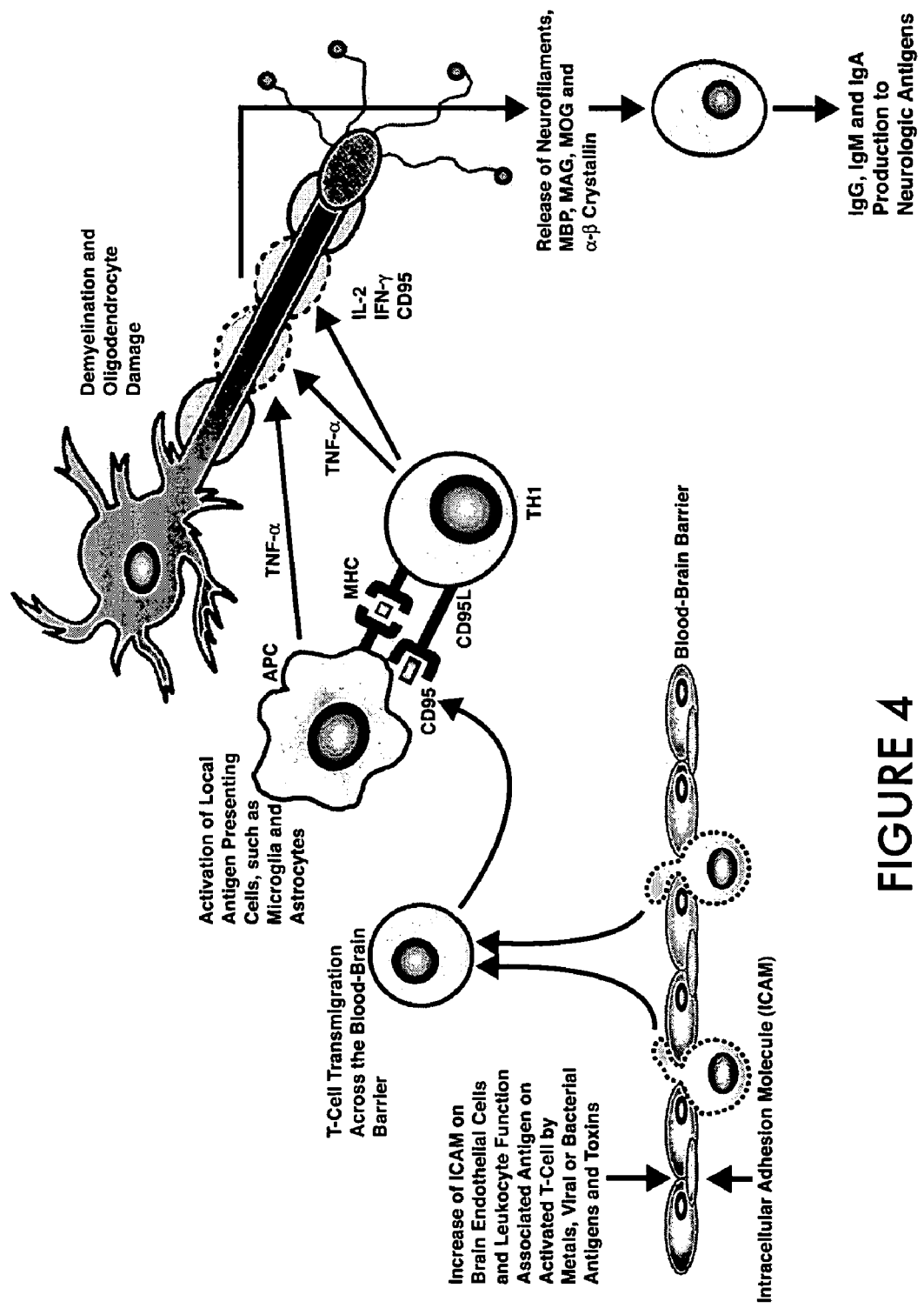
FIG. 4 illustrates cellular and humoral immune mechanisms in infections- and xenobiotics-induced neurotoxicity, which includes neuronal degeneration, secondary demyelination, and possibly reactive astrogliosis. Under pathological conditions, pre-existing autoreactive T-cells are generated by molecular mimicry as a result of sequence homologies or matched motifs between autoantigen and viral, bacterial, or parasitic proteins. Increased ICAM on endothelial cells by xenobiotics and bacterial toxins may allow transmigration of these auto-reactive T-cells across the blood-brain barrier resulting in cellular and humoral immune responses against nerve cells.

For cross-reactive circulating antibodies to become pathogenic, they must cross the blood-brain barrier. It is now known that permeability of the blood-brain barrier increases after major histocompatibility complex class I expression (Fabry et al, 1994), activated lymphocyte interaction, and change in neuronal cell adhesion molecules (71, 72). Based on review of literature and results reported here, we propose the following chain of events, as shown in FIG. 4, that may explain possible mechanisms of injury in autism:

1. In the course of a lifetime, the body is exposed to infectious agents, which mimic neuron-specific antigens, such as EBV, CMV, HHV-6, HTLV-1, HTLV-2, *streptococcus*, *Chlamydia pneumoniae* or even milk and gluten peptides.
2. Pre-existing auto-reactive T-cells are generated by molecular mimicry as a result of contact with dietary proteins and viral, bacterial, and parasitic antigens, which have sequence homologies or matched motifs with auto antigens.
3. Bacterial enterotoxins, viral antigens, and metals, such as mercury and lead, may increase adhesion molecules on brain endothelial cells. Toxic chemicals may also increase leukocyte function-associated antigens on activated T-cells.
4. Pre-existing autoreactive T-cells may transmigrate across the blood-brain barrier and induce the activation of local antigen-presenting cells, such as microglia and astrocytes.
5. By reacting to μ, γ, and κ opioid receptors on both lymphocytes and nerve cells, dietary peptides such as casomorphins, gluteomorphins and others may change the level of cytokine production and interfere with neuroimmune communication (19, 20, 53; FIGS. 2, 3).
6. This neuroimmune miscommunication may result in production of IL-2, INF-γ and TNF-α by T-helper-I autoreactive cells and TNF-α by the antigen presenting cells (astrocytes and microglia may result in oligodendrocyte damage and demyelination).
7. As a result of this sequence of events, MBP, MAG, MOG, α, β-crystallin and other antigens are released from neurofilaments and enter the circulatory system. This results in immune reactions, such as the formation of plasma cells with the capacity of producing IgG, IgM and IgA antibodies against neuron-specific antigens.
8. These antibodies may cross the blood-brain barrier and combine with brain tissue antigens to form immune complexes, thus causing further damage to the neurological tissue. The antibodies, along with toxic biological weaponry, such as arachidonic acid and free radicals, can "chew off" neuron myelin and impair electrical transmission between a muscle and the central nervous system.
9. This hypothesis may explain significant differences in levels of pathogenic autoantibodies between control subjects and patients exposed to toxic chemicals and metals (11, 15, 19, 20, 53).

An embodiment provides for a method for determining etiology of an autistic spectrum disorder in a patient, comprising the steps of:

a) determining a level of at least one infectious agent derived antigen or antibody against an infectious agent derived antigen, at least one toxic chemical derived antigen or an antibody against a toxic chemical, and at least one dietary protein derived antigen or antibody against a dietary protein, in one or more samples from the patient;

b) comparing the level of antigens and/or antibodies determined in step a) with a normal level of the antigens and/or antibodies from control subjects, wherein (i) normal level or lower than normal level of antigens and/or antibodies for the each of said antigens indicate absence of an etiology of autistic spectrum disorder from presence of said antigens; and (iv) higher than normal level of antigens and/or antibodies for one or more of said antigens and/or antibodies indicates a likelihood of the autistic spectrum disorder being based on the presence of said antigens.

Another embodiment provides for a method for determining etiology of an autistic spectrum disorder in a patient, comprising the steps of:

a) determining a level of antibodies to a self-tissue or peptide in one or more samples from the patient; and b) comparing the level of antibodies determined in step a) with a normal level of the antibodies from control subjects, wherein
  (i) normal level or lower than normal levels of antibodies indicate absence of etiology of autistic spectrum disorder from presence of said antibodies; and
  (ii) higher than normal level of the antibodies indicates a likelihood of the autistic spectrum disorder being based on the presence of said antibodies.

Preferred self-tissue or peptide include, but is not limited to, tissue and cell antigens, receptors, mediators, enzymes, and neurotransmitters. More specifically, preferred self-tissue or peptide include, but is not limited to, digestive enzymes (pepsin, trypsin, chymotrypsin), aminopeptidase, dipeptidyl peptidase, CD26, DPPI IV, CD13, CD69, transglutaminase, epithelial cells, brush border antigens and enzymes, colon tissue antigens, gastrin, gastrin inhibitory polypeptide, secretin, motilin, enkephelin, substance P, somatostatin, and serotonin. When a preferred self-tissue antigen or peptide is a neurotransmitter or a neurotransmitter receptor, the preferred self-tissue antigen or peptide is selected from the group consisting of serotonin receptor, serotonin, somatostatin, vasoactive intestinal peptide, prodynorphin, dynorphin, dipeptidylpeptidase IV, and complex dipeptidylpeptidase IV.

Material and Methods

An immunoassay, such as ELISA, RAST, DotBlot, Western Blot and others can be used in embodiments.

The following antigens, proteins, peptides, enzymes, tissue receptors, lymphocyte receptors, neurotransmitters listed below are representative of antigens used in assays of preferred embodiments.

```
MBP Sequence 87-106              VVHFFKNIVTPRTPPPSQGK        (SEQ ID NO:5)

MBP Sequence 83-89               ENPVVHFFKNIVTPRTP           (SEQ ID NO:6)

MBP Sequence 1-11                ASQKRPSQRSK                 (SEQ ID NO:7)

MBP Sequence 200-211             ANMQRQAVPTL                 (SEQ ID NO:8)

Proteolipid Protein Sequence 40-60    TGTEKLIETYFSKNYQDYEYL  (SEQ ID NO:9)

Proteolipid Protein Sequence 89-106   GFYTTGAVRQIFGDYKTT     (SEQ ID NO:10)

Proteolipid Protein Sequence 103-120  YKTTICGKGLSATVTGGQ     (SEQ ID NO:11)

Proteolipid Protein Sequence 125-143  SRGQHQAHSLERVCHCLGK    (SEQ ID NO:12)

Proteolipid Protein Sequence 139-154  HCLGKWLGHPDKFVGI       (SEQ ID NO:13)

Transaldolase Protein Sequence 11-25   MESALDQLKQFTTVV       (SEQ ID NO:14)

Transaldolase Protein Sequence 21-35   ETTVVADTGDFHAID       (SEQ ID NO:15)

Transaldolase Protein Sequence 31-45   FHAIDEYKPQDATTN       (SEQ ID NO:16)

Transaldolase Protein Sequence 71-85   KLGGSQEDQIKNAID       (SEQ ID NO:17)

Transaldolase Protein Sequence 81-95   KNAIDKLFVLFGAEI       (SEQ ID NO:18)

Transaldolase Protein Sequence 261-275 GELLQDNAKLVPVLS       (SEQ ID NO:19)

Transaldolase Protein Sequence 271-285 VPVLSAKAAQASDLE       (SEQ ID NO:20)

Transaldolase Protein Sequence 311-325 GIRKFAADAVKLERM       (SEQ ID NO:21)

MOG Sequence 1-20                GQFRVIGPRHPIRALVGDEV        (SEQ ID NO:22)

MOG Sequence 61-80               QAPEYRGRTELLKDAIGEGK        (SEQ ID NO:23)

MOG Sequence 101-120             RDHSYQEEAAMELKVEDPFY        (SEQ ID NO:24)

MOG Sequence 145-160             VFLCLQYRLRGKLRAE            (SEQ ID NO:25)

MAG Sequence 37-60               REIVDRKYSICKSGCFYQKKEEDW    (SEQ ID NO:26)

Sodium Ion Channel               (SEQ ID NO:27)

Na 1.2                           TVTVPIALGESDFENLNTEEFSSESDM (SEQ ID NO:28)

Na 1.3                           TVTVPIAVGESDFENLNTEEFSSESEL (SEQ ID NO:29)

Na 1.1                           TVTVPIAVGESDFENLNTEDFSSESDL (SEQ ID NO:30)

Na 1.6                           TVRVPIAVGESDFENLNTEDVSSESDP (SEQ ID NO:31)

Glutamate Receptor               ANEYERFVPFSDQQISNDAAC       (SEQ ID NO:32)

Cerebellar peptides              FLEDVPLLEDIPLEDVPLLED       (SEQ ID NO:33)
```

-continued

| | | |
|---|---|---|
| | FLEDVPLLEDIPLLEDVP | (SEQ ID NO:34) |
| | LLEDTDFLEDPDFLEAID | (SEQ ID NO:35) |
| Amyloid β | DAEFRHDSGYEVHHQKLVFFAEDVGSNKGAIIGLMVGGVVIA | (SEQ ID NO:36) |
| CD69-Human | MECEKNLYWICNKPYK | (SEQ ID NO:37) |
| Zinc Finger Protein | PYKCPECGKSFSQKSDLVKHQRTHTG | (SEQ ID NO:38) |
| Glucose Regulated Protein-78 (GRP-78) | EEEDKKEDVGTVVGI | (SEQ ID NO:38) |
| Vasoactive Intestinal Peptide | NYTRLRKQMAVKKYL | (SEQ ID NO:39) |
| Gliadin Peptides | QPFRPQQPYPQPQPQYSQPQQ | (SEQ ID NO:40) |
| | QPYPQPQPQYSQPQQPISQQQ | (SEQ ID NO:41) |
| | QFLGQQQPFPPQQPYPQPQPF | (SEQ ID NO:42) |
| | PLVQQQQFLGQQQPFPPQQPY | (SEQ ID NO:43) |
| | HNVVHAIILHQQQQQQQEQKQ | (SEQ ID NO:44) |
| | NPSQQQPQEQVPLVQQQ | (SEQ ID NO:45) |
| | QQLPQPQQPQQSFPQQQPF | (SEQ ID NO:46) |
| Gluteomorphin | YPFPGPIP | (SEQ ID NO:47) |
| Casomorphin | GYYPTYGGWL | (SEQ ID NO:48) |
| Secretin (human) | HSDGTFTSELSRLREGARLQRLLQGLV | (SEQ ID NO:49) |
| Campylobacter Jejuni Toxin | TPPLLAAILMLASLRSHIVSDHFPVNFRKF | (SEQ ID NO:50) |
| α-S1 Casein | RPKHPIKHQGLPQEVLNENLLRFFVAPFPEVFGKEKVNELSKDIGSESTDEQAMEDIK QMEAESISSSEEIVPNSVEQKHIQKEDVPSERYLGYLEQLLRLKKYKVPQLEIVPNSAE ERLHSMKEGIHAQQKEPMIGVNQELAYFYPELFRQFYQLDAYPSGAWYYVPLGTQY TDAPSFSDIPNPIGSENSEKTTMPLW | (SEQ ID NO:51) |
| α-S2 Casein | MKEGIHAQQK | (SEQ ID NO:52) |
| | YQKFALPQYL | (SEQ ID NO:53) |
| K Casein | KDERFFSDKI | (SEQ ID NO:54) |
| | SPPEINTVQV | (SEQ ID NO:55) |
| Vasoactive Intestinal Peptide | HSDAVFTDNYTRLRKQMAVKKYLNSILN | (SEQ ID NO:56) |
| Somatostatin | YSANSNPAMAPRERKAGCKNFFWKTFTSC | (SEQ ID NO:57) |
| Substance P | RQKPQQFFGLM | (SEQ ID NO:58) |
| Oxytocin | CYKQNCPLG | (SEQ ID NO:59) |
| Pancreatic Peptide | APLEPVYPGDNATPEQMAQYAADLRRYINMLTRPRY | (SEQ ID NO:60) |
| Gastrin-1 | EGPWLEEEEEAYGWMDF | (SEQ ID NO:61) |
| Big Gastrin-1 | ELGPQGPPHLVADPSKKQGPWLEEEEEAYGWMDF | (SEQ ID NO:62) |
| Gastrin Releasing Peptide | VPLPAGGGTVLTKMYPRGNHWAVGHLM | (SEQ ID NO:63) |
| Enkephalin | YGGFLM | (SEQ ID NO:64) |
| β-Endorphin | YGGFMTSEKSQTPLVTLFKNAIIKNAYKKGE | (SEQ ID NO:65) |
| Big Endorphin | CSCSSLMDKECVYFCHLDIIWVNTPEHVVPYGLGSPRS | (SEQ ID NO:66) |
| Dynorphin A | YGGFLRRIRPKLKWDNQ | (SEQ ID NO:67) |
| Dynorphin B | YGGFLRRQFKVVT | (SEQ ID NO:68) |

-continued

| | | |
|---|---|---|
| Serotonin Receptor | MPHLLSGFLEVTASPAPTWDAP | (SEQ ID NO:69) |
| | IFGHFFCNVFIAMDVMCCTASI | (SEQ ID NO:70) |
| | LKLAERPERSEFVLQNSDHCGK | (SEQ ID NO:71) |
| Fibrillin | SFRPGSRGGSRG | (SEQ ID NO:72) |
| Calreticullin | EQFLDGDGWTSRWIESGLQTSQ | (SEQ ID NO:73) |
| Motillin | FVPIFTYGELQRMQEKERNKGQ | (SEQ ID NO:74) |
| Chlamydia HSP-60 | LKQIAAHAGKEGAIIFQQVM | (SEQ ID NO:75) |

Human HSP-60

| | | |
|---|---|---|
| 1–20 | MLRLPTVFRQMRPVSRVLAP | (SEQ ID NO:76) |
| 16–35 | RVLAPHLTRAYAKDVKFGAD | (SEQ ID NO:77) |
| 31–50 | KFGADARALMLQGVDLLADA | (SEQ ID NO:78) |
| 46–65 | LLADAVAVTMGPKGRTVIIE | (SEQ ID NO:79) |
| 61–80 | TVIIEQSWGSPKVTKDGVTV | (SEQ ID NO:80) |
| 76–95 | DGVTVAKSIDLKDKYKNIGA | (SEQ ID NO:81) |
| 91–110 | KNIGAKLVQDVANNTNEEAG | (SEQ ID NO:82) |
| 106–125 | NEEAGDTTTATVLARSIAK | (SEQ ID NO:83) |
| 121–140 | RSIAKEGFEKISKGANPVEI | (SEQ ID NO:84) |
| 136–155 | NPVEIRRGVMLAVDAVIAEL | (SEQ ID NO:85) |
| 151–170 | VIAELKKQSKPVTTPEEIAQ | (SEQ ID NO:86) |
| 166–185 | EEIAQVATISANGDKEIGNI | (SEQ ID NO:87) |
| 181–199 | EIGNIISDAMKKVGRKGVI | (SEQ ID NO:88) |
| 195–214 | RKGVITVKDGKTLNDELEII | (SEQ ID NO:89) |
| 210–229 | ELEIIEGMKFDRGYISPYFI | (SEQ ID NO:90) |
| 225–244 | SPYFINTSKGQKCEFQDAYV | (SEQ ID NO:91) |
| 240–259 | QDAYVLLSEKKISSIQSIVP | (SEQ ID NO:92) |
| 255–275 | QSIVPALEIANAHRKPLVIIA | (SEQ ID NO:93) |
| 271–290 | LVIIAEDVDGEALSTLVLNR | (SEQ ID NO:94) |
| 286–305 | LVLNRLKVGLQVVAVKAPGF | (SEQ ID NO:95) |
| 301–320 | KAPGFGDNRKNQLKDMAIAT | (SEQ ID NO:96) |
| 316–335 | MAIATGGAVFGEEGLTLNLE | (SEQ ID NO:97) |
| 331–350 | TLNLEDVQPHDLGKVGEVIV | (SEQ ID NO:98) |
| 346–365 | GEVIVTKDDAMLLKGKGDKA | (SEQ ID NO:99) |
| 361–380 | KGDKAQIIKRIQEIIEQLDV | (SEQ ID NO:100) |
| 376–395 | EQLDVTTSEYEKEKLNERLA | (SEQ ID NO:101) |
| 391–410 | NERLAKLSDGVAVLKVGGTS | (SEQ ID NO:102) |
| 406–425 | VGGTDVEVNEKKDRVTDAL | (SEQ ID NO:103) |
| 421–440 | VTDALNATRAAVEEGIVLGG | (SEQ ID NO:104) |
| 436–455 | IVLGGGCALLRCIPALDSLT | (SEQ ID NO:105) |
| 451–470 | LDSLTPANEDQKIGIEIIKR | (SEQ ID NO:106) |

-continued

| | | |
|---|---|---|
| 466–485 | EIIKRTLKIPAMTIAKNAGV | (SEQ ID NO:107) |
| 481–500 | KNAGVEGSLIVEKIMQSSSE | (SEQ ID NO:108) |
| 496–515 | QSSSEVGYDAMAGDFVNMVE | (SEQ ID NO:109) |
| 511–530 | VNMVEKGIIDPTKVVRTALL | (SEQ ID NO:110) |
| 526–545 | RTALLDAAGVASLLTTAEVV | (SEQ ID NO:111) |
| 541–560 | TAEVVVTEIPKEEKDPGMGA | (SEQ ID NO:112) |
| 556–573 | PGMGAMGGMGGGMGGGMF | (SEQ ID NO:113) |
| 437–460 | VLGGGVLLLRVIPALDSLTPANED | (SEQ ID NO:114) |

Dipeptidylpeptidase peptides

| | | |
|---|---|---|
| Peptide 1 | MKTPWRVLLGLLGAAALVTIITVPVVLLNK | (SEQ ID NO:115) |
| Peptide 2 | MAEYGNSSVFLENSTFDEFGH | (SEQ ID NO:116) |
| Peptide 3 | KRQLITEERIPNNTQWVTWSP | (SEQ ID NO:117) |
| Peptide 4 | NGTFLAYAQFNDTEVPLIEYS | (SEQ ID NO:118) |
| Peptide 5 | VTNATSIQITAPASMLIGDHY | (SEQ ID NO:119) |
| Peptide 6 | IQNYSVMDICDYDESSGRWNC | (SEQ ID NO:120) |
| Peptide 7 | NSFYKIISNEEGYRHICYFQI | (SEQ ID NO:121) |
| Peptide 8 | NVQMPSKKLDFIILNETKFWY | (SEQ ID NO:122) |
| Peptide 9 | PEDNLDHYRNSTVMSRAENFK | (SEQ ID NO:123) |
| Peptide 10 | TAHQHIYTHMSHFIKQCFSLP | (SEQ ID NO:124) |

Figure 5:
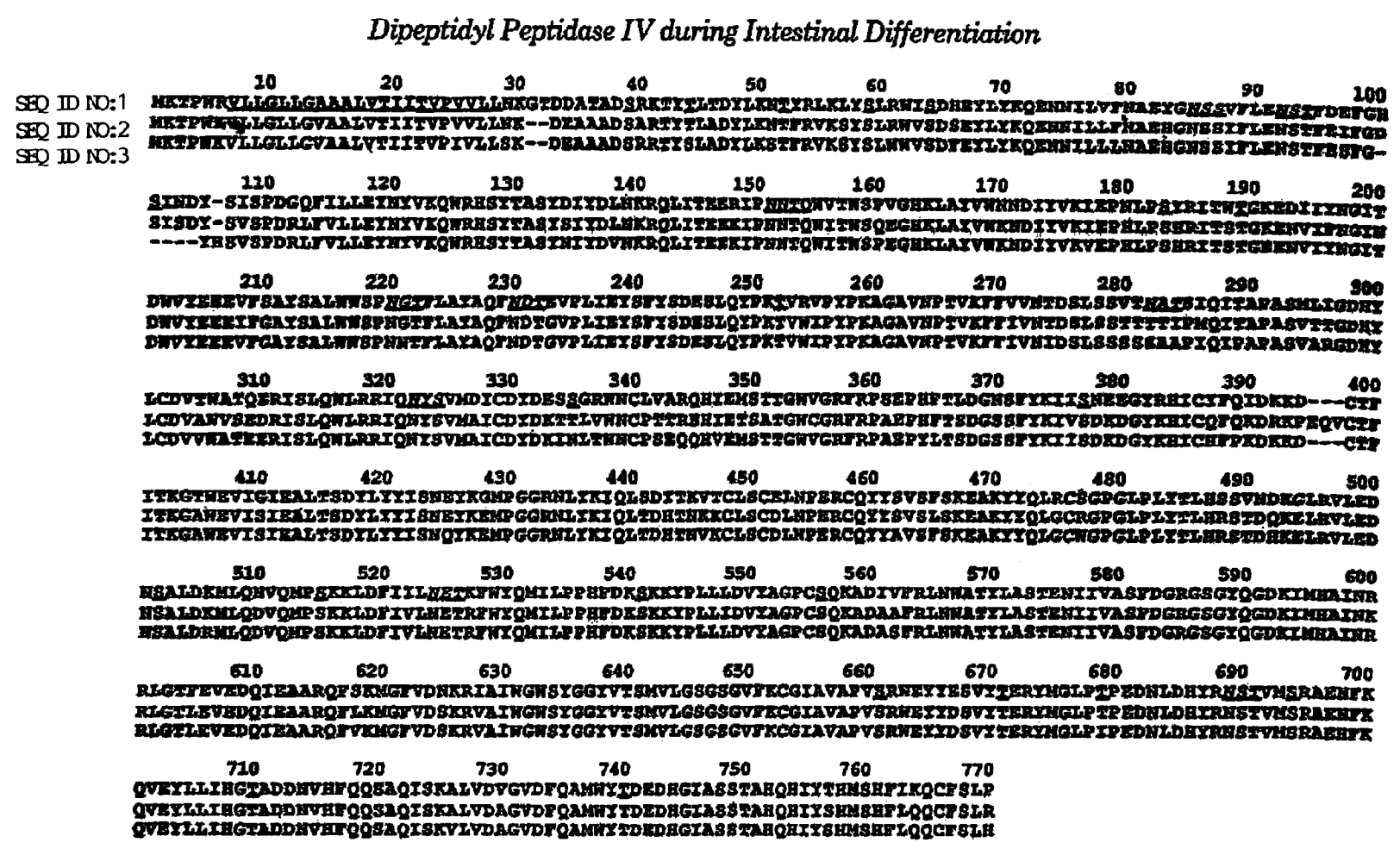

FIG. 5 shows sequences for Dipeptidyl Peptidase IV during intestinal differentiation which is also useful in assays of preferred embodiments. FIG. 5 compares the amino acid sequences of human, rat, and mouse DPP IV, respectively. These sequences are aligned. The potential sites for phosphorylation (T or S) and for N-glycosylation (NXT) are displayed as underlined. Preferred embodiments include the sequences listed above, along with counterparts which have post-translational modifications.

ELISA Procedure

Enzyme-linked immunosorbent assay (ELISA) was used for testing antibodies against different neuron-specific antigens, milk and bacterial peptides in the sera of patients with autism and control subjects. Antigens or peptides proteins, enzymes, neurotransmitters were dissolved in methanol at a concentration of 1.0 mg/ml, then diluted 1:100 in 0.1 M carbonate-bicarbonate buffer, pH 9.5, and 50 µl were added to each well of a polystyrene flat-bottom ELISA plate. Plates were incubated overnight at 4° C. and then washed three times with 20 mM tris-buffered saline (TBS) containing 0.05% Tween 20, pH 7.4. The nonspecific binding of immunoglobulins was prevented by adding a mixture of 1.5% bovine serum albumin (BSA) and 1.5% gelatin in TBS, and then incubating for 2 h at room temperature, and then overnight at 4° C. Plates were washed as in the above, and then serum samples diluted 1:100 in 1% BSA-TBS were added to duplicate wells and incubated for 2 h at room temperature. Plates were washed, and then enzyme-conjugated or alkaline goat anti-human IgG, IgM or IgA antiserum (KPI, Gaithersburg, Md.) were optimally diluted in 1% BSA-TBS was added to each well; the plate was incubated for an additional 2 h at room temperature. After washing five times with TBS-Tween buffer, the enzyme reaction was started by adding 100 µl of substrate. After 45 min, the reaction was stopped with 50 µl of stop solution. The optical density (O.D.) was read at 405 or 492 nm by means of a microtiter reader. Several control wells containing all reagents, but human serum, were used for detecting non-specific binding.

Based on the above, a series of ELISA experiments was performed to establish the binding specificity of peptides, SK and mercury to CD26 and CD69. The plates were coated with CD26 or CD69 first and then with 1% BSA or HSA for inhibition of non-specific binding to microplate wells. Gliadin, casein peptides, SK and ethyl mercury were then added. Plates were incubated for one hour at 37° C. and washed five times for removal of unbound competing antigens. Then, for demonstration of casein, gliadin, SK and mercury binding to CD26 and CD69 purified enzyme labeled rabbit anti-CD26 and CD69 were added to different wells. After proper incubation and washing, binding of these peptides and proteins to CD26 and CD69 was measured by addition of peroxidase substrate and measurement of color development at 492 nm. Binding of dietary peptides, SK and ethyl mercury to CD26 and CD69 was demonstrated by % inhibition in binding of CD26 or CD69 to anti-CD26 and anti-CD69 to its specific antibody and different peptides, SK or mercury was calculated by using the following formula:

% binding of gliadin to CD26 and inhibition of anti-CD26 binding to CD26 =

-continued $$100 - \frac{\text{O.D. after addition of peptide} - \text{background O.D.}}{\text{O.D. of CD26 + antiCD26} - \text{background O.D.}} (100)$$

EXAMPLE

O.D. for CD26+anti-CD26=2.16
O.D. for CD26+gliadin and anti-CD26=1.19
O.D. for background=0.28

% binding of gliadin to CD26 =

$$100 - \frac{1.19 - 0.28}{2.16 - 0.28}(100) = 100 - \frac{0.91}{1.88}(100) = 100 - 48 = 52$$

Bacterial Toxins Ethyl Mercury and Dietary Peptides Bind to Dipeptidylpeptidase IV (CD26) and C D69 and Induce Antibody Production For an examination of the possible involvement of gliadin, casein peptides, SK and ethyl mercury in the production of autoantibodies against CD26 and CD69, calculations of the simultaneous elevation of these antibodies in patients' sera were made, as is summarized in Table 1. Analysis of data showed that while some patients had elevated IgG, IgM or IgA against 1 or 2 of 6 tested antigens, different subgroups showed simultaneous elevation in IgG, IgM or IgA antibodies not only against CD26 and CD69, but also against gliadin (GLI), casein (CA), peptides, SK, ethyl mercury (Hg) or a combination of CD26 or CD69+GLI+CA, or GLI+CA+SK+Hg (Table 1). For example, patients #2, 4, 13, 19, 23, 24, 29, 30, 31, 32, 34 and 38 demonstrated IgG antibody elevation not only against CD69 but also against gliadin, casein, SK or their combinations. Similarly, patients #4, 13, 28, 32 and 48 demonstrated IgM antibody elevation against CD26 or CD69 in combinations with gliadin, casein and SK; patients #1, 2, 3, 4, 6, 13, 14, 16, 21, 24, 29, 33, 41 and 42 demonstrated IgA antibodies against CD26, CD69, gliadin, casein or SK. In patient #13, with the exclusion of IgG and IgA against mercury, all other measurements were highly elevated. This suggests that the patient not only reacted against CD26 and CD69, but also against gliadin, casein, SK, and mercury as well (Table 1).

Figure 6:
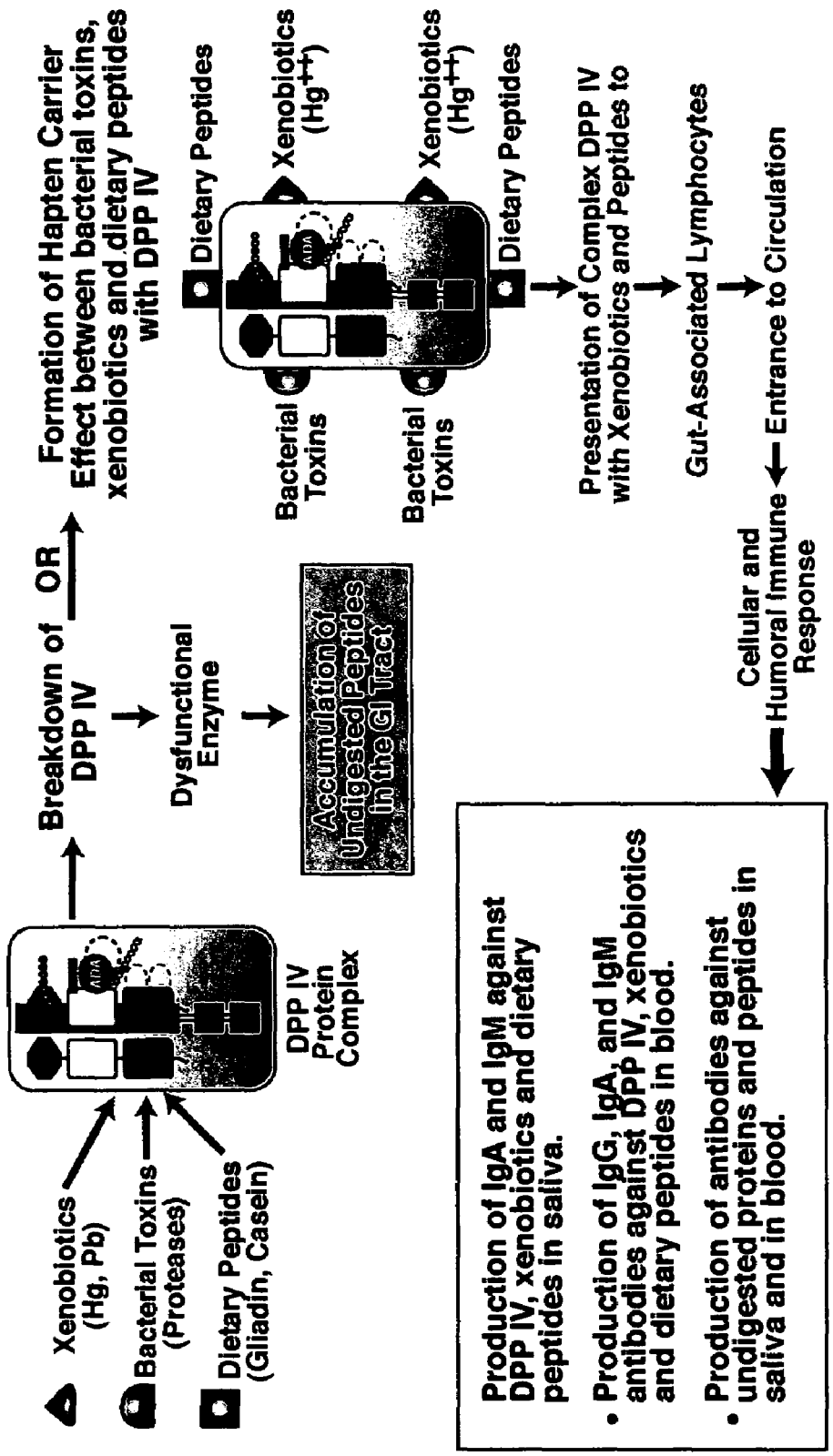
FIG. 6 illustrates xenobiotics, bacterial toxins, and dietary peptides binding to DPP IV, formation of Hapten Carrier Effect, and production of antibodies against DPP IV, xenobiotics, peptides and bacterial toxins. This may result in dysfunction of DPP IV molecule and accumulation of peptides in the GI tract and in circulation.

This simultaneous elevation of anti-CD26, casein, gliadin, SK, and mercury in children with autism further supports the argument for the binding of these dietary and bacterial peptides or antigens to tissue enzymes (dipeptidylpeptidase) or lymphocyte receptors (CD26). The possible mechanism of action for DPP IV binding with dietary peptides, infections, and xenobiotics, resulting in antibody production against DPP IV, gliadin, casein, SK and mercury is shown in FIG. 6.

TABLE I

Simultaneous Detection of Antibodies Against DC26, DC69, Gliadin (Gli), Casein Peptides (CA), SK, and Ethyl Mercury (Hg) in Children with Autism

| | IgG | | | | | | IgM | | | | | | IgA | | | | | |
| --- | --- | --- | --- | --- | --- | --- | --- | --- | --- | --- | --- | --- | --- | --- | --- | --- | --- | --- |
| Specimen # | CD26 | CD69 | Gli | CA | SK | Hg | CD26 | CD69 | Gli | CA | SK | Hg | CD26 | CD69 | Gli | CA | SK | Hg |
| 1 | − | − | M | M | M | M | − | + | − | − | + | − | M | M | M | M | M | − |
| 2 | M | M | M | M | M | − | − | − | − | − | + | − | M | M | M | M | M | + |
| 3 | − | − | − | − | + | − | + | + | − | + | + | + | M | M | M | − | + | − |
| 4 | − | M | M | M | M | − | − | M | M | M | M | − | + | M | M | M | M | − |
| 5 | − | − | − | − | − | − | − | − | − | − | + | + | − | − | − | − | − | − |
| 6 | − | − | − | − | − | − | + | + | − | − | + | − | M | M | M | M | − | − |
| 7 | − | − | − | − | − | − | − | − | − | − | − | − | − | − | − | − | − | − |
| 8 | + | − | + | − | − | − | − | − | − | − | − | − | − | − | + | + | − | − |
| 9 | − | − | − | + | − | − | − | + | − | − | − | − | − | − | − | − | − | − |
| 10 | − | − | − | − | − | − | − | − | − | − | − | − | − | − | − | − | − | − |
| 11 | − | + | − | − | − | − | + | − | − | − | − | − | − | − | − | − | − | − |
| 12 | − | − | − | − | − | − | + | − | − | − | + | + | − | − | − | − | + | − |
| 13 | M | M | M | M | M | − | M | M | M | M | M | + | M | M | M | M | M | − |
| 14 | − | − | − | − | − | − | − | − | + | + | − | − | M | M | M | M | − | − |
| 15 | + | − | − | + | + | − | − | − | + | + | + | − | − | − | − | − | − | − |
| 16 | M | − | M | M | M | − | + | − | − | − | + | − | M | M | M | M | − | − |
| 17 | − | − | − | − | − | − | − | + | + | − | − | − | − | − | − | − | − | − |
| 18 | − | − | − | − | − | − | − | − | − | − | − | − | − | − | − | − | − | − |
| 19 | M | M | M | M | M | M | − | − | − | − | + | − | + | − | + | + | − | − |
| 20 | − | − | − | + | + | − | + | − | + | + | − | − | − | − | − | − | − | − |
| 21 | + | − | − | − | − | + | + | − | − | + | − | − | M | M | M | − | M | − |
| 22 | − | − | − | − | − | − | − | + | − | + | − | − | − | + | − | + | − | − |
| 23 | M | M | M | M | M | − | − | − | − | − | + | + | − | − | − | + | − | − |
| 24 | + | + | + | − | − | − | − | − | − | − | + | − | + | + | + | − | − | − |
| 25 | M | − | M | M | M | M | − | − | − | − | − | − | − | − | − | − | − | − |
| 26 | − | + | − | + | − | − | + | + | − | − | + | + | − | − | − | − | − | + |
| 27 | + | + | + | − | − | + | + | − | − | − | + | − | − | − | − | − | − | − |
| 28 | − | − | − | − | − | + | − | M | M | M | M | − | + | + | − | − | − | − |
| 29 | M | M | M | M | − | + | − | − | − | − | + | + | M | M | − | M | M | − |
| 30 | + | + | + | − | − | − | − | − | + | + | − | − | − | − | + | + | − | − |
| 31 | M | M | M | M | − | − | + | + | − | − | − | − | + | + | − | − | − | − |
| 32 | M | M | M | M | M | − | M | − | M | M | M | M | − | − | + | + | + | − |
| 33 | + | − | − | − | − | − | + | − | − | + | + | − | + | + | + | − | − | − |
| 34 | M | M | M | M | − | + | − | − | + | + | + | + | − | + | + | + | − | + |

TABLE I-continued

Simultaneous Detection of Antibodies Against DC26, DC69, Gliadin (Gli), Casein Peptides (CA), SK, and Ethyl Mercury (Hg) in Children with Autism

| | IgG | | | | | | IgM | | | | | | IgA | | | | | |
|---|---|---|---|---|---|---|---|---|---|---|---|---|---|---|---|---|---|---|
| Specimen # | CD26 | CD69 | Gli | CA | SK | Hg | CD26 | CD69 | Gli | CA | SK | Hg | CD26 | CD69 | Gli | CA | SK | Hg |
| 35 | − | − | − | − | + | + | − | − | − | + | + | − | − | − | − | − | + | + |
| 36 | − | + | − | − | − | − | + | − | − | − | − | − | + | + | − | − | − | − |
| 37 | − | − | − | − | − | − | − | − | + | + | − | − | − | − | + | + | − | − |
| 38 | M | M | M | M | − | − | + | − | − | − | − | − | + | + | − | − | − | − |
| 39 | − | − | − | − | + | − | − | − | + | + | − | + | − | − | − | − | + | − |
| 40 | + | − | − | − | − | − | − | − | − | − | − | − | − | − | − | − | − | − |
| 41 | − | − | + | + | − | − | + | − | − | − | − | − | M | M | M | M | − | − |
| 42 | + | − | + | − | + | + | + | − | + | + | − | + | M | M | M | M | M | + |
| 43 | − | + | − | − | − | + | − | − | − | − | − | + | − | + | − | − | − | − |
| 44 | + | − | − | + | − | − | − | − | + | + | − | − | + | + | − | − | − | − |
| 45 | + | − | − | − | + | + | + | + | − | − | − | − | − | − | + | + | + | − |
| 46 | − | − | − | − | − | − | − | + | + | + | − | − | + | − | − | − | − | − |
| 47 | + | − | + | + | − | − | + | + | − | − | − | − | + | + | − | − | − | − |
| 48 | − | − | + | − | − | + | M | M | M | − | M | M | − | − | + | + | − | − |
| 49 | − | + | + | + | − | − | − | − | + | − | + | + | − | − | + | + | − | − |
| 50 | + | − | − | − | − | − | − | − | − | − | − | − | − | − | − | − | − | − |

− = negative
+ = positive
M = multiple positive results

Binding of Gliadin, Casein Peptides, SK and Ethyl Mercury to CD26 and CD69

For demonstration of gliadin, casein, SK and mercury binding to CD26 and CD69, polyclonal antibodies raised against CD26 or CD69 and labeled with enzyme were added to different wells coated either with CD26 or CD69. Rabbit anti-CD26 reacted only with wells coated with CD26 that resulted in an ELISA O.D. of 2.16. Adding rabbit anti-CD69 to wells coated with CD69 gave an ELISA O.D. of 1.92. Adding gliadin, casein, SK and mercury to wells coated with either CD69 or CD26 caused 52%, 44%, 77% and 73% inhibition in binding of anti-CD26 to CD26. Similarly, in wells coated with CD69, gliadin, casein, SK and mercury caused 57%, 28%, 86% and 81% inhibition in Anti-CD69 to CD69 coated wells. This reduction in ELISA O.D.s or anti-CD26 or anti-CD69 binding to CD26 or CD69, is an indication of gliadin, casein, SK and mercury binding to CD26 and CD69 (Table 2).

TABLE 2

Inhibition of anti-CD26 and anti CD-69 by gliadin, casein, streptokinase and ethyl mercury which reflects the binding of these molecules to CD26 and CD69 coated plates.

| Microwell Coated With: | Peroxidase Labeled Rabbit Anti: | ELISA O.D. at 492 nm | % Binding of Gliadin, Casein, Streptokinase, or Mercury to CD26 and CD69 |
|---|---|---|---|
| BSA + HSA | CD26 | 0.28 | B.G. |
| BSA + HSA | CD69 | 0.24 | B.G. |
| BSA + HSA | Gliadin | 0.31 | B.G. |
| BSA + HSA | Casein | 0.29 | B.G. |
| BSA + HSA | SK | 0.33 | B.G. |
| CD26 + BSA + HSA | CD26 | 2.16 | — |
| CD26 + Gliadin | CD26 | 1.19 | 52 |
| CD26 + Casein | CD26 | 1.34 | 44 |
| CD26 + SK | CD26 | 0.72 | 77 |
| CD26 + Ethyl Mercury | CD26 | 0.79 | 73 |
| CD69 + BSA + HSA | CD69 | 1.92 | — |
| CD69 + Gliadin | CD69 | 0.97 | 57 |
| CD69 + Casein | CD69 | 1.45 | 28 |
| CD69 + SK | CD69 | 0.48 | 86 |
| CD69 + Ethyl Mercury | CD69 | 0.56 | 81 |

BG = background

Binding of SK Gliadin and HSP-60 to DPP IV and Other Enzymes or Receptors

In additional experiments, we showed that bacterial toxins and heat shock proteins could promote development of peptidase antibodies in children with autism and patients with autoimmune disease. In these experiments, by searching for a mechanism underlying autoimmunity in autism, we postulated that gliadin peptides, heat shock protein (HSP-60) and streptokinase (SK) bind to different peptidases. Binding results in autoimmunity. We assessed this hypothesis in patients with autism and in those with mixed connective tissue diseases. Concomitant with the appearance of anti-gliadin and anti-HSP antibodies, children with autism, and patients with autoimmune disease developed anti-DPPI, anti-DPP IV and anti-CD 13 autoantibodies. These antibodies may be synthesized as a result of gliadin and HSP-60 binding to different peptidases since a significant percentage of autoimmune and autistic sera were associated with elevated IgG, IgM or IgA antibodies against all three peptidases, gliadin and HSP-60. These antibodies are specific since immune absorption demonstrated that only specific antigens (i.e., DPP IV absorption of anti-DPP IV significantly reduced IgG, IgM and IgA antibody levels). For direct demonstration of SK, HSP-60 and gliadin peptides binding to DPP IV, microtiter wells were coated with DPP IV and with SK, HSP-60 and gliadin. Finally they were reacted with rabbit anti-DPP IV, or anti-SK, anti-HSP-60 and anti-gliadin. Addition of SK, HSP-60 and gliadin peptides to DPP IV resulted in 27-43% inhibition of DPP IV anti-DPP IV reaction. Furthermore, addition of anti-SK, anti-HSP-60 and anti-gliadin to DPP IV+peptides caused 18-20% enhancement of antigen-antibody reaction. These results further support: binding of SK, gliadin and HSP to DPP IV. We propose that superantigens (e.g., SK, HSP-60), dietary proteins (e.g., gliadin peptides) in individuals with predisposing HLA molecules bind to aminopeptidases and induce autoantibodies against peptides and tissue antigens. From our results we conclude that binding of bacterial superantigens to DPP IV, DPP I or CD13 can be responsible for autoantibody production in children with autism and in patients with autoimmune diseases (12, 14, 15).

TABLE 3

Percent Elevation of Antibodies Against DPP IV, DPPI, CD13, Gliadin Peptidase and HSP-60 in Controls and Patients with Autism and Autoimmune Disease

| | % IgG Elevation in: | | | | % IgM Elevation in: | | | | % IgA Elevation in: | | | |
|---|---|---|---|---|---|---|---|---|---|---|---|---|
| ANTIGENS | Children Control | Autism | Adults Control | Auto-immune | Children Control | Autism | Adults Control | Auto-immune | Children Control | Autism | Adults Control | Auto-immune |
| DPP IV | 10 | 54 | 14 | 64 | 8 | 50 | 8 | 46 | 6 | 44 | 4 | 58 |
| DPP I | 8 | 56 | 14 | 60 | 10 | 46 | 16 | 54 | 10 | 46 | 14 | 56 |
| CD13 | 8 | 40 | 6 | 28 | 6 | 18 | 6 | 18 | 12 | 48 | 8 | 50 |
| Gliadin Peptide | 12 | 42 | 18 | 62 | 8 | 50 | 20 | 48 | 6 | 44 | 18 | 52 |
| HSP-60 | 16 | 36 | 22 | 52 | 8 | 44 | 18 | 48 | 14 | 50 | 14 | 42 |

TABLE 4

Multiple Comparisons and Means for Groups in Homogenous Subsets with Scheffe's Post Hoc Tests

| | SUBSET | | | | SUBSET | | | | SUBSET | |
|---|---|---|---|---|---|---|---|---|---|---|
| | 1 | 2 | 3 | | 1 | 2 | 3 | | 1 | 2 |
| A. DPP IV IgG in: | | | | A. DPP IV IgM in: | | | | A. DPP IV IgA in: | | |
| Control-Children | .1432 | | | Control-Children | .1694 | | | Control-Children | .1336 | |
| Control-Adults | .1994 | | | Control-Adults | .1826 | | | Control-Adults | .1654 | |
| Autism | | .3488 | | Autism | | .3260 | | Autism | | .3620 |
| Autoimmune | | .4282 | | Autoimmune | | .3700 | | Autoimmune | | .5120 |
| B. DPP I IgG in: | | | | B. DPPI IgM in: | | | | B. DPP I IgA in: | | |
| Control-Children | .1446 | | | Control-Children | .1492 | | | Control-Children | .1508 | |
| Control-Adults | .1492 | | | Control-Adults | .1480 | | | Control-Adults | .1546 | |
| Autism | | .3580 | | Autism | | .2980 | | Autism | | .3320 |
| Autoimmune | | .3940 | | Autoimmune | | | .4300 | Autoimmune | | .4560 |
| C. CD13 IgG in: | | | | C. CD13 IgM in: | | | | C. CD13 IgA in: | | |
| Control-Children | .1432 | | | Control-Children | .1310 | | | Control-Children | .1484 | |
| Control-Adults | .1994 | | | Control-Adults | .1400 | | | Control-Adults | .1218 | |
| Autism | | .2900 | | Autism | .1700 | | | Autism | | .4040 |
| Autoimmune | | .2460 | | Autoimmune | .1680 | | | Autoimmune | | .3900 |
| D. Gliadin Peptide IgG in: | | | | D. Gliadin Peptide IgM in: | | | | D. Gliadin Peptide IgA in: | | |
| Control-Children | .1640 | | | Control-Children | .1460 | | | Control-Children | .1454 | |
| Control-Adults | .2140 | .2120 | | Control-Adults | .1920 | | | Control-Adults | .1860 | |
| Autism | | .3600 | .3600 | Autism | | .3580 | | Autism | | .3680 |
| Autoimmune | | | .5060 | Autoimmune | | .4640 | | Autoimmune | | .4520 |
| E. HSP-60 Peptide IgG in: | | | | E. HSP-60 Peptide IgM in: | | | | E. HSP-60 Peptide IgA in: | | |
| Control-Children | .1620 | | | Control-Children | .1300 | | | Control-Children | .1618 | |
| Control-Adults | .1980 | | | Control-Adults | .1770 | .1770 | | Control-Adults | .1636 | |
| Autism | .2800 | | | Autism | | .3380 | .3380 | Autism | | .6100 |
| Autoimmune | | .5020 | | Autoimmune | | | .4880 | Autoimmune | | .5820 |

NOTES:
Means for groups in homogenous subsets are displayed based on type III sum of squares (sample size of 200, with 50 subjects in each group). Means that are reported in the same subset are statistically similar. For example, means for IgG (DPP I) for the control-children and control-adults groups are .1446 and .1492, respectively, which are statistically alike. Similarly, the means for the autism (.3580) and autoimmune groups (.3940) are statistically the same. However, the means for control-children are significantly different from the autism or autoimmune group. Similarly, the means for the control-adults are statistically different from both the autism and autoimmune groups. Also note that the control groups (.1492 & .1480) are similar for IgM (DPP I), but autism (.2980) and autoimmune (.4300) are not statistically alike. Potentially, up to four subsets could be formed, simply because for each dependent variable we have four experimental groups. When this is the case each mean's group should be reported in a separate subset. However, if all four means are statistically alike, all should be reported in one subset. For example, for CD13 IgM, all means are reported in the sample subset, indicating that no difference between the four groups was detected.

Table 5 shows percent elevation of IgG, IgM, and IgA antibody levels against digestive enzymes, tissue enzymes, lymphocyte receptors, neuroimmune communicators, gliadin peptides, casein peptides, bacterial antigens, bacterial toxins, and ethyl mecury in controls and children with autism at a cut-off of 2 standard deviations above the mean of controls.

TABLE 5

Percent Elevation of IgG, IgM, and IgA Antibody Levels Against Digestive Enzymes, Tissue Enzymes, Lymphocyte Receptors, Neuroimmune Communicators, Gliadin Peptides, Casein Peptides, Bacterial Antigens, Bacterial Toxins, and Ethyl Mercury in Controls and Children with Autism at a Cut-Off of 2 Standard Deviations above the Mean of Controls

| Antigen | IgG | | IgM | | IgA | |
|---|---|---|---|---|---|---|
| | Controls | Patients | Controls | Patients | Controls | Patients |
| DPP IV | 14 | 54 | 10 | 50 | 8 | 44 |
| DPPI | 14 | 56 | 12 | 46 | 10 | 46 |
| CD13 | 8 | 40 | 8 | 18 | 10 | 48 |
| CD69 | 6 | 36 | 4 | 28 | 4 | 46 |
| Pepsin | 4 | 38 | 2 | 32 | 4 | 42 |
| Trypsin | 6 | 44 | 4 | 36 | 6 | 48 |
| Chymotrypsin | 8 | 48 | 6 | 38 | 8 | 46 |
| Secretin | 12 | 52 | 8 | 40 | 10 | 50 |
| Transglutaminase | 10 | 44 | 6 | 42 | 8 | 42 |
| Gastrin | 12 | 46 | 8 | 34 | 6 | 38 |
| Motilin | 14 | 52 | 12 | 48 | 12 | 46 |
| Vasoactive Intestinal peptide | 8 | 48 | 6 | 32 | 10 | 52 |
| Oxytocin | 6 | 32 | 4 | 24 | 6 | 32 |
| Glucose regulated protein | 4 | 28 | 2 | 18 | 2 | 24 |
| Tropomyosin | 8 | 36 | 4 | 26 | 4 | 32 |
| Gliadin peptides | 8 | 42 | 8 | 50 | 10 | 44 |
| Casein peptides | 10 | 42 | 8 | 34 | 8 | 42 |
| Heat shock protein | 6 | 36 | 8 | 44 | 10 | 50 |
| Streptokinase | 2 | 18 | 4 | 48 | 2 | 24 |
| Ethyl Mercury | 4 | 28 | 2 | 30 | 0 | 10 |
| Serotonin | 6 | 30 | 8 | 36 | 12 | 46 |
| Enkephalin | 5 | 36 | 6 | 42 | 3 | 21 |
| MBP | 15 | 58 | 18 | 73 | 14 | 5 |
| PLP | 7 | 46 | 5 | 39 | 4 | 37 |
| Transaldolase | 4 | 29 | 2 | 21 | 1 | 19 |
| MOG | 11 | 48 | 19 | 63 | 9 | 40 |
| MAG | 8 | 49 | 11 | 62 | 4 | 27 |
| Sodium channel | 6 | 38 | 5 | 33 | 3 | 28 |
| Glutamate receptor | 4 | 42 | 6 | 39 | 2 | 31 |
| Cerebellar | 5 | 49 | 3 | 41 | 4 | 35 |
| Amyloid β | 1 | 23 | 2 | 20 | 1 | 15 |
| Tubulin | 8 | 49 | 10 | 63 | 10 | 42 |
| Neurofilaments | 4 | 48 | 8 | 58 | 9 | 38 |
| Zinc finger protein | 1 | 34 | 2 | 27 | 1 | 22 |
| Somatostatin | 3 | 39 | 2 | 34 | 1 | 26 |
| C-jejuni | 4 | 44 | 3 | 38 | 2 | 27 |
| Pancreatic polypeptide | 3 | 27 | 2 | 25 | 0 | 15 |
| B-Endorphin | 5 | 36 | 3 | 32 | 0 | 18 |
| Endothelin | 2 | 35 | 1 | 27 | 1 | 0 |
| Dynorphins | 2 | 37 | 1 | 30 | 0 | 16 |
| Seretonin receptor | 3 | 36 | 3 | 28 | 1 | 22 |
| Fibrillarin | 2 | 44 | 1 | 40 | 1 | 27 |
| Calreticullin | 1 | 30 | 0 | 24 | 0 | 15 |

Antibodies Against Neuron-Specific Antigens in Autism

Until recently, there has been little direct evidence readily available in support of the molecular mimicry hypothesis and to clearly delineate the role of infectious agents as a cause for neurological disorders. For example, studies in mice have shown that infection with Theiler's virus elicits an inflammatory response in the CNS that progresses to chronic experimental autoimmune encephalomyelitis (28). Epitopes of Streptococcal M proteins have also been shown to evoke antibodies that cross-react with human brain neuronal cell basal ganglia, which are potentially involved in the pathogenesis of Sydenham's chorea (associated with acute rheumatic fever). Very recently, a rather elaborate experiment of a well-characterized rat model of MS has been used to investigate the casual relationship between infections and MS. Investigators identified a 20-mer peptide from a protein specific to *C. pneumonia*, which shares a '7-amino acid motif with a critical epitope of myelin basic protein, a major CNS antigen targeted by the autoimmune response in MS. This bacterial peptide induces a Th1 response, accompanied by severe clinical and histological experimental autoimmune encephalomyelitis in Lewis rats, a condition closely reflective of many aspects of MS. Studies with peptide analogues suggest that different populations of encephalitogenic T cells are activated by the *C. pneumoniae* and myelin basic protein antigens (29, 30). Based on these findings and research, we hypothesized that if infectious antigens or toxic chemicals cause the blood-brain barrier to become more permeable, then antibodies (such as IgG, IgM, and IgA) to neurologic antigens or pathogenic peptides should be detectable in the blood of patients with autism.

To examine this hypothesis, we used different purified protein and synthetic peptides in a highly specific, in-house ELISA procedure with a low background of smaller than 0.1 O.D. at 492. Another advantage of this assay is the use of a second antibody, such as antihuman IgG, IgM or IgA, for identification of antibody isotypes. In many autoimmune diseases (including autoimmune neurological disorders), the isotypes IgM and IgA autoantibodies are considered to be more pathogenic than the IgG isotype. As shown in Table 6, it was found that all three isotype antibodies, whether alone or in combination, exhibited higher levels in autistic patients than in healthy control subjects. The purified protein and synthetic peptides include myelin basic protein (MGP), myelin associated glycoprotein (MGP), ganglioside $GM_1$ ($GM_1$), sulfatide (SULF), chondroitin sulfate ($CONSO_4$), myelin oligodendrocytes glycoprotein (MOG), α, β-crystallin (α, β-CRYS), neuron-axon filament protein (NFB), glial fibrillary acidic protein (GFAP), tubulin, cerebellar purkinje cells (Cerebellar), glutamate receptor, ion channel, and transaldolase.

TABLE 6

Approximate Percent Elevation of IgG, IgM, and IgA Antibody Levels Against 13 Different Neural Antigens in Controls and Children with Autism at a Cut-Off of 2 standard deviations above the Mean of Controls

| Antigen | IgG Controls | IgG Patients | IgM Controls | IgM Patients | IgA Controls | IgA Patients |
|---|---|---|---|---|---|---|
| MBP | 14 | 57 | 16 | 61 | 12 | 48 |
| MAG | 9 | 49 | 12 | 56 | 5 | 29 |
| $GM_1$ | 6 | 52 | 9 | 59 | 3 | 37 |
| SULF | 4 | 51 | 13 | 64 | 6 | 41 |
| $CONSO_4$ | 7 | 46 | 12 | 60 | 5 | 42 |

TABLE 6-continued

Approximate Percent Elevation of IgG, IgM, and IgA Antibody Levels Against 13 Different Neural Antigens in Controls and Children with Autism at a Cut-Off of 2 standard deviations above the Mean of Controls

| Antigen | IgG Controls | IgG Patients | IgM Controls | IgM Patients | IgA Controls | IgA Patients |
|---|---|---|---|---|---|---|
| MOG | 11 | 43 | 11 | 58 | 7 | 39 |
| α, β-CRYS | 4 | 53 | 9 | 56 | 3 | 21 |
| NFβ and GFAP | 6 | 49 | 8 | 53 | 6 | 27 |
| Tubulin | 12 | 50 | 10 | 56 | 8 | 36 |
| Cerebellar | 5 | 41 | 7 | 46 | 4 | 26 |
| Glutamate receptor | 3 | 37 | 5 | 39 | 2 | 23 |
| Ion channel | 1 | 19 | 2 | 17 | 1 | 14 |
| Transaldolase | 4 | 33 | 3 | 29 | 2 | 26 |

This simultaneous elevation of IgG, IgM and IgA antibodies against multiple neurological antigens indicates that an alteration of the blood-brain barrier by infectious agent antigens promotes the access of immunocompetent cells to many different nervous system antigens. Thus, immune cell reaction to the nervous system antigens is not limited only to neuronal and glial filament, but also against many other nervous system antigens. See Vojdani et al., 2002, in the *Journal of Neuroimmunology*, vol. 129, pages 168-177, hereby incorporated by reference.

Simultaneous Detection of Antibody Against Glaidi and Cerebellar Peptides

By studying amino acid sequences of a-gliadin several peptides in particular a 33 mer was discovered to be responsible for cellular and humoral immune reactions in celiac disease. These gliadin peptides share between 20-30% similarity with cerebellar Purkinje cell antigens. Therefore, we developed peptide based ELISA assays for measuring antibodies against gliadin and cerebellar peptides simultaneously in children with autism.

Sera from 50 patients with autism were measured for simultaneous presence of IgG, IgM and IgA antibodies against gliadin and cerebellar peptides and compared to healthy controls. Results summarized showed that at 2 S.D. above the mean of controls, while 21 or 42% of patients with autism had elevated antibody levels against gliadin peptides, only 6 or 12% of control subjects had elevated antibodies against all these peptides. In comparison 18 or 36% of patients and 4 or 8% of controls demonstrated significantly elevated antibodies against cerebellar peptides. 17 of 21 subjects (80%) of patients with autism had simultaneous elevation in anti-gliadin and anti-cerebellar peptides, indicating cross-reaction between gliadin and cerebellar antigen, which results in these antibodies in a majority of gliadin reactive patients with autism.

Based on this antigenic similarity between milk butyrophilin, casein and gliadin peptides with myelin basic protein, myelin oligodendrocyte glycoprotein and cerebellar Purkinje cells, a casein and gliadin-free diet may be recommended for individuals with elevated milk and gliadin IgG, IgM or IgA antibodies.

In summary, we learn that autoantibodies to different tissue antigens in autism are produced by two different mechanisms of action: 1) by direct binding of infectious agent antigens or peptides, dietary proteins or peptides, or by binding of xenobiotics or their metabolites to tissue enzymes or cell receptors, inducing antibody production against the tissue antigens as well as bacterial, dietary or xenobiotics; and 2) many infectious agents, dietary proteins, and peptides share similar epitopes with different tissue antigens. Therefore, immune responses against the infectious agents or dietary proteins result in autoimmune reactions with different tissue antigens, including brain cells. Based on these findings, we postulate that dietary and infectious antigens as well as xenobiotics play a role in the pathophysiology of autism. It is likely that environmental factors, including infection-induced injury, cause the release of neuronal antigens, which, through activation of inflammatory cells, could lead to autoimmune reactions in genetically susceptible individuals.

Since there is no single medical or laboratory marker that could be used for the diagnosis or follow-up treatment of children with autism, a protocol of testing for autistic spectrum disorders can further comprise: 1) assessment of immune function and imbalance in T-helper-1/T-helper-2 cytokines; 2) gut integrity or intestinal barrier function tests; 3) protection by metallothionein; and 4) assessment of serotonin level.

Assessment of Immune Function

These immune assays are recommended since strong lines of evidence suggest that the immune system plays an important role in the development of autism. Immune abnormalities in autism include changes in the numbers and activities of macrophages, T-cells, B-cells, and natural killer cells. Furthermore, a shift occurs from T-helper-1 to T-helper-2 T-cell type in autism as evidenced by a decrease in the production of Interleukin-2 (IL-2) and interferon-γ (IFN-γ) and an increased production on Interleukin-(IL-4). In other abnormalities in immune function, cytokine production and immunoglobulin levels may justify the use of intravenous immunoglobulin (IVIG) treatment or the use of biological response modifiers for regulation of the immune system. Tests for immune function include, but are not limited to, assessment of the following: Lymphocyte Subpopulation Analysis, Lymphocyte Immune Function Test, Natural Killer Cell Cytotoxic Activity, Immunoglobulins, T-Helper 1/T, C3 Complement, and C4 Complement.

Gut Integrity or Intestinal Barrier Function Tests

The intestinal barrier function test was developed since mucosal barrier dysfunction may result in gastrointestinal, cardiovascular, systemic immunity and autoimmunity.

Human beings harbor an incredibly complex and abundant ensemble of microbes. These resident bacteria shape our physiology in many ways. To investigate the importance of commensal bacteria in gastrointestinal health, germ-free mice were colonized with bacteroides and intestinal transcriptional responses were measured using DNA microarrays. Colonized bacteria modulated expression of genes involved in important intestinal function including:

1. Nutrient absorption
2. Lipid absorption capacity
3. Mucosal barrier fortification
4. Xenobiotic metabolism
5. Angiogenesis
6. Postnatal intestinal maturation This shows the importance of host-microbial relationships in the GI tract and how gut bacteria and their products play a role in the induction and expression of normal immune responses, suggesting that changes in this flora may mediate abnormalities of system immunity.

In addition to measurement of antibodies against dietary proteins, yeast, aerobic and anaerobic bacteria, antibodies against secretin are measured. Similar to DPP IV, secretin is involved not only in digestion of peptides but also in neuroimmune communication. Therefore, demonstration of antibodies against secretin or DPP IV may justify enzyme replacement in children with autism.

The intestinal barrier function test was developed since, in our experience, microflora imbalance, intestinal barrier dysfunction, humoral immune deficiency, food allergy and autoimmunity cannot be fully understood in their diagnostic and therapeutic implications without coordination of all the components of the intestinal flora (yeast, aerobic bacteria, anaerobic bacteria, and dietary antigens).

Many of these conditions that adversely affect the intestinal flora have been mistakenly called "The Yeast Problem" and are tested by stool culture. While stool culture is a very powerful technique for detection of pathogenic bacteria, it may not detect any gastrointestinal microflora imbalance, since these organisms tend to bind to receptor sites on epithelial cells and secrete endotoxins, which damage local and distant tissues.

This systemic translocation of enteric bacteria and yeast plays a major role in the development of abnormal systemic immunity, which may result in multiple organ failure. As mentioned before, excessive uptake of bacterial, fungal, viral and food antigens into the circulation may induce immune response first in the form of IgM and, thereafter, in the form of IgG and IgA antibodies, which results in clinical conditions. For this reason, measurement of circulating IgM, IgG and IgA antibodies against specific antigens of intestinal bacterial and fungal flora is of considerable importance in the pathogenesis of immunologically mediated diseases including food allergies and autoimmunities. Again, this is the basis of our "Intestinal Barrier Function Test".

In this test, we utilize a highly sensitive and accurate ELISA test method that measures the serum IgG, IgM and IgA specific antibody titers to the purified antigens from five different dietary proteins, three aerobic, two anaerobic microbes and a mixture of three different *Candida* species (*Candida albicans, Candida tropicalis* and *Candida krusei*).

Such quantitative and comparative test results may allow the determination of primary clinical conditions such as:

Food allergy
Intestinal Imbalance
Gut barrier dysfunction
Bacterial translocation
Immunodeficiencies
Candidiasis
Autoimmunities Intestinal barrier dysfunction may lead to polarized immune function, which may result in food allergy and intolerance. The intestinal immune system is characterized by a distinct profile of cells, adhesion molecules, cytokines and chemokines. In addition, it has a predisposition to the induction of tolerance and bias towards productive or protective immunity that are dominated by production of IgA antibodies against food and commensal antigens. However, it is not clear why intestinal microenvironment results in polarized immune function.

Figure 7:
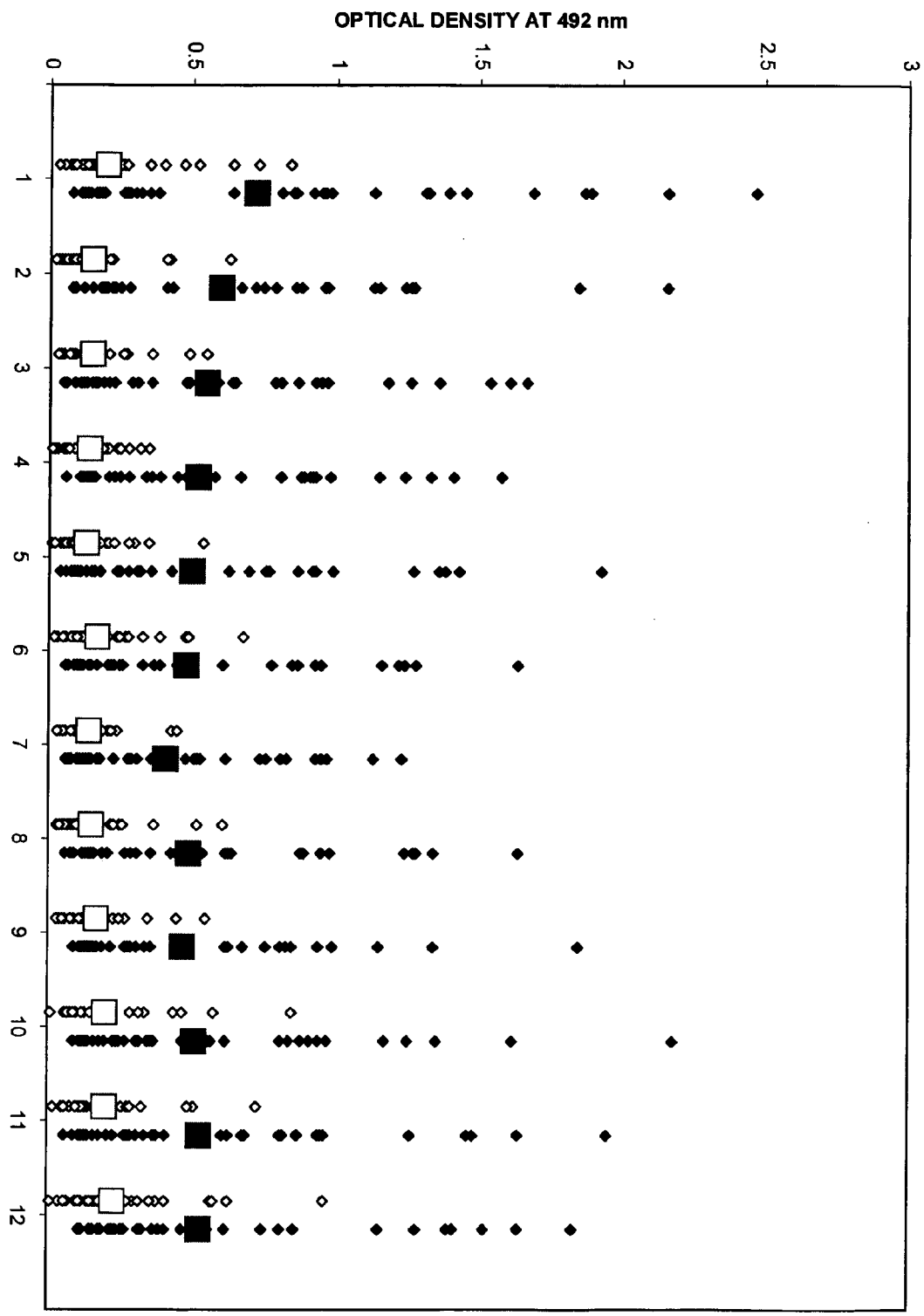
FIG. 7 shows a scattergram of serum titer of IgG antibody against different neurologic antigens (1-MBP, 2-MAG; 3-GM1; 4-SULF; 5-CONSO4; 6-MOG; 7-b-CRYS; 8-NAFP; 9-TUBULIN) and their cross-reactive peptides (10-CPP; 11-STM6P; 12-MILK-BTN) in healthy control subjects (40) and patients with autism (40) expressed as optical density in ELISA test.
Figure 8:
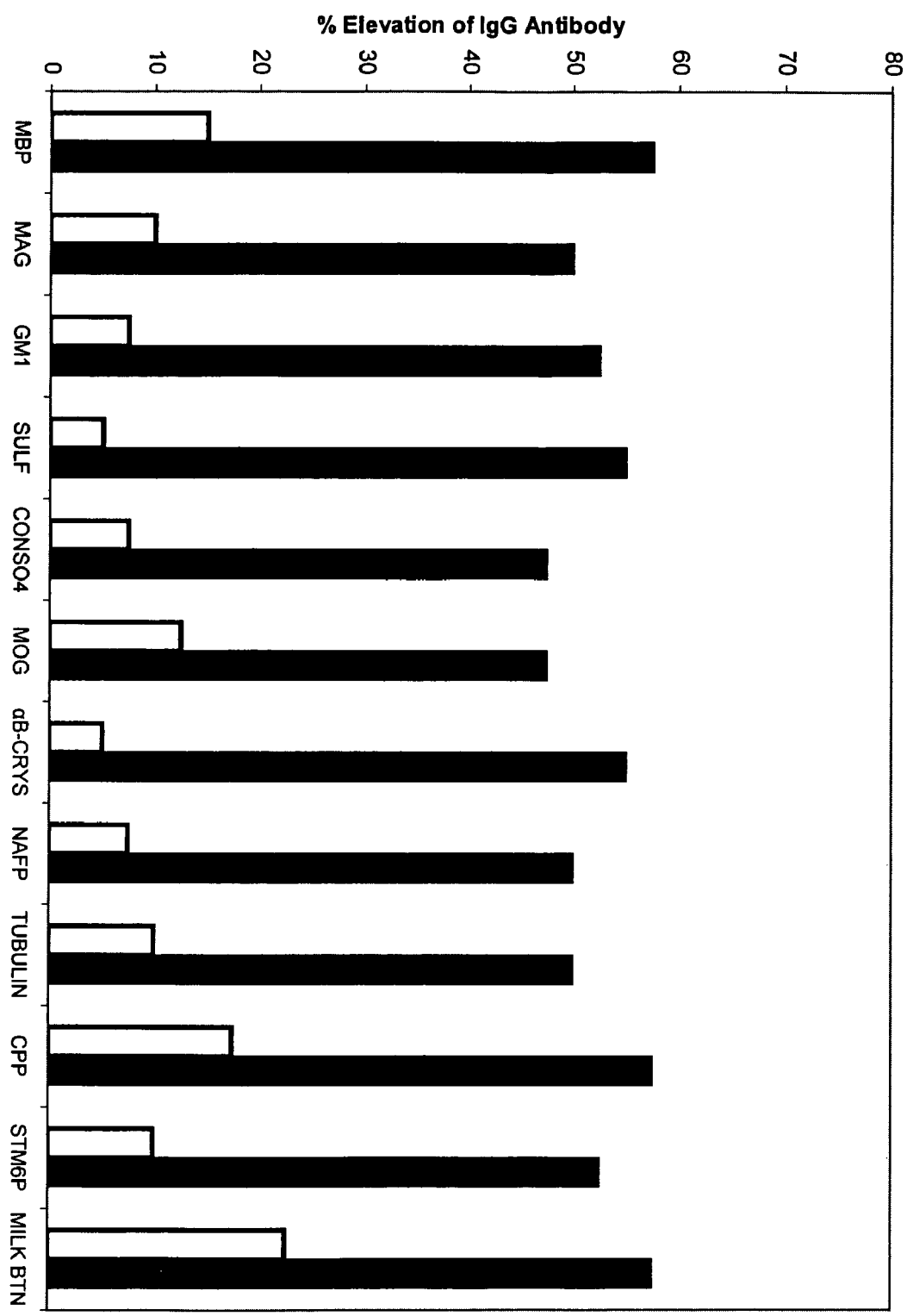
FIG. 8 shows percent elevation in IgG antibody against neurologic antigens and their cross-reactive peptides in healthy control subjects (40) and patients with autism (40) at cut-off point of 0.30 O.D.

It is believed that food proteins and antigens of commensal bacteria are taken up by immunoregulatory dendritic cells (DCs). In the absence of inflammation, prostaglandin $E_2$ ($PGE_2$) is produced by mesenchymal cells and macrophages. Transforming growth factor-β TGF-β) and IL-10 is produced by epithelial cells, resulting in the maturation of DCs in the Peyer's path or *Lamina properia*. These food and bacterial antigens are then presented to the naive CD4+ T-cells in mesenteric lymph nodes or Peyer's patch. These T-cells differentiate into regulatory T-cells, which produce interferon-γ and IL-10 or differentiate into T-helper-3 cells, which produce TGF-β. The immunological consequences are local IgA production, local immune homeostasis and systemic tolerance. However, when the body encounters pathogens, xenobiotics or some dietary peptides in the presence of inflammation, mesenchymal cells and macrophages not only fail to produce $PGE_2$ but they also express toll-like receptors. As a result, DCs in the Peyer's patch or *Lamina propria* become completely mature, taking up the antigen(s) and producing significant amounts of IgG, IgM and IgA antibodies against milk protein, milk peptides (casomorphin), wheat, corn and soy proteins, wheat peptides (gliadin peptides), gluteomorphins, and tissue enzymes (transglutaminase, DPP IV, aminopeptidases) (FIGS. 7, 8). Significant elevations in IgG, IgM or IgA antibodies against dietary proteins or peptides and their target tissue antigens (brush border enzymes) may justify treatment with the elimination diet and enzyme replacement or both. The Intestinal Barrier Function Test, disclosed in U.S. Pat. No. 6,103,480, herein incorporated by reference, can include assessment of the following: Dietary Proteins (IgG, IgM, IgA), Yeast (IgG, IgM, IgA), Aerobic Bacteria (IgG, IgM, IgA), Anaerobic Bacteria (IgG, IgM, IgA), and Secretin (IgG, IgM, IgA).

Functional Metallothioneins Assay

Metallothioneins (MTs) have a major role to play in metal metabolism, and may also protect DNA against oxidative damage. MT protein has been found localized in the nucleus during S-phase.

MTs are a family of low-molecular-mass metal-binding protein isoforms. Although considered mainly cytoplasmic, MT has been found localized in the nucleus of the cell under different physiological conditions. For example, during the $G_1$-to-S-phase transition of the cell cycle or following metal toxicity, MT is found specifically in the nucleus. The function of MT in the nucleus is in protecting against metal toxicity and the harmful effects of oxidative stress, DNA damage and apoptosis induced by external stress.

Therefore, only the cellular activity of metallothionein is important for the assessment of metal-induced toxicity. The binding of metals to metallothionein may also result in autoantibody production against metallothionein in the nucleus.

Based on this information, the following panel were developed for determining etiology, and management of autism;

Since there is no single medical or laboratory marker that could be used for the diagnosis or follow-up treatment of children with autism. Therefore, one embodiment comprises a protocol of testing for autistic spectrum disorders can include a panel of tests chosen from the categories outlined in the next section, including Autism Panel—Short, Neuroimmunology of Autism Panel, Comprehensive Panel of all tests performed for autism.

| AUTISM PANEL - SHORT | |
| --- | --- |
| Streptococcal Antigens | (M5+, M12+, M19) (IgG, IgM, IgA) |
| Measles Antibodies | (IgG, IgM, IgA) |
| HHV-6 | (IgG, IgM, IgA) |
| Gliadin Peptides Antibodies | (IgG, IgM, IgA) |
| Casein Peptides Antibodies | (IgG, IgM, IgA) |

-continued

| | |
| --- | --- |
| Fibrillarin | (IgG, IgM, IgA) |
| Dipeptidylpeptidase | (DPP IV) Antibodies (IgG, IgM, IgA) |
| Myelin Basic Protein Antibodies | (IgG, IgM, IgA) |
| Neurofilament Antibodies | (IgG, IgM, IgA) |
| NEUROIMMUNOLOGY OF AUTISM PANEL | |
| Antibodies to Dietary Proteins & Peptides (Food Allergy & Autoimmunity) | |
| Corn | (IgG, IgM, IgA) |
| Milk | (IgG, IgM, IgA) |
| Soy | (IgG, IgM, IgA) |
| Wheat Gluten/Gliadin | (IgG, IgM, IgA) |
| Casomorphin | (IgG, IgM, IgA) |
| Gluteomorphin | (IgG, IgM, IgA) |
| Secretin | (IgG, IgM, IgA) |
| Prodynorphin + Dynorphin | (IgG, IgM, IgA) |
| Antibodies to Infectious Agents | |
| Clostridium Neurotoxin | (IgG, IgM, IgA) |
| Herpes Type 6 | (IgG, IgM, IgA) |
| Rubeola (Measles) | (IgG, IgM, IgA) |
| Neurotoxicity and Autoimmune Reaction to Neuronal Cell Antigens | |
| Myelin Basic Protein | (IgG, IgM, IgA) |
| Neurofilament | (IgG, IgM, IgA) |
| Neurotransmitters and Signal Transduction | |
| Serotonin Antibodies | (IgG, IgM, IgA) |
| Serotonin Receptor Antibodies | (IgG, IgM, IgA) |
| Somatostatin Antibodies | (IgG, IgM, IgA) |
| Dipeptidylpeptidase IV (CD26) | (IgG, IgM, IgA) |
| COMPREHENSIVE PANEL OF ALL OF THE FOLLOWING TEST GROUPS: FOOD ALLERGY AND INTOLERANCE | |
| Antibody Testing on Blood | |
| Milk | (IgG, IgM, IgA) |
| Casomorphin | (IgG, IgM, IgA) |
| Wheat Gluten/Gliadin | (IgG, IgM, IgA) |
| Gluteomorphin | (IgG, IgM, IgA) |
| Transglutaminase | (IgG, IgM, IgA) |
| Corn | (IgG, IgM, IgA) |
| Soy | (IgG, IgM, IgA) |
| INFECTIOUS AGENTS AND RESPONSE TO VACCINATIONS | |
| Measles (Rubeola) | (IgG, IgM, IgA) |
| Mumps | (IgG, IgM, IgA) |
| Rubella | (IgG, IgM, IgA) |
| Diphtheria Toxoid | (IgG, IgM, IgA) |
| Pertussis | (IgG, IgM, IgA) |
| Tetanus Toxoid | (IgG, IgM, IgA) |
| Hepatitis B | (IgG, IgM, IgA) |
| Herpes Type 6 | (IgG, IgM, IgA) |
| Clostridium Neurotoxin | (IgG, IgM, IgA) |
| NEURO-AUTOIMMUNE ANTIBODIES INDUCED BY DIETARY PROTEINS AND INFECTIOUS AGENTS | |
| Myelin Basic Protein | (IgG, IgM, IgA) |
| Neurofilament | (IgG, IgM, IgA) |
| Milk Butyrophilin | (IgG, IgM, IgA) |
| Streptococcus M Protein | (IgG, IgM, IgA) |
| Chlamydia pneumoniae | (IgG, IgM, IgA) |
| AUTOIMMUNE REACTION AND INVOLVEMENT OF METALS | |
| Mercury | (IgG, IgM, IgA) |
| Fibrillarin | (IgG, IgM, IgA) |
| Chromatin | (IgG, IgM, IgA) |
| Immune Complexes | (IgG, IgM, IgA) |
| Metallothionein | (IgG, IgM, IgA) |
| NEUROTRANSMITTERS AND ANTIBODIES | |
| Serotonin Receptor Antibodies | (IgG, IgM, IgA) |
| Serotonin Antibodies | (IgG, IgM, IgA) |
| Somatostatin Antibodies | (IgG, IgM, IgA) |

-continued

| | |
|---|---|
| Vasoactive Intestinal Peptide | (IgG, IgM, IgA) |
| Prodynorphin + Dynorphin | (IgG, IgM, IgA) |
| Dipeptidylpeptidase IV (CD26) | (IgG, IgM, IgA) |

The disclosure below is of specific examples setting forth preferred methods for embodiments. These examples are not intended to limit the scope, but rather exemplify preferred embodiments.

Example 1

Antibodies to Neuron-Specific Antigens in Children with Autism: Possible Cross-Reaction with Encephalitogenic Proteins from Milk, *Chlamydia Pneumoniae*, and *Streptococcus* Group A We detected antibodies against nine different neuron-specific antigens in the sera of children with autism. These antibodies were found to bind with different encephalitogenic molecules, which have sequence homologies with neurological antigens (butyrophilin, a milk protein; *Chlamydia pneumoniae* peptide; and *Streptococcus M* proteins). Our results suggest a role for antibodies against brain cross-reactive food antigens and infectious agents in the pathogenesis of autistic behavior.

Materials and Methods

Patients

Forty subjects (23 males and 17 females) 3 to 12 years of age (mean 6.4 years), with a diagnosis of autism were sent by different clinicians to our laboratory for immunogical examination. The clinical diagnosis of autism was made according to the DSM-IIIR criteria, established by the American Psychiatric Association, Washington D.C., as well as by a developmental pediatrician, a pediatric neurologist, and/or a licensed psychologist. Blood samples were excluded if their medical histories included head injury, evidence of gliomas, failure to thrive, and other known factors that may contribute to abnormal developmental. For comparison, blood samples from forty healthy, age and sex matched controls were included in this study.

Neuronal and Other Antigens

Myelin basic protein, myelin associated glycoprotein, ganglioside $GM_1$, α, β-crystallin, sulfatide, chondroitin sulfate and tubulin were purchased from Sigma Chemicals (St. Louis, Mo.). Neurofilament (NAFT) was purchased from Boehringer Mannheim Roche (Indianapolis, Ind.). MBP peptide 87-106, MOG peptides 21-40, 61-80, milk butyrophilin peptide 89-109, *Streptococcal M6* peptide, and *Chlamydia pneumoniae* peptide 483 bound to KLH were purchased from Research Genetics (Huntsville, Ala.).

ELISA Procedure

Enzyme-linked immunosorbent assay (ELISA) was used according to the above procedures.

Results

Detection of Neurologic Antibodies

Figure 9:
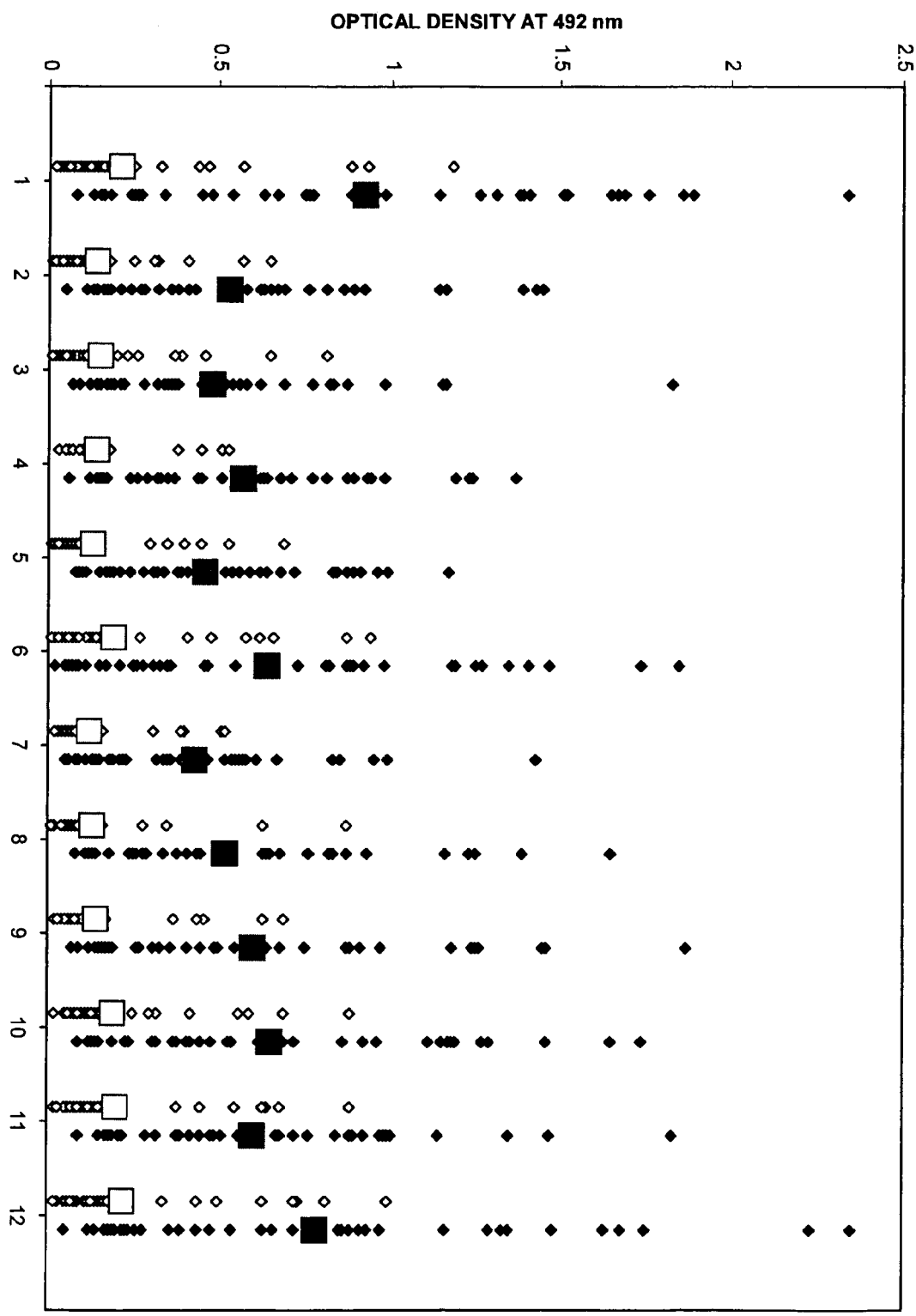
FIG. 9 shows a scattergram of serum titer of IgM antibody against different neurologic antigens (1-MBP, 2-MAG; 3-GMI; 4-SULF; 5-CONSO4; 6-MOG; 7-b-CRYS; 8-NAFP; 9-TUBULIN) and their cross-reactive peptides (10-CPP; 11-STM6P; 12-MILK-BTN) in healthy control subjects (40) and patients with autism (40) expressed as optical density in ELISA test.

Using ELISA assays, sera from 40 healthy subjects and 40 autistic children were analyzed for the presence of IgG, IgM, and IgA antibodies against neuron-specific antigens and three encephalitogenic and cross-reactive proteins. The ELISA results expressed as mean O.D. at 492 nm are summarized in FIG. 7. The O.D. for IgG antibody values obtained with 1:100 dilution of healthy control sera ranged from 0.01 to 0.84, varying among subjects and antigens. The mean±standard deviation (S.D.) of these O.D. values as shown in FIG. 9 ranged from 0.13±0.09 to 0.23±0.18. The corresponding IgG O.D. values from autistic children's sera ranged from 0.05 to 2.47 and with the mean±S.D. of IgG values, which ranged from 0.41±0.33 to 0.72±0.65 (FIG. 7). For all 12 antigens, the differences between mean±S.D. of control sera and autistic children's sera were highly significant ($p<0.001$). At a cutoff value of 0.3 O.D., levels of IgG antibody against these antigens were calculated in control and patient's sera and found that while 5-22.5% of control sera had IgG values higher than 0.3 O.D., the autistic children's group showed elevated IgG values from 47.5 to 57.5% ($p<0.001$) (FIG. 8).

Figure 10:
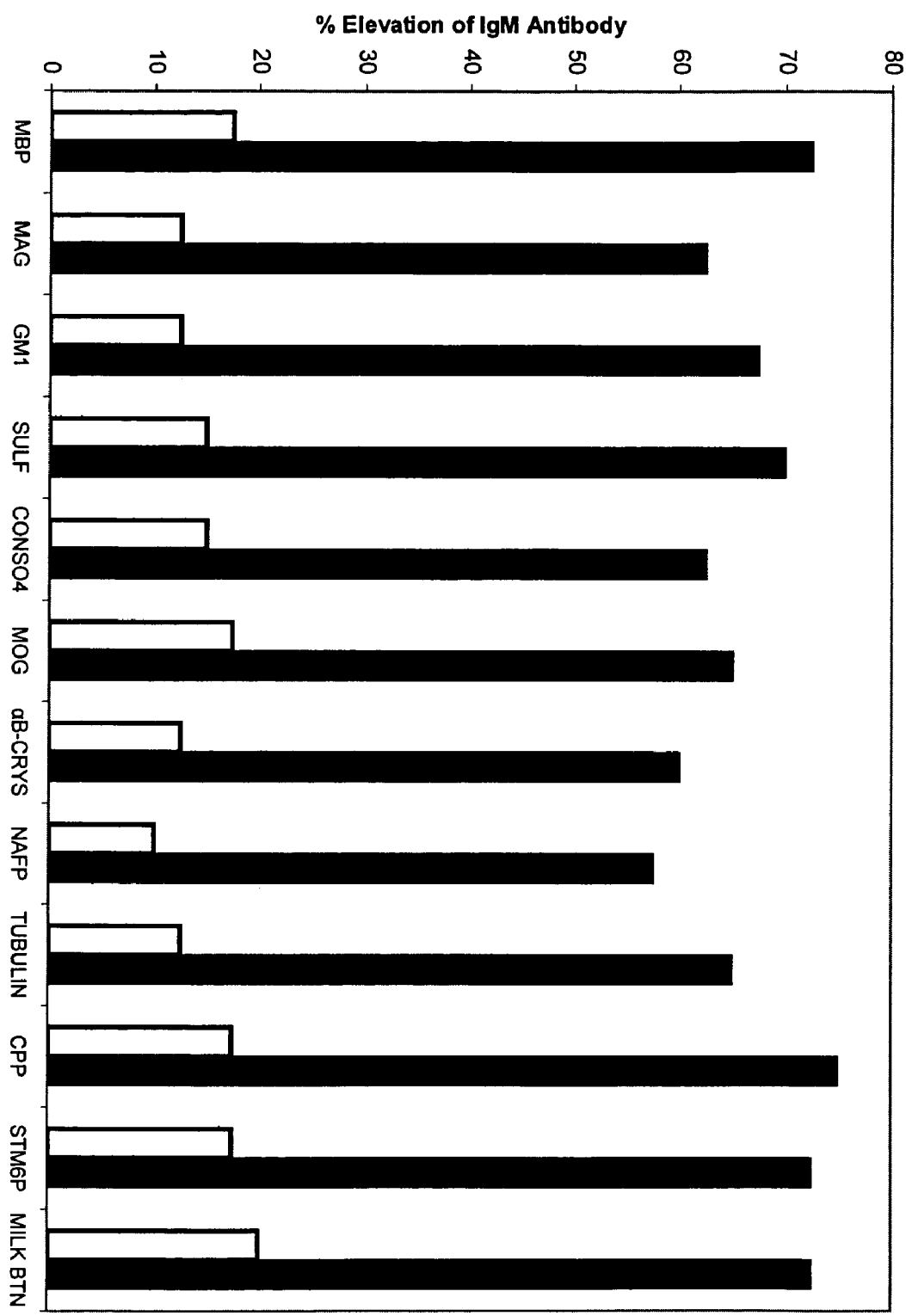
FIG. 10 shows percent elevation in IgM antibody against neurologic antigens and their cross-reactive peptides in healthy control subjects (40) and patients with autism (40) at cut-off point of 0.30 O.D.
Figure 11:
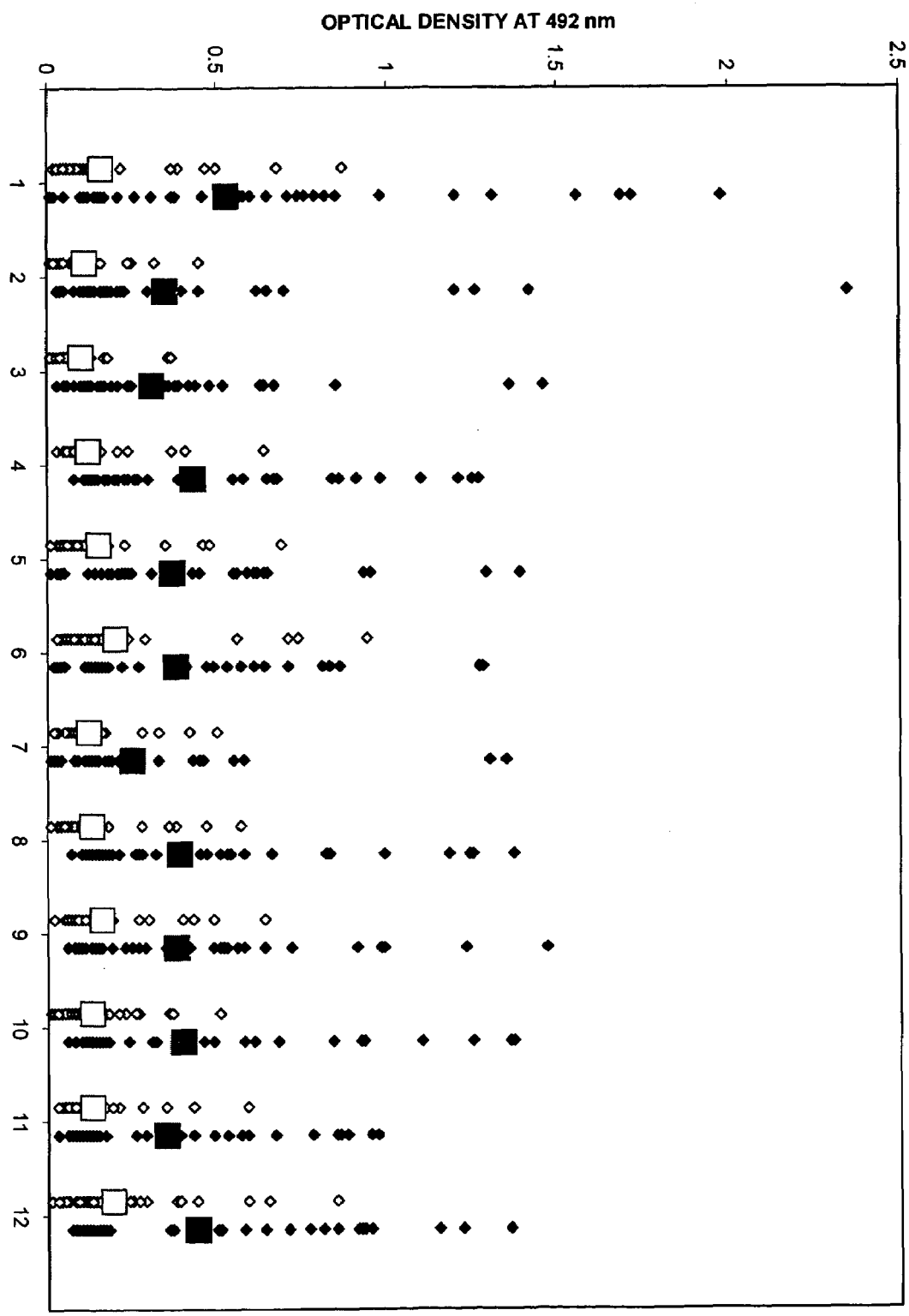
FIG. 11 shows a scattergram of serum titer of IgA antibody against different neurologic antigens (1-MBP, 2-MAG; 3-GMI; 4-SULF; 5-CONSO4; 6-MOG; 7-b-CRYS; 8-NAFP; 9-TUBULIN) and their cross-reactive peptides (10-CPP; 11-STM6P; 12-MILK-BTN) in healthy control subjects (40) and patients with autism (40) expressed as optical density in ELISA test.
Figure 12:
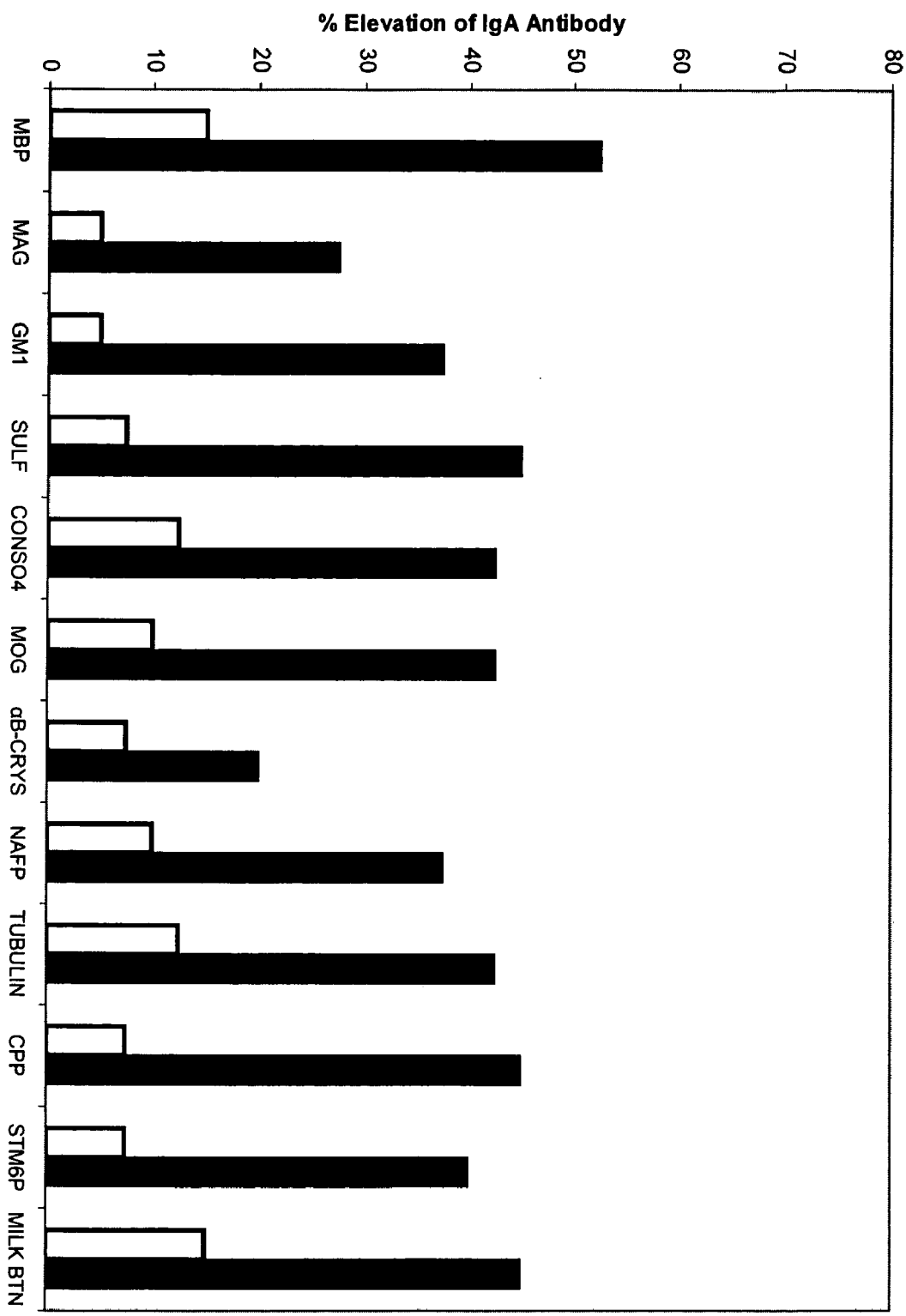
FIG. 12 shows percent elevation in IgA antibody against neurologic antigens and their cross-reactive peptides in healthy control subjects (40) and patients with autism (40) at cut-off point of 0.30 O.D.

Levels of IgM antineuron-specific antigens in sera of healthy controls and autistic children are shown in FIG. 9. These serum IgM antibodies against all 12 different tested antigens were significantly higher in patients than in controls. The mean±S.D. for controls ranged from 0.12±0.13 to 0.22±0.23 O.D. and for patients ranged from 0.43±0.32 to 0.92±0.63 OD ($p<0.001$) (FIG. 9). When the 0.3 O.D. cutoff point was used, 10 to 20% of controls versus 57.5 to 72.55% of autistic children's sera showed elevated IgM antibody levels ($p<0.001$) (FIG. 10). Likewise, IgA antibody levels against these neurological antigens were examined in both groups. Individual and mean±S.D. data depicted in FIG. 12 showed significant differences between control and patients groups. The mean±S.D. for IgA antibody levels in controls ranged from 0.10+0.07 to 0.2±0.22 and in patients, from 0.25±0.28 to 0.53±0.52 (FIG. 11) ($p<0.001$). Percent elevated serum IgA anti-neuronal autoantibodies at the O.D. value of greater than 0.3, were significantly higher in autistic children than in controls. The percent positive for IgA antibodies in controls ranged from 5 to 15% and in patients 20-52.5% ($p<0.001$) (FIG. 12).

Discussion

Indeed when we tested IgG, IgM, and IgA antibodies against these three peptides, we found that every single serum with ELISA values higher than 0.3 O.D. against neurological antigens exhibited high levels of antibodies against *Streptococcal, C. pneumoniae* and milk peptides as well (FIG. 9-12). Overall, antibodies against these three peptides (first IgM then IgG) were elevated in a higher percentage of controls and experimental sera than the percentage of elevated antibodies against neurological antigens. But, we did not observe even one specimen with a high antibody level against these peptides without having antibody levels against one or all nine tested neuron-specific antigens. These antibodies appear to be specific since in our absorption studies, milk butyrophilin, *C. pneumoniae* and *Streptococcal* peptide had a similar effect to MBP or MOG in reducing antibody levels from highly positive sera. Based on these findings, we postulate that dietary and infectious antigens play a role in the pathophysiology of autism. It is likely that environmental factors including infection-induced injury causes release of neuronal antigens, which through activation of inflammatory cells, could lead to autoimmune reactions in genetically susceptible individuals. However, only long-term studies can prove the protective versus pathogenic role of these antibodies in children with autism.

Example 2

Infections, Toxic Chemicals and Dietary Peptides Binding to Lymphocytes Receptors and Tissue Enzymes are Major Instigators of Autoimmunity in Autism Based on observations and since so little is known about the range of intestinal immune functions that are shaped by dietary proteins, xenobiotics and infectious agents in autism, we decided to test the hypothesis that infectious agent antigens, dietary peptides and haptenic chemicals may bind to DPP IV (CD 26) and CD69, resulting in autoantibody production and modulation and expression of immune and inflammatory reaction in autism.

Material and Methods

Patients

Blood samples from fifty subjects (33 males and 17 females), 3-14 years of age (mean 7.2 years), with a diagnosis of autism, were sent by different clinicians to our laboratory for immunological examination. Clinical diagnosis of autism was made according to the DSM-III-R criteria, established by the American Psychiatric Association (Was., DC) as well as by a developmental pediatrician, a pediatric neurologist, and/or a licensed psychologist. Samples were excluded if their medical histories included head injury, evidence of gliomas, failure to thrive, and other conditions that may contribute to abnormal development.

For comparison, serum samples from 50 healthy matched controls with negative anti-nuclear antibody titers and no known autoimmune diseases were include. The test requests were properly documented and kept in a confidential file. All persons gave their informed consent and allowed including of their data in this manuscript without disclosure of their identity in the publication.

Patient, Proteins and Reagents

Gliadin peptides QQLPQPQQPQQSFPQQQPF, (SEQ ID NO:125), LQLQPFPQPQLPYPQPQLPY (SEQ ID NO:126) —P Q P L P Y P Q P Q P F, (SEQ ID NO:127), QQPQQFZPQQPYPZXZPZLGZZZPFPPZ, (SEQ ID NO:128), gluteomorphin ZGZPGYYPTSPZZPGQEQ, (SEQ ID NO:129), casomorphin ZTZSLVYPFPGPIPNSLP (SEQ ID NO:130), B-casein LHLPLPLLZSWMHZPHZPL (SEQ ID NO:131), and CD69 antibody binding epitope MECEKNLYWICNKPYK (SEQ ID NO:132) were synthesized by Bio-Synthesis Inc. (Lewisville, Tex.). Dipeptidylpeptidase IV (CD26), streptokinase (SK), lipopolysaccharide (LPS), human serum albumin (HSA), mercury [o-carboxyphenyl) Thio] ethyl mercury sodium salt (Thimerosal) were purchased from Sigma (St. Louis, Mo.).

Binding of Thimerosal to Human Serum Albumin

For this preparation, 100 mg of human serum albumin (HSA) was dissolved in 9 ml of buffer solution containing potassium chloride and sodium borate 0.05 ml/liter and pH was adjusted to 9.4 with 0.1 N NaOH. Then 25 mg of Thimerosal or sodium merthiolate was dissolved in one ml of $H_2O$ and added dropwise to the HSA solution while stirring over a period of one hour. The reaction mixture was stirred overnight, dialyzed against 0.1 M PBS using tubing with a cutoff of 8000 Dalton. Conjugation of ethyl mercury to HSA was confirmed by SDS gel electrophoresis (shift in the HSA band). In addition spectrograph analysis of conjugate was undertaken. There was a marked increase in absorption from 230 to 260 nm, which indicated that ethyl mercury became covalently linked to the protein carrier (HSA).

Antibodies

Antibodies to CD26 and CD69 were prepared in rabbits according to standard protocols by Biosynthesis (Lewisville, Tex.). These polyclonal antibodies were purified by affinity chromatography on protein A-sepharose first and then labeled with horseradish peroxidase.

ELISA Procedure

Enzyme-linked immunosorbent assay (ELISA) was used according to the above procedures.

Results

Anti-CD26 and CD69

Figure 13:
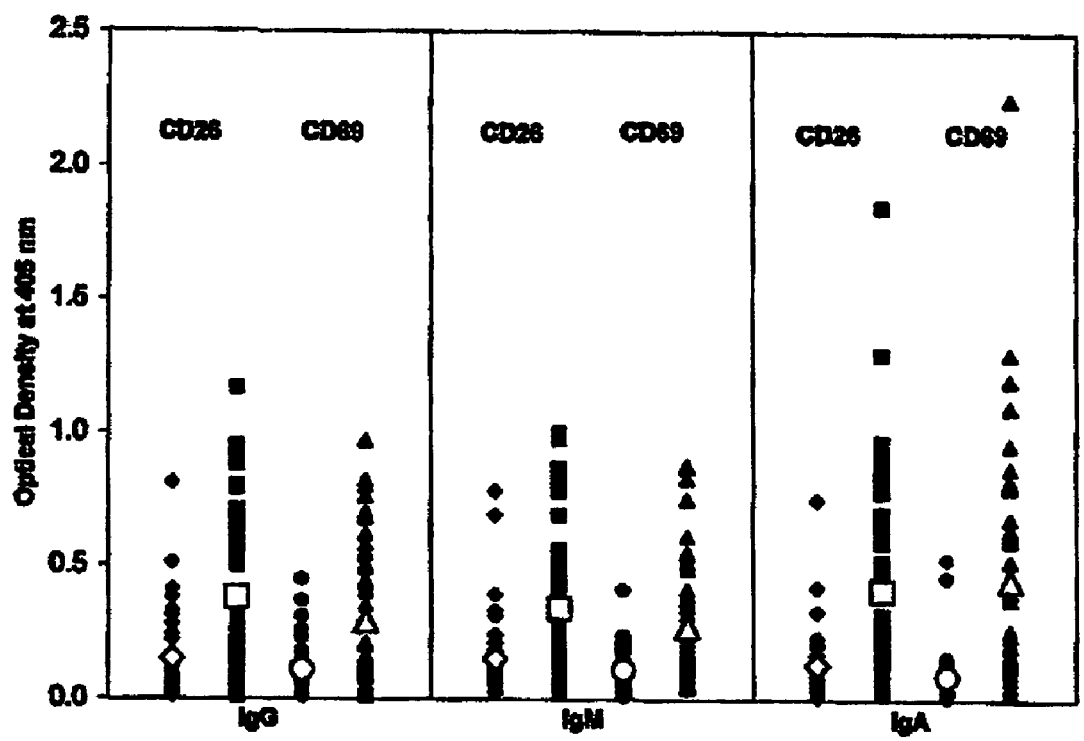
FIG. 13 shows a scattergram of serum titer of IgG, IgM, and IgA antibodies against Dipeptidyl peptidase IV (CD26) in healthy controls subjects ♦ and autistic patients ■ and CD69 in healthy control subjects ● and autistic patients ▲ expressed as optical density in ELISA test.

We investigated whether autoantibodies to CD26 exist in the sera of patients with autism by ELISA using highly purified CD26. As shown in FIG. 13, at a cutoff of 0.3 O.D. or 2 S.D. above the mean and sera dilution of 1:100, IgG, IgM and IgA isotype anti-CD26 autoantibodies were detected in 24 of 50 (48%) for IgG, 20 of 50 (40%) for IgM. and 22 of 50 (44%) for IgA in patient serum samples. In contrast, autoantibodies to CD26 were detected in 14%, 10% and 8% of healthy donors. The mean±S.D. for these antibodies in controls ranged from 0.13±0.13 to 0.15±0.14 and in patients, significantly elevated and ranged from o.34±0.27 to 0.41±0.39 with p-value being highly significant (p<0.0001). Each serum sample was also tested for the pressure of anti-CD69 autoantibodies by using the specific CD69 epitope. Analysis of anti-CD69 IgG, IgM and IgA levels in controls and patients with autism showed significant differences between antibody values and % elevation of these antibodies against CD69 (FIG. 13). The mean±S.D. of O.D. values in controls ranged from 0.09±0.09 to 0.11±0.09 and for patients, from 0.27±0.21 to 0.45±44 (p<0.0001). Similar to antibodies against CD26, these values for CD69 were the highest for IgA, and then for IgG or IgM levels.

Eight of 50 (16%) or 7 of 50 (14%) of patients showed simultaneous elevation in IgG, IgM and IgA antibodies against CD26 and CD69. This simultaneous elevation of antibodies was not detected in sera of any of the healthy controls (FIG. 13).

Antibodies Against Gluten and Casein Peptides

Figure 14:
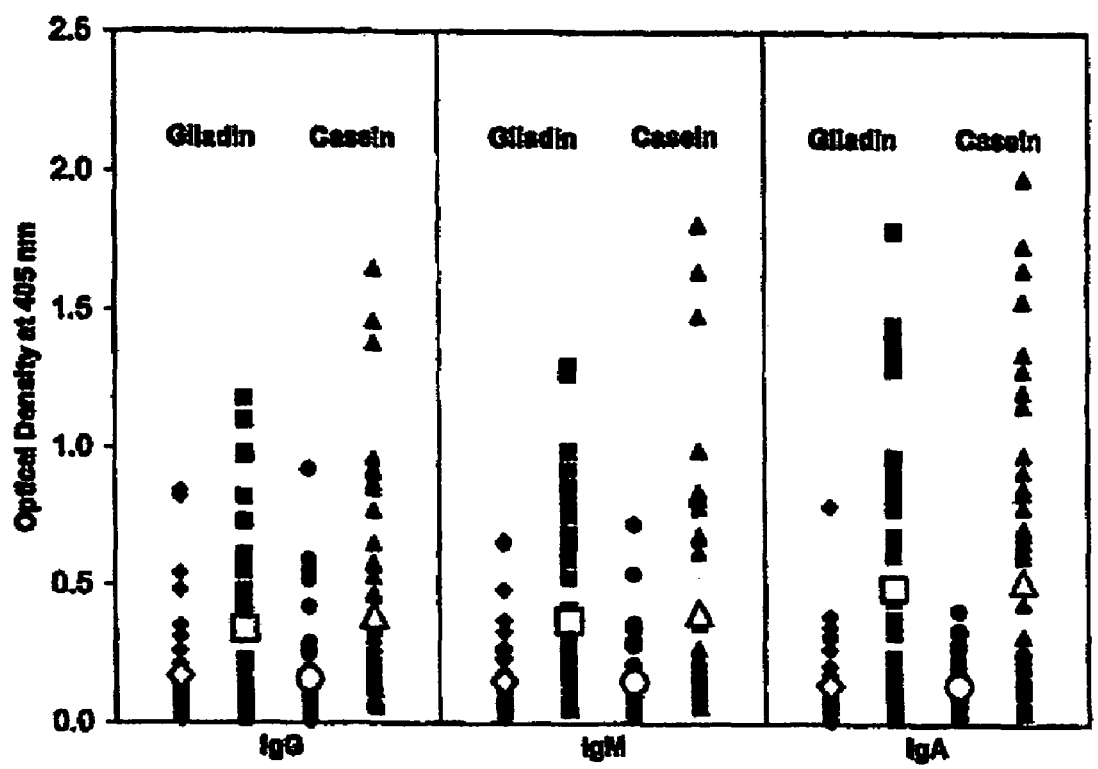
FIG. 14 shows a scattergram of serum titer of IgG, IgM, and IgA antibodies against gliadin peptides in healthy controls subjects ♦ and autistic patients ■ and CD69 in healthy control subjects ● and autistic patients ▲ expressed as optical density in ELISA test.

Having shown that a subpopulation of children with autism exhibited antibodies against CD26 and CD69, we then set out to show that these antibodies are generated in response to dietary peptides, infectious agent antigens (SK) and ethyl mercury. Using similar ELISA methods, the results of IgG, IgM and IgA antibodies against gluten peptides are shown in FIG. 14. The O.D. for IgG antibody values with 1:100 dilutions of healthy control sera ranged from 0.01-0.84, varying among subjects. The mean±S.D. value were 0.17⌐0.17. The corresponding IgG O.D. values from autistic children's sera ranged from 0.03-1.18 with a mean±S.D. of 0.34±0.29. At a cutoff value of 0.3 O.D., levels of IgG antibody against gliadin peptides were calculated and found that while six of 50 (12%) of controls had high IgG values, patients showed IgG elevation in 22 or 44% (p<0.0001). Levels of IgM and IgA anti-gliadin peptides in controls and children with autism are also shown in FIG. 14. Similar to IgG, at 2 S.D. above the mean, these antibodies were significantly higher in patients, 36% for IgM and 46% for IgA, while in controls, 10% were elevated for IgM and 12% for IgA (p<0.0001).

In conjunction with the increase of IgG, IgM and IgA antibodies against gliadin peptides, we observed a statistically significant increase of anti-casein peptide antibodies in patients' sera. The mean±S.D. of antibodies against casein peptide for controls was 0.16±0.17 for IgG, 0.16±0.13 for IgM and 0.14±0.09 for IgA antibodies.

The corresponding values in patients with autism were 0.39±0.38 for IgG, 0.40±0.41 for IgM, and the highest value, 0.52±0.52 for IgA antibodies (FIG. 14). Percent elevation of IgG, IgM and IgA antibodies in controls were 10%, 8% and 8%, while 42%, 34% and 42% of patients' sera at the cutoff of 0.3 O.D. showed IgG, IgM or IgA antibodies against casein peptides.

Anti-Streptokinase (SK) Antibody Levels

Figure 15:
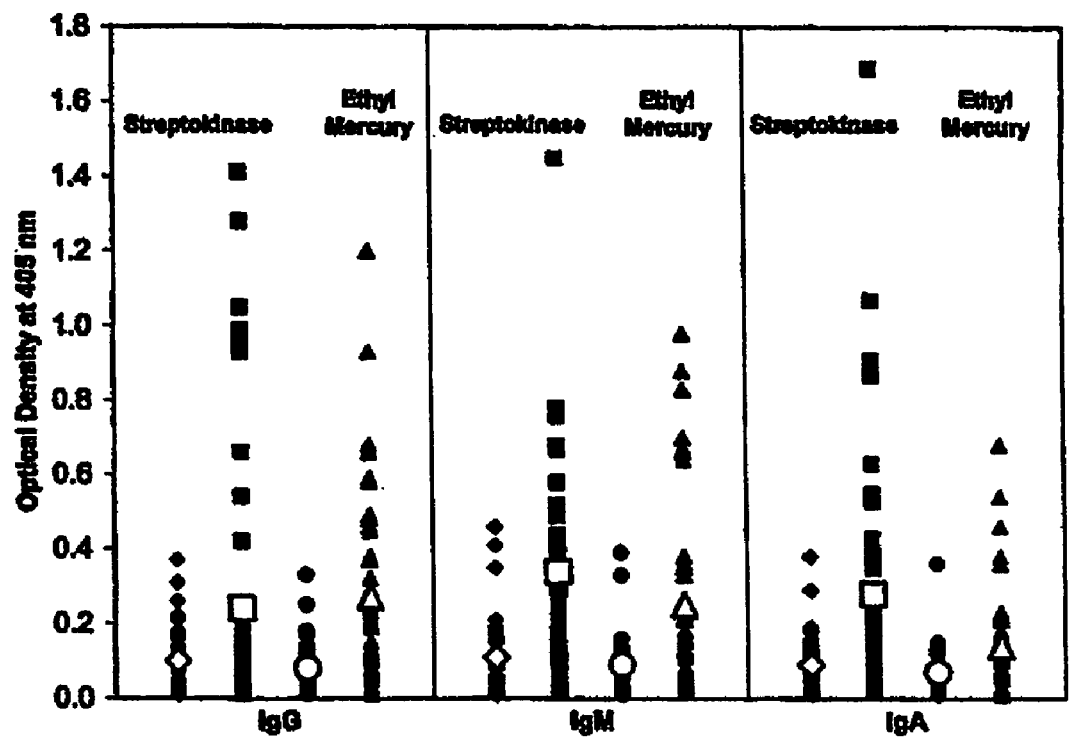
FIG. 15 shows a scattergram of serum titer of IgG, IgM, and IgA antibodies against streptokinase in healthy controls subjects ♦ and autistic patients ■ and CD69 in healthy control subjects ● and autistic patients ▲ expressed as optical density in ELISA test.

Analysis of anti-SK IgG, IgM and IgA levels (FIG. 15) shows that while only one or two out of 50 control specimens (2-4%) had elevated antibodies, a significant percent of patients (18%, 48% and 24%) demonstrated IgG, IgM or IgA elevation. The mean±S.D. of anti-SK antibodies was significantly elevated in patients over controls with IgA and IgM (p<0.0001) and for IgG (p<0.008) (FIG. 15).

Anti-Ethyl Mercury Antibody Level

Similar to the above determination at a cutoff of 0.30 O.D., levels of IgG, IgM and IgA antibodies against ethyl mercury were calculated in controls and patients' sera and found that while one or two out of 50 (2%-4%) of controls had high IgG values, the patients' group showed IgG elevation in 28% and IgM elevation in 30%. In regards to IgA elevation against mercury, none of the controls and only 5 of 50 patients (10%) had increased antibody levels (FIG. 15). Comparison of these antibody values in controls and patients resulted in p values <0.0001 for IgG and IgM but <0.004 for IgA. For this measurement, since ethyl mercury was conjugated to HSA, the O.D. of corresponding wells coated with HSA along were subtracted from the O.D.s of ethyl mercury bound to HSA-coated wells.

To our knowledge, our analyses are the first to clearly demonstrate that dietary peptides, bacterial toxins and xenobiotics bind to lymphocyte receptors and/or tissue enzymes. This results in autoimmune reactions in children with autism. We suggest that these findings provide a mechanism by which environmental factors modulate the immune system and should help us develop preventive and therapeutic methods to reduce dietary peptides, bacterial toxins and toxic chemical-induced autoimmune reaction in autism.

Example 3

Heat Shock Protein and Gliadin Peptide Promote Development of Peptidase Antibodies in Children with Autism and Patients with Autoimmune Disease We assessed a hypothesis in a group of healthy control subjects compared to patients with autism and patients with mixed connective tissue disease. Our data suggests a potential role for HSP-60 and dietary peptides in this process.

Materials and Methods

Patients

Blood samples from fifty subjects (33 males and 17 females), 3-14 years of age (mean 7.2 years), with a diagnosis of autism, were sent by different clinicians to our laboratory for immunological examination. The clinical diagnosis of autism was made according to the DSM-III-R criteria, established by the American Psychiatric Association (Wash., DC), as well as by a developmental pediatrician, a pediatric neurologist, and/or a licensed psychologist. Samples were excluded if their medical histories included head injury, evidence of gliomas, failure to thrive, and other known factors that may contribute to abnormal development. Blood samples from 50 patients with confirmed diagnosis of mixed connective tissue disease (31 females and 19 males), 36-75 years of age with anti-nuclear antibody (ANA) titer of 640 or greater Sm/RnP speckled pattern chromosome negative were selected from our collection sera preserved at −70° C. For comparison serum samples from 50 healthy (25 children age 3-14, 25 adults age 36-75) controls with negative ANA titers and no known autoimmune diseases were included. The test requests were properly documented and kept in a confidential file. All persons gave their informed consent and allowed inclusion of their data without disclosure of their identity in the publication.

Peptides

Gliadin peptides: Gliadin peptide QQLPQPQQPQQSF-PQQQPF (SEQ ID NO:125) and *Chlamydia trachomatis* HSP-60 peptide LKQIAAHAGKEGAIIFQQVM, HPLC grade, were (SEQ ID NO:133) synthesized by Bio-Synthesis Inc. (Lewisville, Tex.).

Proteins: DPP IV (CD 26), Aminopeptidase I, Aminopeptidase N (CD13), Streptokinase (SK), Lipopolysaccharide (LPS), Human Serum Albumin (HSA) were purchased from Sigma (St Louis, Mo.).

Antibodies: Antibodies to DPP IV, DPP I, aminopeptidase N, streptokinase, HSP-60, and gliadin peptides were prepared in rabbits according to standard protocols (24) by Cocalico Biologicals, Inc. (Reamstown, Pa.). These polyclonal antibodies were purified by affinity chromatography on protein A-sepharose (115).

Enzyme-Linked Immunosorbent Assay (ELISA)

Enzyme-linked immunosorbent assay (ELISA) was used according to the above procedures.

Results

Figure 16:
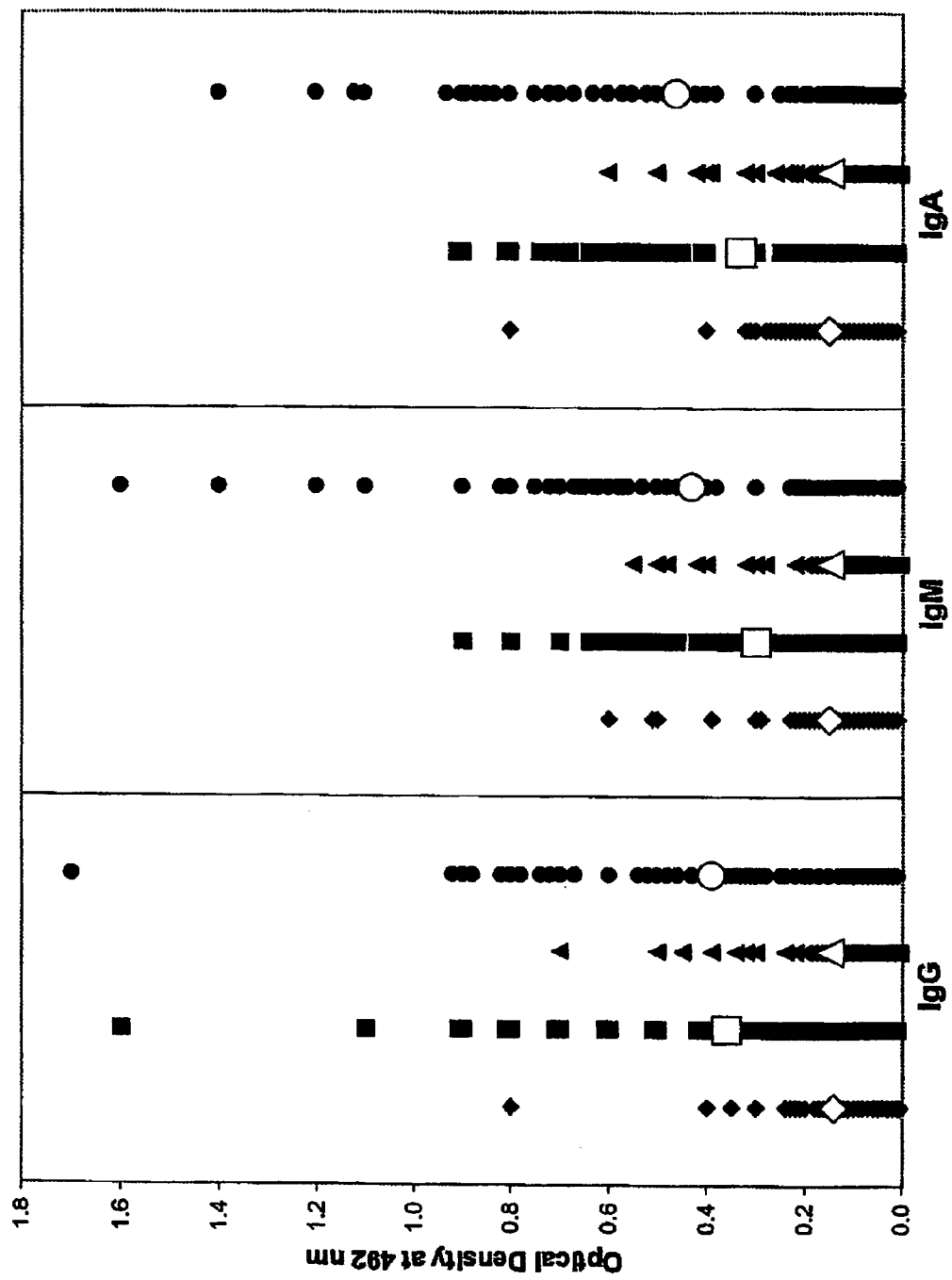
FIG. 16 shows a scattergram of serum titer of IgG, IgM, and IgA antibodies against dipeptidylpeptidase IV (DPP IV) in healthy, young control subjects ♦, autistic patients ■, in healthy, older control subjects ▲, and patients with autoimmune disease expressed as optical density in ELISA test.
Figure 17:
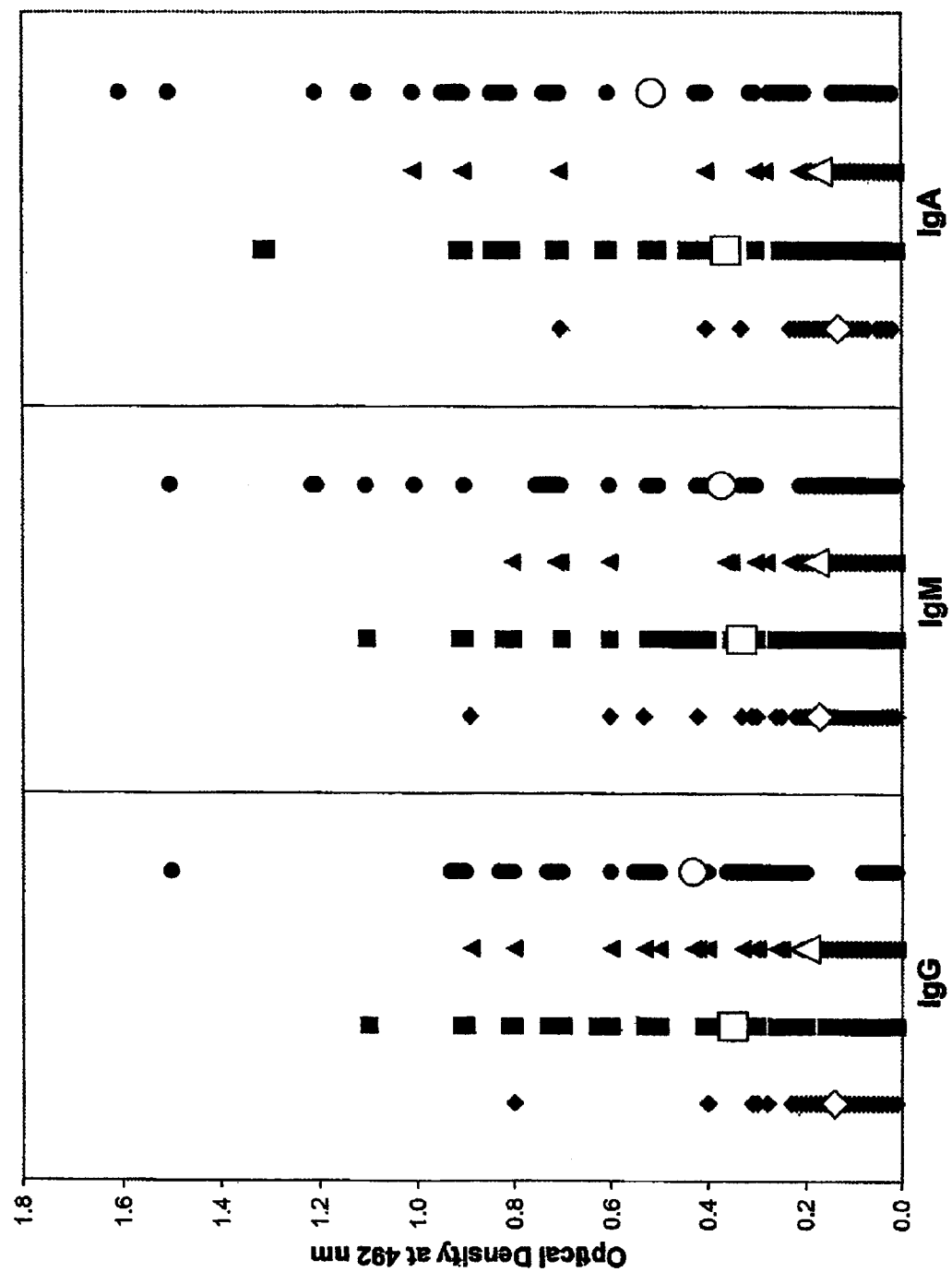
FIG. 17 shows a scattergram of serum titer of IgG, IgM, and IgA antibodies against DPPI in healthy, young control subjects ♦, autistic patients ■, in healthy, older control subjects ▲ and patients with autoimmune disease expressed as optical density in ELISA test.
Figure 18:
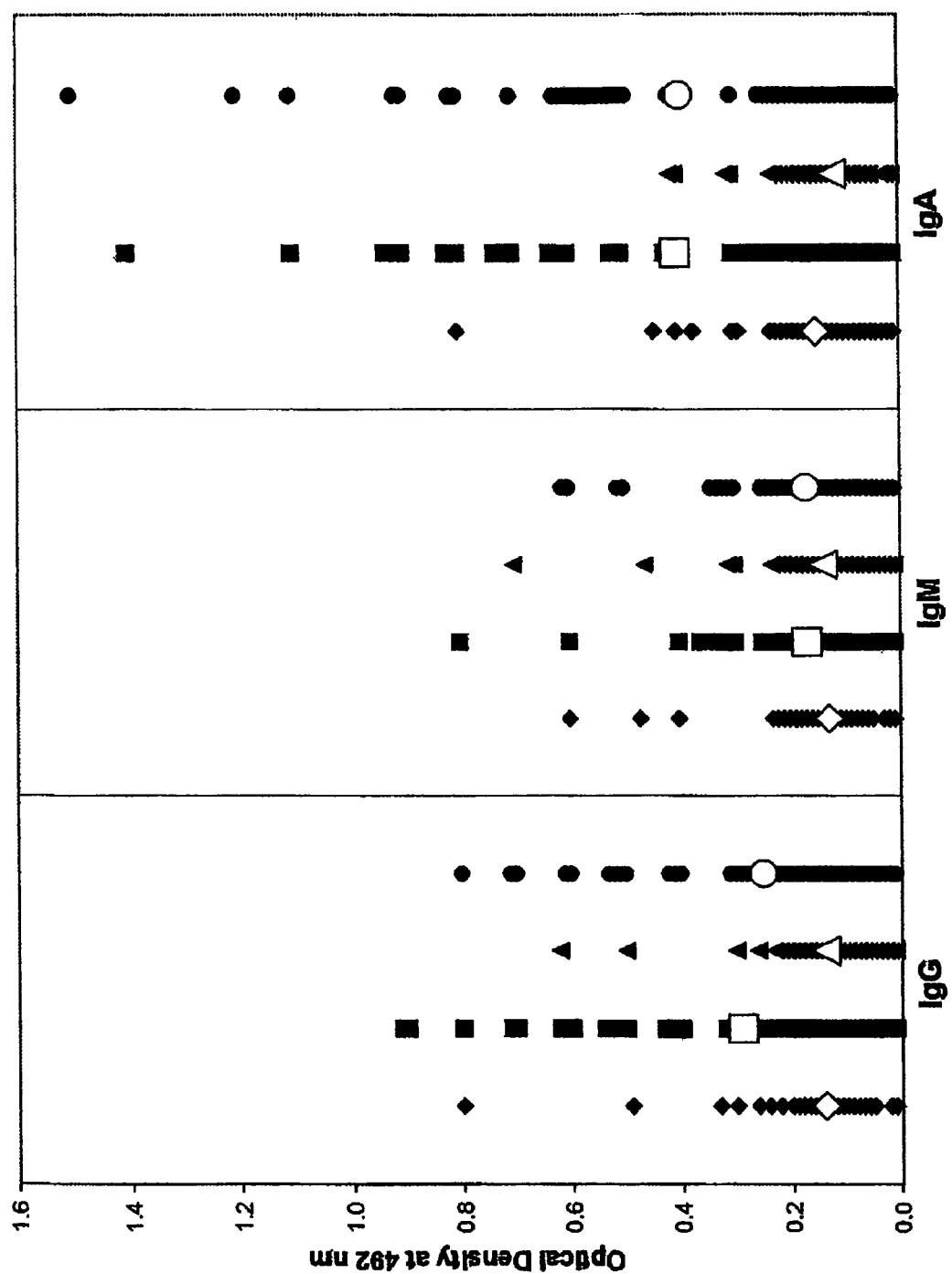
FIG. 18 shows a scattergram of serum titer of IgG, IgM, and IgA antibodies against CD13 in healthy, young control subjects ♦, autistic patients ■, in healthy, older control subjects ▲ and patients with autoimmune disease ● expressed as optical density in ELISA test.

Anti-DPP IV Autoantibodies Levels in Control Children with Autism and Patients with Autoimmune Disease Using ELISA assays, sera from 50 healthy subjects, 50 autistic children and 50 patients with mixed connective tissue disease were analyzed for the presence of IgG, IgM and IgA antibodies against DPP IV. Results expressed as O.D. with mean±standard deviation (S.D.) are summarized in FIG. 18. The O.D. for IgG antibody values obtained with 1:200 dilution of healthy control sera ranged from 0.05-0.8, varying among subjects. The mean±S.D. of these O.D. values ranged from 0.15±0.14. The corresponding IgG O.D. values from autistic children and patients with autoimmune disease sera ranged from 0.01-1.1 and 0.01-1.5 with mean±S.D. of IgG values which ranged from 0.35±0.28 and 0.43±0.30. The result of post hoc multivariate comparison tests reported in Table 4 show that while the control groups are statistically alike for IgG, IgM and IgA in anti-DPP IV, both the autism and autoimmune groups were significantly different when compared to the control groups (p<0.001). At a cutoff value of 0.29 O.D. levels of IgG antibody were calculated in controls and patients' sera and found that while 5 out of 50 (10%) of children controls and 7 out of 50 (14%) of adult controls had high IgG values, the patients' group showed IgG elevation in 54% (autistic children) and 64% (patients with autoimmune disease) (P<0.0001) (Table 3). Levels of IgM anti-DPP IV in healthy controls and patients with autism and autoimmune disease are also shown in FIG. 16. These serum IgM antibodies were significantly higher in patients than in controls. The mean±S.D. for controls ranged from 0.14±0.12 and for patients from 0.33±0.26 to 0.37±0.36 (P<0.0001) (FIG. 15). When the 0.29 O.D. cut-off point was used, 8% of controls versus 50% and 46% of patients' sera showed elevated IgM antibody levels (P<0.0001) (Table 3). Likewise, IgA antibody levels against DPP IV were examined in three groups. Individual and mean±S.D. data depicted in FIG. 16 showed significant differences between control and patients group. The mean±S.D. for IgA antibody levels in controls was 0.14±0.11 and in patients from 0.36±0.33 to 0.51±0.40 (P<0.0001). Percent elevated serum IgA Anti-DPP IV antibodies at O. D. value of greater than 0.29 were significantly higher in patients with autism (44%) and autoimmune disease (58%) than in controls (4-6%). (Table 3) Anti-DPP I antibody levels in controls, children with autism and patients with autoimmune disease Analysis of anti-DPP I IgG, IgM, and IgA levels in controls and patients with autism or autoimmune disease showed significant differences between the antibody values and % elevation of these antibodies against DPP I (FIG. 17). The mean±S.D. of O.D. values in controls were 0.14±0.11 to 0.16±0.15 and, for patients, from 0.30±0.22 to 0.46±0.36 (P<0.0001) (FIG. 17).

Figure 20:
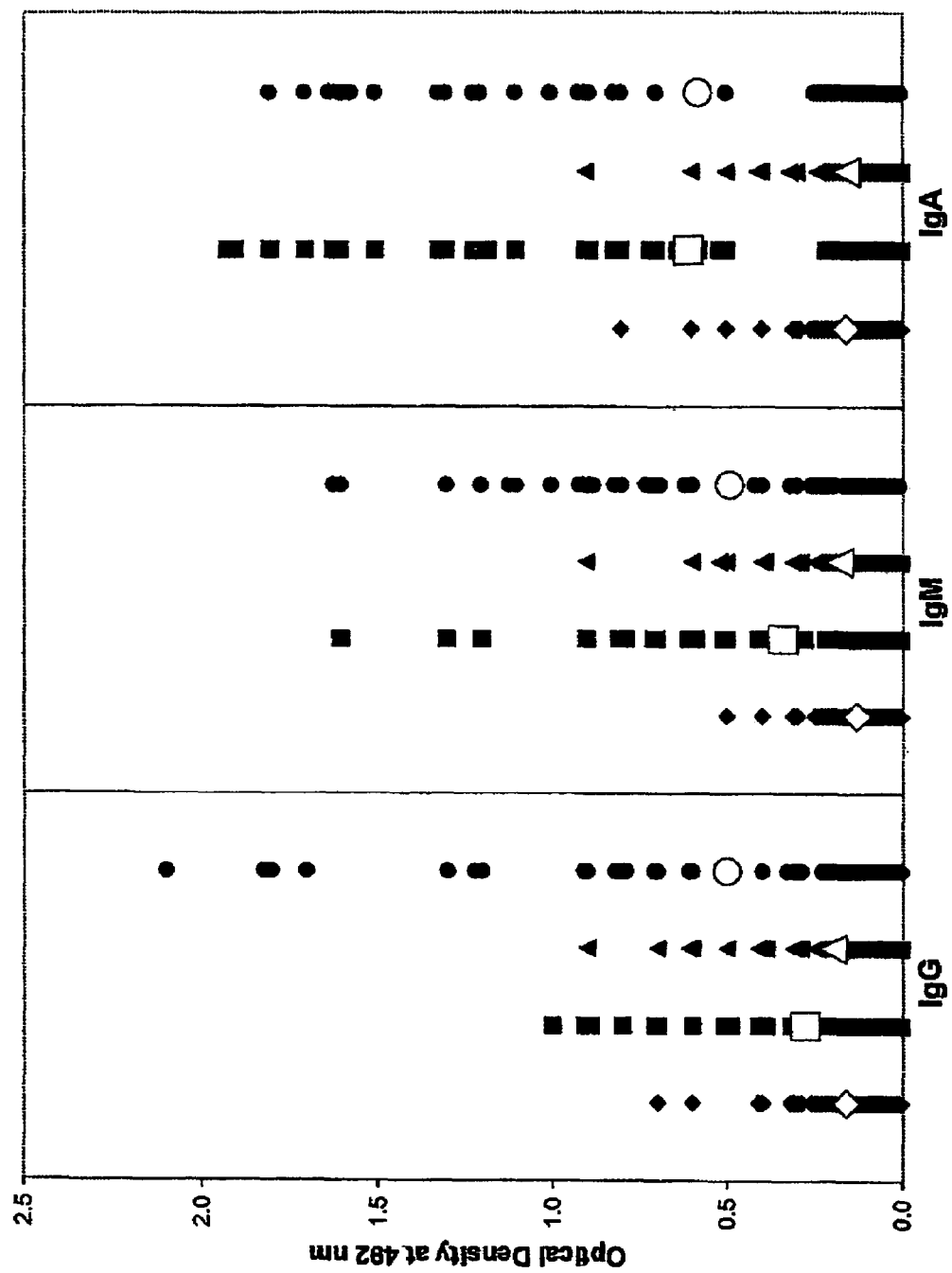
FIG. 20 shows a scattergram of serum titer of IgG, IgM, and IgA antibodies against HSP 60 in healthy, young control subjects ♦, autistic patients ■, in healthy, older control subjects ▲ and patients with autoimmune disease ● expressed as optical density in ELISA test.

Anti-Aminopeptidase-N (CD13) Autoantibodies Levels in Controls, Children with Autism and Patients with Autoimmune Disease Similar to the analysis of DPP IV and DPP I data, levels of IgG, IgM and IgA antibodies against CD13 were significantly higher in patients than in controls (FIG. 20). In comparison to DPP IV and DPP I percent elevation of CD13 autoantibodies in patients were significantly lower for IgM (P<0.31) but not for IgG and IgA antibody levels (P<0.0001) (Table 3).

Table 4 reports that for IgG and IgA, similar to control groups, autoimmune and autism are alike. Yet a significant difference is detected between the control groups and the autism and autoimmune groups. According to our data, for IgM anti-CD13 no differences between the four groups are detected.

Figure 19:
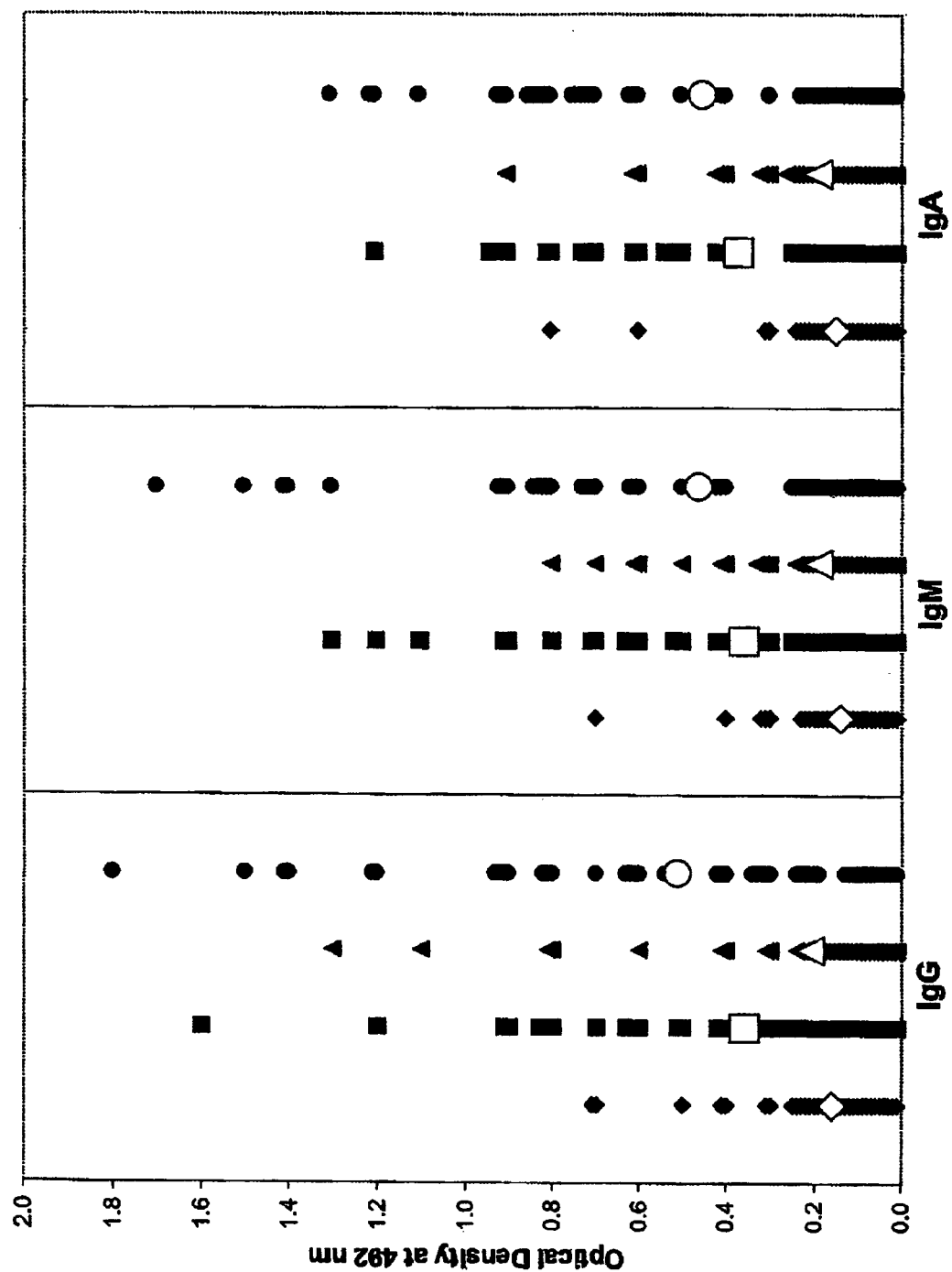
FIG. 19 shows a scattergram of serum titer of IgG, IgM, and IgA antibodies against gliadin peptide in healthy, young control subjects ♦, autistic patients ■, in healthy, older control subjects ▲ and patients with autoimmune disease ● expressed as optical density in ELISA test.
Figure 21:
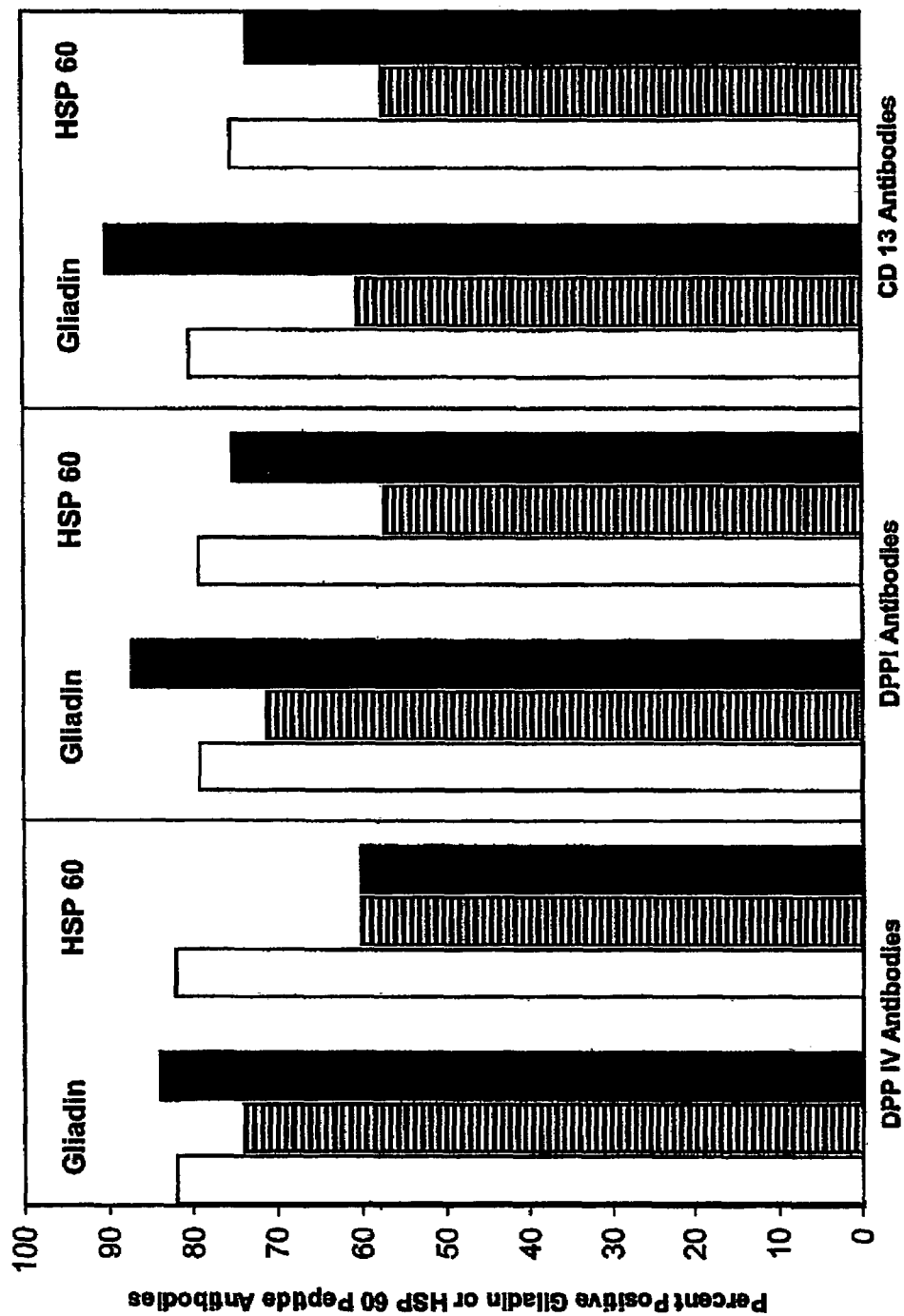
FIG. 21 shows percent positive sera from patients with autism for IgA □, IgG ▤, and IgM ■ antibodies against gliadin and HSP 60 peptides, which are positive for DPP IV, DPP I, or CD13 Antibodies.
Figure 22:
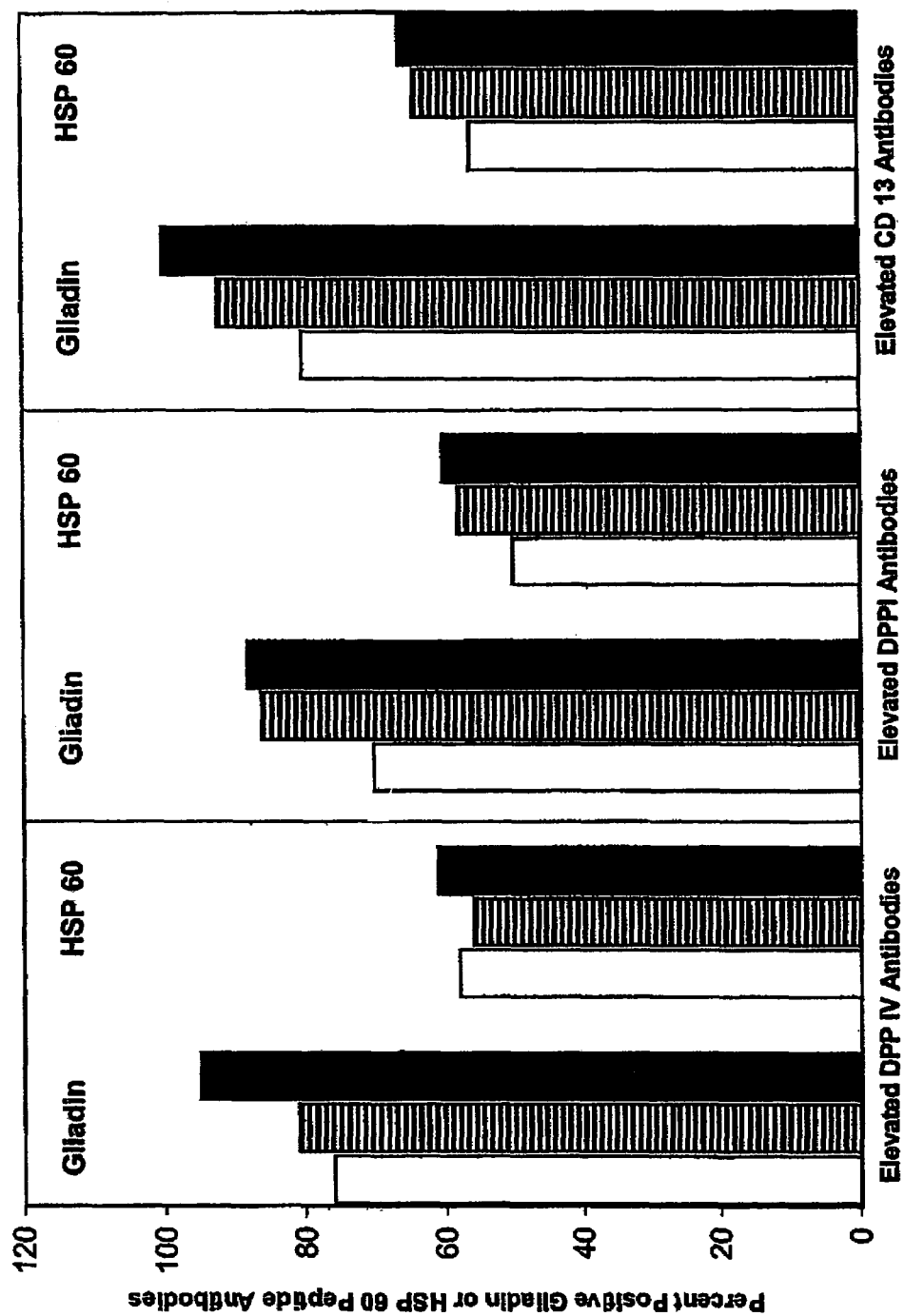
FIG. 22 shows percent positive sera from patients with autoimmune disease for IgA □, IgG ▤, and IgM ■ antibodies against gliadin and HSP 60 Peptides, which are positive for DPP IV, DPP I, or CD13 Antibodies.

Anti-Gliadin and HSP-60 Peptides Autoantibodies Levels in Controls, Children with Autism and Patients with Autoimmune Disease Concomitant with the increase of IgG, IgM and IgA against DPP IV, DPP I and CD13, we observed a statistically significant increase of anti-gliadin and anti-HSP-60 antibodies in most patients' sera. Antibodies for controls ranged from 0.14±0.11–0.15±0.17 and for patients from 0.36±0.32–0.51±0.43 (P<0.0001) (FIG. 19, Table 3). Table 4 reports that IgM and IgA for control groups against Gliadin Peptide are statistically alike. Similarly, autism and autoimmune groups are identical, yet the control groups are different when compared with the autism and autoimmune groups. Finally, Table 4 reports that for IgA against HSP-60 the control groups are statistically not different from the autoimmune and autism groups. But for IgG no similarity between the autoimmune groups and other groups (autism and controls) was detected. The autism and control groups are similar but different from the autoimmune group. For the IgM no differences between the autism group and control-adults were observed, but the autism group was statistically different when compared with control-children. These values as well as % elevation of IgG, IgM, and IgA antibodies against gliadin are presented in Tables 3, 4. For examination of possible involvement of gliadin and HSP-60 peptides in the production of autoantibodies against different peptidases, calculation of simultaneous elevation in these antibodies in patients' sera were made and presented in FIGS. 21, 22. Between 57-90% of sera from children with autism who had high IgG, IgM or IgA against DPP IV, DPP I or CD13 had simultaneous elevation in these antibodies against gliadin or HSP-60 peptides (FIG. 21). This correlation between IgG, IgM and IgA antibodies against DPP IV, DPP I CD13 and gliadin and HSP-60 peptides in sera of patients with autoimmune disease was from 50-100% (FIG. 22). When concomitant detection of antibodies against all five tested antigens (DPP IV, DPP I, CD13, gliadin peptide, HSP-60) was measured, 72, 30 24% of sera from children with autism versus 41, 25 and 26% of sera from patients with autoimmune disease had simultaneous elevation in IgA, IgG, and IgM antibody levels against all tested antigens, respectively.

Many modifications and variations of the embodiments described herein may be made without departing from the scope, as is apparent to those skilled in the art. The specific embodiments described herein are offered by way of example only. References cited herein are incorporated by reference.

REFERENCES

1. Comi A. M Zimmerman A. W., Frye V. H., Law P. A., and Peeden J. N. (1999) Familial clustering of autoimmune disorders and evaluation of medical risk factors in autism. *Journal of Child Neurology,* 14(6):388-94.
2. Chess S., Fernandez P., and Kom S. (1978) Behavioral consequences of congenital rubella. *Journal of Pediatrics,* 93:669-703.
3. Desmond M. M., Wilson G. S, Melnick J. L., Singer D. B., Zion T. E., Rudolph A. J., Pineda R. G., Ziai M. H., and Blattney R. J. (1967) Congenital rubella encephalitis. *Journal of Pediatrics,* 71:311-331.
4. Ahlfors K., Ivarsson S. A., Harris S., Svanberg L., Holmqvist R., Lernmakr B., and Theander G. (1984) Congenital cytomegalovirus infection and disease in Sweden and the relative importance of primary and secondary maternal infections. *Scandinavian Journal of Infectious Diseases,* 16:129-137.
5. Edelson S. B. and Cantor D. S. (1998) Autism: xenobiotic influences. Toxicol. *Ind. Health,* 14:799-811.
6. Goldman L. R. and Koduru S. (2000) Chemicals in the environment and developmental toxicity to children: a public health and policy perspective. *Environmental Health Perspectives,* 108 Suppl 3:443-448.
7. Myers G J and Davidson P. W. (1998) Prenatal methylmercury exposure and children: neurological, developmental, and behavioral research. *Environmental Health Perspectives,* 106 Suppl 3:841-847.
8. Rodier P. M., Ingram J. L., Tisdale B., and Croog V. J. (1997) Linking etiologies in humans and animal models: studies of autism. *Reproductive Toxicology,* 11(2-3):417-422.
9. American Psychiatric Association, *DSM IV,* 2000.
10. Kiberstis P. and Roberts L. (2002) It's not just the genes. *Science* 296:685-686.
11. Vojdani A., Campbell A. W., Anyanwu E., Kashanian A., Bock K., and Vojdani E. (2002) Antibodies to neuron-specific antigens in children with autism: possible cross-reaction with encephalitogenic proteins from milk, *Chlamydia pneumoniae* and *Streptococcus* group A. *J. Neuroimmunol.* 129:168-177.
12. Vojdani A., Pangbom J. B., Vojdani E., and Cooper E. L. Infections, toxic chemicals and dietary peptides binding to lymphocyte receptors arid tissue enzymes are responsible for autoimmunity in autism. *Int. J. Immunopath. Pharmacol.,* vol. 16, no. 3, 189-199 (2003)
13. Vojdani A., Vojdani E. and Cooper E. (2003) Antibodies to myelin basic protein, myelin oligodendrocytes peptides, a-(3-crystallin, lymphocyte activation, and cytokine production in patients with multiple sclerosis. *Journal of Internal Medicine,* 254:1-12.
14. Vojdani A. and Cooper E. L. (in press) Antibodies against CNS antigens in autism: possible cross-reaction with dietary proteins and infectious agent antigens. *Neurophychiatric Disorders.*
15. Vojdani A. and Cooper E. L. (in press) Identification of diseases that may be targets for complementary and alternative medicine. *Pioneers in Biomedicine.*
16. Ivarsson S. A., Bjerre L., Vegfors P., and Ahlfors K. (1990) Autism as one of several abnormalities in two children with congenital cytomegalovirus infection. *Neuropediatrics* 21:102-103.
17. Zimmer C. (2001) Do chronic diseases have an infectious root? *Science* 293:1974-1977.
18. Taylor B., Miller E., Farrington C. P., Petropoulos M. C., Favot-Mayaud I., Li J., and Waight P. A. (1999) Autism and measles, mumps, rubella vaccine: no epidemiological evidence for a causal association. *Lancet,* 353 (9169): 2026-2029.
19. Fatemi S. H., Earle J., Kamodia R., Kist D., Emamian E. S., Patterson, P. H., Shi L., Sidewell R. (2002) Prenatal viral infection leads to pyramidal cell atrophy and macrocephaly in adulthood: implications for genesis of autism and schizophrenia. *Cell. Mol. Neurobiol.* 22:25-33.
20. Shi L., Fatemi S. H., Sidwell R. W., and Patterson P. H. (2003) Maternal influenza infection causes marked behavorial and pharmacological changes in the offspring. *J. Neurosciences,* 23:297.
21. Fujunami R. S. and Oldstone M. B. A. (1985) Amino Acid homology between the encephalitogenic site of myelin basic protein and virus: mechanism for autoimmunity. *Science,* 203:1043-1045.
22. Rajeswari M. H., Ravindranath H., and Graves M. C. (1992) Monoclonal IgM antibodies from CMV-infected mice recognize the GICNAC-containing receptor determinant of murine CMV as well as neutralizing anti-CMV IgG antibodies. *Virology,* 1.88:143-151.
23. Wucherpfenning K. W. and Strominger J. L. (1995) Molecular mimicry in T cell-mediated autoimmunity: viral peptides activate human T cell clones specific for myelin basic protein. *Cell,* 80:695-705.
24. Moktarian F., Zhang Z., Shi Y., Gonzales E. and Sobel R. A. (1999) Molecular mimicry between a viral peptide and a myelin oligodendrocyte glycoprotein induces autoimmune demyelinating disease in mice. *J. Neuroimmunol.,* 95:43-8.
25. Esposito M., Venkatesh V., Otvos L., Weng Z., Vajda S., Banki K., and Per] A. (1999) Human transaldolase and cross-reactive viral epitopes identified by autoantibodies of multiple sclerosis patients. *J. Immunology,* 163:4027-32.
26. Caselli E., Boni M., Bracci A., Rotola A., Cermelli C., Castellazi M., Di Luca D., and Cassai E. (2002) Detection of antibodies directed against human herpesvirus-6 U 94/REP in sera of patients affected by multiple sclerosis. *J. Clin. Microbiol.,* 40:4131-4137.
27. Wucherpfenning K. W. (2002) Infectious trigger for inflammatory neurological disease. *Nature Medicine,* 8:455-457.
28. Olson J. K., Eagar T. N., and Miller S. D. (2002) Functional activation of myelin-specific T-cells by virus-induced mimicry. *J. Immunol.,* 169:2719-2726.
29. Bronze M. S. and Dale J. B. (1993) Epitope of streptococcal M proteins that evoke antibodies that cross-react with the human brain. *J. Immunol.,* 151:2820-2828.
30. Lenz D. C., Lu L., Conant S. B., Wolf N. A., Gerard H. C., Whittum-Hudson J. A., Hudson A. P., and Swanborg R. H. (2001) A *Chlamydia pneumoniae*-specific peptide induces experimental autoimmune encephalomyelitis in rats. *J. Immunol.,* 167, 1803-1808.
31. Bariety J., Druet P., Laliberte F., and Sapin C. (1971) Glomerulonephritis with y- and 1Cglobulin deposits induced in rats by mercuric chloride. *Am. J. Pathol.,* 65:293-297.
32. Roman-Franco A. A., Turiello M., Albini B., Ossi E., Milgrom F., and Andres G. A. (1978) Anti-basement membrane antibodies and antigen-antibody complexes in rabbits injected with mercuric chloride. *Clin. Immunol. Immunopathol.,* 9:464-470.
33. Hirsch, F. Couderc J., Sapin C., Fournie G., and Druet P. (1982) Polyclonal effect of $HgCL_2$ in the rat, its possible role in an experimental autoimmune disease. *Eur. J Immunol.,* 12: 620-626.
34. Robinson C. J., Abraham A. A., and Balazs T. (1984) Induction of anti-nuclear antibodies by mercuric chloride in mice. *Clin. Exp. Immunol.,* 58:300-307.
35. Leung P. S. C. et al., (2003) Immunization with a xenobiotic 6-bromohexanonate bovine serum albumin conjugate induces antimitochondrial antibodies. *J. of Immunolog.* 170:53265332.
36. Edelson S. B. and Cantor D. S. (2000) The neurotoxic etiology of the autistic spectrum disorder: a replicative study. *Toxic. Ind. Health,* 16:239-247.
37. Griem P., Wulferink M., Sachs, Gonzalez J. B., and Gleichmann E., 1998, Allergic and autoimmune reactions to xenobiotics: how do they arise? *Immunology Today,* 19:133-142.
38. Ware J. A., Graf M. L. M., Bartin B. M., Lustberg L. R., and Pohl L. R., 1998, Immunochemical detection and identification of protein adducts of diclofenac in the small intestine of rats: possible role in allergic reactions. *Chem. Res. Toxicol.* 11:164-171.
39. Pohl L. R., Satoh H., Christ D. D., and Kenna J. G., 1988, The immunological and metabolic basis of drug hypersensitivities. *Annu. Rev. Pharmacol. Toxicol.* 28:367-387.
40. Lewis M., Worobey J., Ramsay D. S., and McCormach M. K (1992) Prenatal exposure to heavy metals: effect on childhood cognitive skills and health status. *Pediatrics* 89(6 Pt 1):1010-1015.
41. Goyer R. A. (1996) Results of lead research: prenatal exposure and neurological consequences. *Environmental Health Perspective.* 104(10):1050
42. Myers G. J., Davidson P. W. (1998) Prenatal methylmercury exposure and children:
neurologic, developmental, and behavioral research. *Environmental Health Perspectives.* 106 Suppl 3:841-847.
43. Myers G. J., Davidson P. W. (2000) Does methylmercury have a role in causing developmental problems in children?. *Environmental Health Perspectives.* 108 Suppl 3:413-420.
44. Rimland B. (2000) The, autism epidemic, vaccinations, and mercury. *Journal of Nutritional & Environmental Medicine* 10:261-266.

45. El-Fawal H. A. N., Gong Z., Little A. R., and Evans H. L. (1996) Exposure to mercury results in serum autoantibodies to neurotype and gliotypic proteins. *Neurotoxicology* 17, 267-276.

46. El-Fawal, H. A. N., Waterman S. J., DeFeo A., and Shamy M. Y. (1999) Neuroimmunology: humoral assessment of neurotoxicity and autoimmune mechanism. *Environ. Health Perpect.* 5, 767-775.

47. Qian Y., Harris E. D., Zheng Y., and Tiffany-Castiglioni E. (2000) Lead targets GRP78, a molecular chaperone, in C6 rat glioma cells. *Toxicol. Pharmacol.*, 163, 260-266.

48. Partl S., Herbst H., Schaeper F., Mohnhaupt A., and Stoltenburg-Didinger G. (1998) GFAP gene expression is altered in young rats following developmental low level lead exposure. *Neurotoxicity*, 19, 547-552.

49. Singh V. K., Warren R. P., Odell J. D., Cole P., and Warren L. (1993) Antibodies to myelin basic protein in children with autistic behavior. *Brain Behav. Immun.*, 7, 97-103.

50. Singh V. K., Warren R. P., Averett R., and Ghaziuddin M. (1997) Circulating autoantibodies to neuronal and glial filament protein in autism. *Pediatr. Neurol.*, 17, 88-90.

51. Todd R. D., Hickok J. M., Anderson G. M., Cohen D. J. (1988) Antibrain antibodies in infantile autism. *Biological Psychiatry* 23:644-647.

52. Connolly A. M., Chez M. G., Pestronk A., Arnold S. T., Mehta S., Deuel R. K. (1999) Serum autoantibodies to brain in Landau-Kleffiler variant, autism, and other neurologic disorders. *Journal of Pediatrics* 134(5):607-613.

53. Rogers T. J. and Peterson P. K. (2003) Opioid G protein-coupled receptors: signals at the crossroads of inflammation. *Trends in Immunol.*, 24, 116-121.

54. O'Banion D., Armstrong B., Cummings R. A., Stange J. (1978) Disruptive behavior: a dietary approach. *Journal of Autism & Childhood Schizophrenia.* 8(3):325-337.

55. Scifo R., Cioni M., Nicolosi A., Batticane N., Tirolo C., Testa N., Quattropani M. C., Morale M. C., Gallo F., Marchetti B. (1996) Opioid-immune interactions in autism: behavioral and immunological assessment during a double-blind treatment with naltrexone. *Annali dell Instituto Superiore di Sanita.* 32(3):351-359.

56. Sher L. (1997) Autistic disorder and the endogenous opioid system. *Medical Hypotheses.* 48(5):413-414.

57. Mercer M. E., Holder M. D. (1997) Food cravings, endogenous opioid peptides, and food intake; a review. *Appetite* 29(3):325-352.

58. Shan L., Molberg O., :Parrot L, Hausch F., Filiz F., Gray G. M., Sollid L. M. and Khosla C. (2002) Structural basis for gluten intolerance in Celiac Sprue. *Science*, 297, 2275-2279.

59. Sollid L. M. (2002) Coeliac disease: dissecting a complex inflammatory disorder. *Nature Reviews Immunology*, 2, 647-655.

60. Sblattero D., Berti L, and Trevisiol C. (2000) Human recombinant tissue transglutaminase ELISA: an innovative diagnostic assay for coeliac disease. *Am. J. Gastroenterol.*, 95, 12531257.

61. Baba H., Daune G. C., Ilyas A., Pestronk., Comblath D. R., Chaudhry V., Griffin J. W., and Quarles R. H. (1989) Anti-GM1 ganglioside antibodies with differing fine specificities in patients with multifocal motor neuropathy. *J. Neuroimmunol.*, 25, 143-150.

62. Bajramovic J. J., Plomp A. C., Van Der Goes A., Koevoetes C., Newcombe J., Cuzner M. L., and Van Noort J. M. (2000) Presentation of a-(3-crystallin to T-cells in active multiple sclerosis lesions: an early event following inflammatory demyelination. *J. Immunology*, 164, 4359-66.

63. Brock H. P. M., Uccelli A., Kerlero de Rosbo N., et al. (2000) Myelin/oligodendrocyte glycoprotein-induced autoimmune encephalomyelitis in common marmosets: the encephalitogenic T-cell epitope P-MOG 24-36 is present by a monomorphic MHC class II molecule. *J. Immunology*, 165, 1093-1101.

64. Raine C. S. B., Cannella S. L., and Hauser C. P. (1999) Genain Demyelination in primate autoimmune encephalomyelitis and acute multiple sclerosis lesions: a case for antigenspecific antibody mediation. *Ann. Neurol.*, 46, 144-60.

65. Stefferl A., Schubart A., Storch M., Amini A., Mather L, Lassman H., and Linington C. (2000) Butyrophilin, a milk protein, modulates the encephalitogenic T-cell response to myelin oligodendrocyte glycoprotein in experimental autoimmune encephalomyelitis. *J. Immunol.*, 165, 2859-2865.

66. Hadjivassiliou M., Grunewald R. A., Lawden M., Davies-Jones G. A. B., Powell T., and Smith C. M. (2001) Headache and CNS white matter abnormalities related with gluten sensitivity. *Neurology*, 56, 385-388.

67. Hadjivassiliou M., Boscolos S., and Davies-Jones G. A. B., Grunwald R. A., Not T., Sanders D. S., Simpson J. E., Tongiorgi E., Williamson C. A., and Woodroofe, N. M. (2002) The humoral response in the pathogenesis of gluten ataxia. *Neurology*, 58, 1221-26.

68. Dropcho E. J., Chen Y., Posner, J. B. and Old L. J. (1987) Cloning of a brain protein identified by autoantibodies from a patient with paraneoplastic cerebellar degeneration. *Proc. Natl. Acad.*, 84, 4552-4556.

69. Bork L., Bosch, S., and Moller C. A. (2001) Sporadic cerebellar ataxia associated with gluten sensitivity. *Brain*, 124, 1013-1019.

70. Bushara K. O., Goebel S. U., Shill H., Godfard L. G., and Hallett M. (2001) Gluten sensitivity in sporadic and hereditary cerebellar ataxia. *Ann. Neurol.*, 49, 540-543.

71. Fabry Z. and Raine C. S. and Hart M. N. (1994) Nervous tissues as an immune compartment: the dialect of the immune response in the CNS. *Immunol. Today*, 15, 218224.

72. Purcell A. E., Rocco M. M., Lenhart J. A., Hyder K., Zimmerman A. W., and Pevsner J. (2001) Assessment of neuronal cell adhesion molecule (NCAM) in autistic serum and postmortem brain. *J. Autism Dev. Discord*, 31, 183-193.

73. D'Eufemia P., Celli M:., Finocchiaro R., Pacifico L., Viozzi L., Zaccagnini M., Cardi E., Giardini O. (1996) Abnormal intestinal permeability in children with autism. *Acta Paediatrica.* 85(9):1076-1079.

74. Fombonne E. (Mar. 28, 1998) Inflammatory bowel disease and autism. *Lancet* 351(9107)955.

75. Richmond P., Goldblatt D. (1988) Autism, inflammatory bowel disease, and MMR vaccine. *Lancet.* 351(9112): 1355-1356; discussion 1356.

76. Horvath K., Papadimitriou J. C., Rabsztyn A., Drachenberg C., Tildon J. T. (1999) Gastrointestinal abnormalities in children with autistic disorder. *Journal of Pediatrics.* 135(5):559-563.

77. Wakefield A. J., Murch S. H., Anthony A., Linnell J., Casson D. M., Malik M., Berelowitz M., Thomson M. A., Harvey P., Valetine A., Davies S. E., and Walker-Smith J. A. (1998) Ileal-lymphoid-nodular hyperplasia, non-specific colitis, and pervasive development disorder in children. *Lancet*, 351, 637-641.

78. Vojdani, A., (2003) A look at infectious agents as a possible causative factor in cardiovascular disease: part 1. *Lab. Medicine* 34 (3):7-11.

79. Vojdani, A., (2003) A look at infectious agents as a possible causative factor in cardiovascular disease: part II. *Lab. Medicine* 34 (4):5-9.

80. Vojdani, A., (2003) A look at infectious agents as a possible causative factor in cardiovascular disease: part 111. *Lab. Medicine* 34 (5):24-31.

81. Kono, D. H., Park, M. S., Szydlik, A., Haraldsson, K. M., Duan, J. D., and Pearson D. L., (2001) Resistance to xenobiotic-induced autoimmunity maps to chromosome 1. Immunol. 167: 2396-2403.

82. Takeuchi K., et al. (1995) Analysis of the autoantibody response to fibrillarin in human disease and murine model of autoimmunity. *J. of Immunology.* 154:961-971.

83. Warren R. P., Singh V, K. (1996) Elevated serotonin levels in autism: association with the major histocompatibility complex. *Neuropsychobiology.* 34(2):72-75.

84. Cook E. H., Leventhal B. L. (1996) The serotonin system in autism. *Current Opinion in Pediatrics.* 8(4):348-354.

85. McDougle C. J., Naylor S. T., Cohen D. J., Aghajanian G. K., Heninger G. R., Price L. H. (1996) Effects of tryptophan depletion in drug-free adults with autisticdisorder. *Archives of General Psychiatry.* 53(11):993-1000.

86. Wang J., Charboneau R., Barke R. A., Loh H. H., and Roy S. (2002,) [L-opoid receptor mediates chronic restraint stress-induced lymphocyte apoptosis. J. *Immunol.,* 169, 36303636.

87. Courchesne, E. (1997) Brainstem, cerebellar, and limbic neuroanatomical abnormalities in autism. *Current Opinion in Neurobiology.* 7(2):269-278.

88. Misumi, Y., Hayashi, Y., Arakawa, F., and Ikehara, Y., (1992) Molecular cloning and sequence analysis of human dipeptidylpeptidase IV, a serine proteinases on the cell surface. *Biochem. Biophys. Acta.* 1131:333-336.

89. Hamann, J., Fiebig, H. and Strauss, M., (1993) Expression cloning of the early activation antigen CD69, a type II integral membrane protein with a C-type lectin domain. J. *Immunol.* 150:4920.

90. Iannone, F., Corrigal, V. M., and Panayi, G. S, (1996) CD69 on synovial T-cells in rheumatoid arthritis correlates with disease activity. Br. *J. Rheumatol.* 35:397-401.

91. Muscat, C., Bertotto, A., Agea, E., Bistoni, O., Ercolani, R., Tognelli, R., et al., (1994) Expression and functional role of 1F7 (CD26) antigen on peripheral blood and synovial fluid cells in rheumatoid arthritis patients. *Clin. Exp. Immunol.* 98:252-256.

92. Yu, X., Matsui, T., Otsuka, M., Senine, T., Yamamoto, K., Nishioka, K., et al., (2001) AntiCD69 autoantibodies cross-react with low density lipoprotein receptor-related protein 2 in systemic autoimmune diseases. *J. Immunol.* 166:1360-1369.

93. Chuchacovich M., Gatica H., Pizzo H. S. V., and Gonzalez-Gronow M. (2001) Characterization of human serum dipeptidylpeptidase IV (CD26) and analysis of its autoantibodies in patients with rheumatoid arthritis and other autoimmune diseases. *Clin. Exp. Rheumatol.,* 19, 673-680.

94. Gonzalez-Gronow M, Weber M R, Gawdi G and Pizzo S V (1998) Dipeptidylpeptidase IV (CD26) is a receptor for streptokinase on rheumatoid synovial fibroblasts. *Fibrinol. Proteol.,* 12, 129-135.

References (Example 1)

Ader, R., Felten, D. L. and Cohen, N., (Eds.) (2001). *Psychoneuroimmunology,* 3$^{rd}$ ed. Academic Press: New York.

Baba, H., Daune G. C., Ilyas, A., Pestronk, A., Comblath, D. R., Chaudhry, V., Griffin, J. W. and Quarles, R. H. (1989). Anti-GM$_1$ ganglioside antibodies with differing fine specificities in patients with multifocal motor neuropathy. *J. Neuroimmunol.* 25, 143-150.

Bajramovic, J. J., Plomp, A. C., Van der Goes, A., Koevoetes, C., Newcombe, J., Cuzner, M. L. and Van Noort, J. M. (2001). Presentation of α, β-crystalline to T cells in active multiple sclerosis lesions: An early event following inflammatory demyelination. *J. Immunol.* 164, 4359-4366.

Ballieux, R. E. (1992). Bidirectional communication between the brain and the immune system. *Eur. J. Clin. Invest.* 22 (Suppl. 1), 6-9.

Brock, H. P. M., Uccelli, A., de Rosbo, N. K., Bontrop, R. E., Roccatagliata, L., de Groot, N. G., Capello, E., Laman, J. D., Nicolayk, K., Mancardi, G., Ben-Nun, A. T. and Hart, B. A. (2000). Myelin/oligodendrocyte glycoprotein-induced autoimmune encephalomyelitis in common marmosets: The encephalitogenic T cell epitope p MOG 24-36 is presented by a monomorphic MHC class II molecule. *J. Immunol.* 165, 1093-1101.

Bronze, M. S., Dale, J. B. (1993). Epitope of *Streptococcal* M proteins that evoke antibodies that cross-react with human brain. *J. Immunol.* 151, 280-2828.

Chabraoui, F., Derrington, E. A., Mallie-Didier, F., Confavreux, C., Quincy, C. and Caudie, C. (1993). Dot-Blot immunodetection of antibodies against GM$_1$ and other gangliosides on PVDF-P membrane. *J. Immunol. Methods* 165, 225-230.

Chess, S., Fernandez, P. and Korn, S. (1978). Behavioral consequences of congenital rubella. *J. Pediatr.* 93, 669-703.

Edelson, S. B. and Cantor, D. S. (1998). Autism: Xenobiotic influences. *Toxicol. Ind. Health* 14, 799-811.

Edelson, S. B. and Cantor, D. S (2000). The neurotoxic etiology of the autistic spectrum disorder: A replicative study. *Toxicol. Ind. Health* 16, 239-247.

El-Fawal, H. A. N., Gong, Z., Little, A. R. and Evans, H. L. (1996). Exposure to mercury results in serum autoantibodies to neurotypic and gliotypic proteins. *Neurotoxicology* 17, 267-276.

El-Fawal, H. A. N., Waterman, S. J., DeFeo, A. and Shamy, M. Y. (1999). Neuroimmunology: Humoral assessment of neurotoxicity and autoimmune mechanisms. *Environmental Health Perspectives* 5, 767-775.

Fabry, Z., Raine, C. S., Hart and M. N. (1994). Nervous tissues as an immune compartment: The dialect of the immune response in the CNS. *Immunol. Today* 15, 218-224.

Fredman, P., Lycke, J., Andersen, O., Vrethem, M., Ernerudh, J. and Svennerholm, L. (1993). Peripheral neuropathy associated with monoclonal IgM antibody to glycolipids with a terminal glucoronyl-3-sulfate epitope. *J. Neurol.* 240, 381-387.

Fudenberg, H. H. (1996). Dialyzable lymphocyte extract (DlyE) in infantile onset autism: A pilot study. *Biotherapy* 9, 143-147.

Genain, C. P., Cannella, B., Hauser, S. L. and Raine, C. S. (1999). Identification of autoantibodies associated with myelin damage in multiple sclerosis. *Nature Med.* 5, 170-175.

Greunewald, R., Ropper, A. H. and Lior, H., (1991). Serologic evidence of *Camylobacter jejuni coli enteritis* in patients with Guillain-Barre syndrome. *Arch. Neurol.* 48, 1080-1082.

Grogan, J. L., Kramer, A., Nogai, A., Dong, L., Ohde, M., Schneider-Mergener, J., Kamrad, T. T. (1999). Cross-reactivity of myelin basic protein-specific T-cells with multiple microbial peptides: Experimental autoimmune encephalomyelitis induction in TCR transgenic mice. *J. Immunol* 163, 3764-3770.

Gupta, S., Aggarwal S., and Heads, C. (1996). Dysregulated immune system in children with autism: Beneficial effects of intravenous immune globulin on autistic characteristics. *Journal of Autism and Developmental Disorders* 26, 439-452.

Gupta, S., Lee, T., & Aggarwal, S. (1998). Alterations in Th1 and Th2 subsets of CD4+ and CD8+ T cells in autism. *Journal of Neuroimmunology*, 14, 499-504.

Gupta, S. (2000). Immunological treatments for autism. *Journal of Autism and Developmental Disorders* 30, 475-479.

Holz, A., Bielekova, B., Martin, R. and Oldstone, M. B. A. (2000). Myelin-associated oligodendrocytic basic protein: Identification of an encephalitogenic epitope and association with multiple sclerosis. *J. Immunol.* 164, 1103-1109.

Isoardo, G., Ferrero, B., Barbero, P., Cucci, A., Oggero, A., Pipieri, A., Ricci, A., Verdun, E., Bergamasco, B. and Durelli, L. (2001). Anti-GM$_1$ and anti-sulfatide antibodies in polyneuropathies. *Acta. Neurol. Scand.* 103, 180-187.

Ivarsson, S. A., Bjerre, L., Vegfors, P. and Ahlfors, K. (1990). Autism as one of several abnormalities in two children with congenital cytomegalovirus infection. *Neuropediatrics* 21, 102-103.

Kaldor, J., Speed, B. R., (1984). Guillain-Barre syndrome and *Campylobacter jejuni*: A serological study. *Br. Med. J.* 288, 1867-1870.

Kanner, L., (1943). Autistic disturbances of affective contact. *Nervous Child.* 2, 217-250.

Kusnecov, A. W., Liang, R. and Shurin, G. (1990). T-lymphocyte activation increases hypothalamic and expression of CRH MRNA and emotional reactivity to novelty. *J. Neurosciences,* 19, 4533-4541.

Lenz, D. C., Lu, L., Conant, S. B., Wolf, N. A., Gérard, H. C., Whittum-Hudson, J. A., Hudson, A. P., Swanborg, R. H. (2001). A *Chlamydia pneumoniae*-specific peptide induces experimental autoimmune encephalomyelitis in rats. *J. Immunol.* 167, 1803-1808.

Mecocci, P., Pametti, L., Romano, E., Scarelli, A., Chionni, F., Polidori, M. C., Palumbo, B., Cherubini and A., Senin, U. (1995). Serum anti-GFAP and anti-S100 autoantibodies in brain aging, Alzheimer's disease and vascular dememtia. *J. Neuroimmunol.* 57, 165-170.

Menage, P., Thibault, G., Barthelemy, C., Lelford, G., and Bardos, P. (1992). CD4+ CD45RA+ T lymphocytes deficiency in autistic children: Effect of a pyridoxine-magnesium treatment. *Brain Dysfunction* 5, 326-333.

Morse, D. C., Plug, A., Wesseling W., Van Den Berg, K. J. and Brouwer, A. (1996). Persistent alterations in regional brain glial fibrillary acidic protein and synaptophysin levels following pre-and postnatal polychlorinated biphenyl exposure. *Toxicology and Applied Pharmacology* 139, 252-261.

Nemni, R., Fazio, R., Quattrini, A., Lorenzetti, I., Mamoli, D. and Canal, N. (1993). Antibodies to sulfatide and chondroitin sulfate in patients with chronic sensory neuropathy. *J. Neuroimmunol.* 43, 79-86.

Partl, S., Herbst, H., Schaeper, F., Mohnhaupt, A. and Stoltenburg-Didinger, G. (1998). GFAP gene expression is altered in young rats following developmental low level lead exposure. *Neurotoxicology* 19, 547-552.

Purcell, A. E., Rocco, M. M., Lenhart, J. A., Hyder, K., Zimmerman, A. W. and Pevsner, J. (2001). Assessment of neuronal cell adhesion molecule (NCAM) in autistic serum and postmortem brain. *J. Autism and Dev. Disorder* 31, 183-193.

Qian, Y., Harris, E. D., Zheng, Y. and Tiffany-Castiglioni, E. (2000). Lead targets GRP78, a molecular chaperone, in C6 rat glioma cells. *Toxicology and Pharmacology* 163, 260-266.

Rodier, P. M., Ingram, J. L., Tisdale, B., Nelson, S. and Romano, J. (1996). Embryological origin for autism: Developmental abnormalities of the cranial nerve motor nuclei. *J. Compar. Neurol.* 370, 247-261.

Ropper, A. H. and Gorson, K. C. (1998). Neuropathies associated with paraproteinemia. *N. Engl. J. Med.* 338, 1601-1607.

Singh, V. K., Warren, R. P., Odell, J. D., Cole, P. and Warren, L. (1993). Antibodies to myelin basic protein in children with autistic behavior. *Brain, Behavior, and Immunity* 7, 97-103.

Singh, V. K., Warren, R. P., Averett, R., and Ghaziuddin, M. (1997). Circulating autoantibodies to neuronal and glial filament protein in autism. *Pediatric Neurology* 17, 88-90.

Stefferl, A., Schubart, A., Storch, M., Amini, A., Mather, I., Lassmann, H., Linington, C. (2000). Butrophilin, a milk protein, modulates the encephalitogenic T-cell response to myelin oligodendrocyte glycoprotein in experimental autoimmune encephalomyelitis. *J. Immunol.* 165, 2859-2865.

Vojdani, A., Brautbar, N., Campbell, A. W. (1994). Antibody to silicone and native macromolecules in women with silicone breast implants. *Immunopharmacol. and Immunotoxicol.* 16, 497-523.

Wakefield, A. J., Murch, S. H., Anthony, A., Linnell, J., Casson, D. M., Malik, M., Berelowitz, M., Thomson, M. A., Harvey, P., Valentine, A., Davies, S. E. and Walker-Smith, J. A. (1998). Ileal-Lymphoid-Nodular Hyperplasia, Non-specific colitis, and pervasive developmental disorder in children. *Lancet* 351, 637-641.

Warren, R. P., Foster, A., Margaretten, N. C., Pace, N. C. and Foster, A. (1986). Immune abnormalities in patients with autism. *Journal of Autism and Developmental Disorders* 16, 189-197.

Warren, R. P., Foster, A. and Margaretten, N. C. (1987). Reduced natural killer cell activity in autism. *Journal of the American Academy of Child and Adolescent Psychiatry* 26, 333-335.

Weizman, A., Weizman, R., Szekely, G. A., Wijsenbeek, H. and Livni, E. (1982). Abnormal immune response to brain tissue antigen in the syndrome of autism. *Am. J. Psychiatry* 139, 1462-1465.

Yonk, L. J., Warren, R. P., Burger, R. A., Cole, P., Odell, J. D., Warren, W. L., White, E. and Singh, V. K. (1990). CD4+ helper T cell depletion in autism. *Immunology Letters* 25, 344-346.

References (Example 2)

95. Vojdani A., A. W. Campbell, E. Anyanwu, A. Kashanian, K Bock and E. Vojdani. 2002. Antibodies to neuron-specific antigens in children with autism:

possible cross-reaction with encephalitogenic proteins from milk, *Chlamydia pneumoniae* and *streptococcus* group A. *J. Neuroimmunol.* 129:168:

96. Vader W., Y. Kooy, P. Van Veelen, A. De Ru, D. Harris, W. Benckuijsen, et al. 2002. The gluten response in children with celiac disease is directed toward multiple gliadin and glutenin peptides. *Gastroenterology* 122:1729.

97. Bronze M. S. and J. B. Dale. 1993. Epitope of *streptococcal M.* proteins that evoke antibodies that cross-react with the human brain. *J. Immunol.* 151:2820.

98. Bednarczyk J., S. M. Carroll, C. Marin and B. McIntyre. 1991. Triggering of the proteinases dipeptidylpeptidase IV (CD26) amplifies human T lymphocyte proliferation. *J. Cell Biochem.* 46:206:

99. Chuchacovich M., H. Gatica, H. S. V. Pizzo and M. Gonzalez-Grownow. 2001. Characterization of human serum dipeptidylpeptidase IV (CD26) and analysis of its autoantibodies in patients with rheumatoid arthritis and other autoimmune diseases. *Clin. Exp. Rheumatol.* 19:673:

References (Example 3)

100. Anderson R. P., P. Degano, A. J. Godkin, D. P. Jewell, and A. V. Hill. 2000. In vivo antigen challenge in celiac disease identifies a single transglutaminase-modified peptide as the dominant antigen T-cell epitope. Nat. Med. 6:337-342.

101. Ansorge, S., F. Buhling, T. Hoffmann, T. Kahne, K. Neubert, and D. Reinhold. 1995. DPP IV/CD26 on human lymphocytes: functional roles in cell growth and cytokine regulation. In Dipeptidyl Peptidase IV (CD26) in Metabolism and the Immune Response (Fleischer, B., ed.), Springer Verlag, Berlin. 163-184.

102. Barret, A. J., N. D. Rawlings, and J. F. Woessner ed. 1998. Handbook of Proteolytic Enzymes. Academic Press. 379-382.

103. Bouras, M., J. F. Huneau and D. Tome. 1996. The inhibition of intestinal dipeptidylaminopeptidase-IV promotes the absorption of enterostatin and des-arginine-enterostatin across rat jejunum in vitro. Life Sci. 59:2147-2155.

104. Bürk K, S. Bösch, C. A. Müller, et al. 2001. Sporadic cerebellar ataxia associated with gluten sensitivity. Brain 124:1013-1019.

105. Chatchatee P., K. M. Järviven, L. Bardina, .L Vila, K Beyere and H. A. Sampson. 2001. Identification of IgE and IgG binding epitope on β- and κ-casein in cow's milk-allergic patients. Clin. Exp. Allergy 31:1256-1262.

106. Chuchacovich, M., H. Gatica, H. S. V. Pizzo, and M. Gonzalez-Gronow. 2001. Characterization of human serum dipeptidylpeptidase IV (CD26) and analysis of its autoantibodies in patients with rheumatoid arthritis and other autoimmune diseases. *Clin. Exp. Rheumatol.* 19:673-680.

107. Chuchacovich, M., H. Gatica, P. Vial, J. Yovanovich, S. V. Pizzo, and M. Gonzalez-Gronow. 2002. Streptokinase promotes development of dipeptidylpeptidase IV (CD26) autoantibodies after fibrinolytic therapy in myocardial infarction patients. Clin. Diag. Lab. Immunol. 9:1253-1259.

108. Ciervo, A., P. Visca, A. Petrucca, L. M. Biasucci, A. Maseri, A. Cassone. 2002. Antibodies to 60-kilodalton heat shock protein and outer membrane protein 2 of *Chlamydia pneumoniae* in patients with coronary heart disease. Clin. Diag. Lab. Immunol. 9:66-74.

109. Cook, S. D. and P. C. Dowlny. 1981. The role of autoantibody and immune complexes in the pathogenesis of Guillain-Barre syndrome. Ann Neurol 9(suppl):70-79.

110. Delmas, B., J. Gelfi, R. L'Haridon, K. Vogell, H. Sjostrom, O. Noren and H. Laude. 1992. Aminopeptidase is a major receptor for the enteropathogenic Coronavirus TGEV. Nature 357:417-420.

111. Drexler, H. G. 1987. Classification of acute myeloid leukemias—a comparison of FAB immunophenotyping. Leukemia. 1:697-705.

112. Dropcho, E. J., Y. Chen, J. B. Posner and L. J. Old. 1987. Cloning of a brain protein identified by autoantibodies from a patient with paraneoplastic cerebellar degeneration. J. Immunol. 84:4552-4556.

113. Edelson, S. B., D. S. Cantor. 2000. The neurotoxic etiology of the autistic spectrum disorder: a replicative study. Toxicol. Ind. Health. 16:239-247.

114. Frustaci, A., L. Cuoco, C. Chimenti, M. Pieroni, G. Fioravanti, N. Gentilon, A. Maseri and G. Gasbarrini. 2002. Celiac disease associated with autoimmune myocarditis. Circulation 105:2611-2618.

115. Goding, J. W. 1978. Use of *staphylococcal* protein A as an immunological reagent. J. Immunol. Methods. 20:241-253.

116. Gonzalez-Gronow, M., M. R. Weber, G. Gawdi, and S. V. Pizzo. 1998. Dipeptidylpeptidase IV (CD26) is a receptor for streptokinase on rheumatoid synovial fibroblasts. Fibrinol. Proteol. 12:129-135.

117. Gonzalez-Gronow, M., M. Cuchacovich, D. M. Grigg, and S. V. Pizzo. 1996. Analysis of autoantibodies to plasminogen in the serum of patients with rheumatoid arthritis. J. Mol. Med. 74:463-469.

118. Greenbaum, E., A. Furst, A. Kiderman, B. Stewart, R. Levy, M. Schlesinger, A. Morag, Z. Zakay-Rones. 2001. Serum and mucosal immunological responses in children following the administration of a new inactivated intranasal antiinfluenza vaccine. J. Med. Virol. 65:178-184.

119. Gruenewald, R., A. H. Ropper, H. Lior et al. 1991. Serologic evidence of Campylobater jejuni coli enteritis in patients with Guillain Barre syndrome. Arch Neurol 48:1080-1082.

120. Gupta, S., T. Lee, and S. Aggarval. 1998. Alterations in Th1 and Th2 subsets of CD4+ and CD8+ T-cells in autism. J. Neuroimmunol. 14:499-504.

121. Hadjivassiliou, M., S. Boscolos, G. A. B. Davies-Jones, R. A. Grünwald, T. Not, D. S. Sanders, J. E. Simpson, E. Tongiorgi, C. A. Williamson and N. M. Woodroofe. 2002. The humoral response in the pathogenesis of gluten ataxia. Neurology 58:1221-26.

122. Harat S. D., N. Yacov, B. Gilburd, Y. Shoenfeld, and J. George. 2002. Oral tolerance with heat shock protein-65 attenuates mycobacterium tuberculosis-induced and high-fat-diet-driven atherosclerotic lesions. J. Am. Coll. Cardiol. 40:1333-1338.

123. Harlow, E., and D. Lane (ed). 1988. Antibodies: a laboratory manual. Cold Spring Harbor Laboratory Press, Cold Spring Harbor, N.Y. 98-108.

124. Hartun, H. P., G. Stoll, and K. V. Toyka. 1993. Immune reactions in the peripheral nervous system. In Dyck P J, Thomas P K, Griffin J W et al. Peripheral Neuropathy. Philadelphia, W B Saunders, pp. 418-444.

125. Hildrebrandt, M., W. Reutter, P. Arck, M. Rose, and B. Klapp. 2000. A guardian angel: the involvement of dipeptidylpeptidase IV in psychoneuroendocrine function, nutrition and immune defense. Clin. Sci. 99:93-104.

126. Ilyas, A. A., F. A. Mithen, M. C. Dalakas, et al. 1991. Antibodies to sulfated glycolipids in Guillain-Barre syndrome. J. Neurol Sci 105:108-117.
127. Ilyas A. A., F. A. Mithen, M. C. Dalakas, et al. 1992. Antibodies to acidic glycolipids in Guillain Barre syndrome and chronic inflammatory demyelinating polyneuropathy. J. Neurol Sci 107:1111-1211.
128. Jyonouchi H, S. N. Sun, and H. Le. 2001. Proinflammatory and regulatory cytokine production associated with innate and adaptive immune responses in children with autism spectrum disorders and developmental regression. J. Neuroimmunol. 120:170-179.
129. Kaiser, R., R. Kaufman, M. Czygan, H. Lang, C. H. Lucking. 1993. Guillain-Barre syndrome following streptokinase therapy. Clin. Investig. 71:795-801.
130. Kameoka, J., T. Tanaka, Y. Nojima, S. F. Schlossman, and C. Morimoto. 1993. Direct association of adenosine deaminase with a T-cell activation antigen. CD26. Science 261:466-469.
131. Kol, A., T. Bourcier, A. H. Lichtman, and P. Libby. 1991. Chlamydial and human heat shock protein 60s activate human vascular endothelium, smooth muscle cells and macrophages. J. Clin. Invest. 103 (4):571-577.
132. Letarte, M., S. Vera, R. Tran, J. B. L. Addis, R. J. Onizuka, E. J. Quackenbush, C. V. Jongeneel, and R. R. McInnes. 1988. Common acute lymphocyte lukemia antigen is identical to endopeptidase. J. Exp. Med. 168:1247-1253.
133. Look, A. T., R. A. Ashmun, L. H. Shapiro, and S. H. Peiper. 1989. Human myeloid plasma Membrane glucoprotein CD13 (gP150) is identical to aminopeptidase N. J. Clin. Invest. 83:1299-1307.
134. Mabee, C. L., M. J. McGuire, and D. L. Thiele. 1998. Dipeptidylpeptidase I and Granzyme A are coordinately expressed during CD8+ T-cell development and differentiation. J. Immunol. 150:5880-5885.
135. Matsas, R., S. L. Stephenson, J. Hryszko, A. J. Turner, and A. J. Kenny. 1985. The metabolism of neuropeptides; phase separation of synaptic membrane preparations with Triton X-114 reveals presence of aminopeptidase N. Biochem. J. 231:445-449.
136. Misumi, Y., Y. Hayashi, F. Arakawa, and Y. Ikehara. 1992. Molecular cloning and sequence analysis of human dipeptidyl peptidase IV, A serine proteinase on the cell surface. Biochem. Biophys. Acta. 1131 (3):333-336.
137. Murray, D. L., D. H. Ohlendorf, and P. M. Schlievert. 1995. *Staphylococcal* and *streptococcal superantigens:* Their role in human diseases. ASM News. 61:229-235.
138. Muscat, C., A. Bertotto, E. Agea, O. Bistoni, R. Ercolani, R. Tognelli, F. Spinozzi, M. Cesarotti, and R. Gerli. 1994. Expression and functional role of 1F7 (CD26) antigen on peripheral blood and synovial fluid cells in rheumatoid arthritis patients. Clin. Exp. Immunol. 98:252-256.
139. Nakao, H., K Eguchi, A. Kawakami, K Migita, Y. Otsubo, C. Ueki, H. Shimomura, M. Tezuka, K Maeda Matsunaga, and S. Nagataki. 1989. Increment of Tal positive cells in peripheral blood from patients with rheumatoid arthritis. J. Rheumatol. 16:904-914.
140. Nurkka, A., H. Ahman, M. Yaich, J. Eskola, and H. Kayhty. 2001. Serum and salivary anti-capsular antibodies in infants and children vaccinated with octavalent pneumococcal conjugate-vaccines, Pncd and Pnct. Vaccine. 2:194-201.
141. Paliard, X., S. G. West, J. A. Lafferty, J. R. Clements, J. W. Kappler, P. Marrack, and B. L. Kotzin. 1991. Evidence for the effects of a superantigen in rheumatoid arthritis. Science. 253:325-329.
142. Riemann, D., A. Kehlen, and J. Langner. 1999. CD13—not just a marker in leukemia typing. Immunology Today 20:83-88.
143. Saida T., K. Saida, and R. P. Lisak. 1982. In vivo demyelinating activity of sera from patients with Guillain-Barre syndrome. Ann Neurol 11:69-75.
144. Sentandrau, M. A., and F. Toldra. 2000. Purification and biochemical properties of dipeptidylpeptidase I from porcine skeletal muscle. J. Agric. Food Chem. 48:5014-5022.
145. Singh, V. K, R. P. Warren, R. Averett, and M. Ghaziuddin. 1997. Circulating autoantibodies to neuronal and glial filament protein in autism. Pediatr. Neurol. 17:88-90.
146. Sollid, L. M. 2002. Coeliac Disease: Dissecting a complex inflammatory disorder. Nature Review Immunology 2:647-655.
147. Squire, I. B., W. Lawley, S. Fletcher, E. Holme, W. S. Hillis, C. Hewitt, and K. L. Woods. 1999. Humoral and cellular immune responses up to 7.5 years after administration of streptokinase for acute myocardial infarction. E. Heart J. 20:1245-1252.
148. Stancikova, M., Z. Lojda, J. Lukac, and M. Ruzickova. 1992. Dipeptidylpeptidase IV in patients with systemic lupus erythematosus. Clin. Exp. Rheumatol. 10:381-385.
149. Stollberger C., and J. Finsterer. 2002. Role of infections and immune factors in coronary and cerebrovascular arteriosclerosis. Clin. Diag. Lab. Immunol. 9:207-215.
150. Vayssier, C., D. Mayrand, and D. Grenier. 1994. Detection of stress proteins in Porphyromonas gingivalis and other oral bacteria by Western immunoblotting analysis. FEMS Microbiol. Lett. 121:303-307.
151. Vojdani, A., A. W. Campbell, E. Anyanwu, A. Kashanian, K. Bock, and E. Vojdani. 2002. Antibodies to neuron-specific antigens in children with autism: possible cross-reaction with encephalitogenic proteins from milk, Chlamydia pneumoniae and streptococcus group A. J. Neuroimmunol. 129:168-177.
152. Wakefield, A. J., S. H. Murch, A. Anthony, J. Linnell, D. M. Casson, M. Malik, M. Berelowitz, M. A. Thomson, P. Harvey, A. Valetine, S. E. Davies, and J. A. Walker-Smith. 1998. Ileal-lymphoid-nodular hyperplasia, non-specific colitis, and pervasive developmental disorder in children. Lancet 351: 637-641.
153. Warren, R. P., A. Foster, N. C. Margaretten, N. C. Pace and A. Foster. 1986. Immune abnormalities in patients with autism. J. Autism Dev. Disord. 16:189-197.
154. Warren, R. P., A. Foster, and N. C. Margarette. 1987. Reduced natural killer activity in autism. J. Am. Acad. Child Adolesc. Psychiatry 26:333-335.
155. Weizman, A., R. Weizman, G. A. Szekely, H. Wijsenbeek, and E. Livni. 1982. Abnormal immune response to brain tissue antigen in the syndrome of autism. Am. J. Psychiatry. 139:1462-1465.
156. Wolters, P. J., M. Laig-Webster, and G. H. Caughey. 2000. Dipeptidyl peptidase I cleaves matrix-associated proteins and is expressed mainly by mast cells in normal dog airways. Am. J. Respir. Cell. Mol. Biol. 22:183-190.
157. Xiao, Q., R. P. Boushey, M. Cino, D. J. Drucker and P. L. Brubaker. 2000. Circulating levels of glucagon-like peptide-2 in human subjects with inflammatory bowel disease. AM J. Physiol. Regulatory Integrative Comp. Physiol. 278:R1057-R1063.
158. Yamazaki, K, Y. Ohsawa, K Tabeta, H. Ito, K Ueki, T. Oda, H. Yoshie and G. J. Seymour. 2002. Accumulation of heat shock protein 60-reactive T-cells in the gingivcal tissues of periodontitis patients. Infect. Immun. 70:2492-2501.

159. Yeager, C. L., R. A. Ashmun, R. K. Williams, C. B. Cardellichio, L. H. Shapiro, A. T. Look, and K. V. Holmes. 1992. Human aminopeptidase N is a receptor for human Coronavirus 229E. Nature 357:420-422.

160. Yonk, L. J., R. P. Warren, R. A. Burger, P. Cole, J. D. Odell, W. R. Warren, E. White, and V. K. Singh. 1990. CD4+ helper T-cell depletion in autism. Immunol. Lett. 25:344-346.

161. Young, R. A., and T. J. Elliot. 1989. Stress proteins, infection, and immune surveillance. Cell. 59:5-8

What is claimed is:

1. A method for diagnosing an autistic spectrum disorder in a patient, comprising the steps of:
   a) determining a level of antibodies to a protein selected from the group consisting of an aminopeptidase N (CD13), dipeptidyl peptidase IV (CD26), dipeptidyl peptidase I and CD69, in one or more samples from the patient; and
   b) comparing the level of antibodies determined in step a) with a normal level of the antibodies from control subjects, wherein
      (i) normal level or lower than normal levels of antibodies indicate absence of autistic spectrum disorder in said patient; and
      (ii) higher than normal level of the antibodies indicates the presence of the autistic spectrum disorder in said patient.

2. The method of claim 1, wherein the autistic spectrum disorder is autism.

3. The method of claim 1, wherein the normal level of antibodies is calculated by taking a mean of levels of antibodies in individuals without symptoms relating the autistic spectrum disorder.

4. The method of claim 1, wherein the higher than normal level of antibodies is higher than about two standard deviations of normal level of antibodies of a control group.

5. The method according to claim 1, wherein determining the level of antibodies in any or all of steps a) and b) is accomplished using an immunoassay.

6. The method according to claim 5, wherein the immunoassay is selected from the group consisting of ELISA, RAST, dot blot, Western blot, and ELISPOT.

7. The method according to claim 1, wherein the antibodies are selected from the group consisting of IgG, IgA, and IgM.

* * * * *